(12) United States Patent
Cashman et al.

(10) Patent No.: US 12,071,472 B2
(45) Date of Patent: Aug. 27, 2024

(54) METHODS OF REDUCING TOXICITY INDUCED BY AMYLOID BETA (A-BETA) OLIGOMERS USING ANTIBODIES SPECIFIC TO A-BETA OLIGOMERS

(71) Applicants: The University of British Columbia, Vancouver (CA); ProMIS Neurosciences, Inc., Toronto (CA)

(72) Inventors: Neil R. Cashman, Vancouver (CA); Steven S. Plotkin, Vancouver (CA); Judith Maxwell Silverman, Whistler (CA); Ebrima Gibbs, Port Moody (CA); Johanne Kaplan, Sherborn, MA (US)

(73) Assignees: The University of British Columbia, Vancouver (CA); ProMIS Neurosciences Inc., Toronto (CA)

( * ) Notice: Subject to any disclaimer, the term of this patent is extended or adjusted under 35 U.S.C. 154(b) by 607 days.

(21) Appl. No.: 16/318,605

(22) PCT Filed: Jul. 18, 2017

(86) PCT No.: PCT/CA2017/050866
§ 371 (c)(1),
(2) Date: Jan. 17, 2019

(87) PCT Pub. No.: WO2018/014126
PCT Pub. Date: Jan. 25, 2018

(65) Prior Publication Data
US 2020/0172602 A1  Jun. 4, 2020

Related U.S. Application Data

(60) Provisional application No. 62/507,633, filed on May 17, 2017, provisional application No. 62/507,587, filed on May 17, 2017, provisional application No. 62/443,766, filed on Jan. 8, 2017, provisional application No. 62/363,566, filed on Jul. 18, 2016.

(30) Foreign Application Priority Data

Nov. 9, 2016  (WO) ................ PCT/CA2016/051303

(51) Int. Cl.
| | | |
|---|---|---|
| A61K 39/395 | (2006.01) |
| A61K 39/00 | (2006.01) |
| A61K 49/00 | (2006.01) |
| A61P 25/00 | (2006.01) |
| A61P 25/28 | (2006.01) |
| C07K 16/00 | (2006.01) |
| C07K 16/18 | (2006.01) |
| G01N 33/68 | (2006.01) |
| A61K 38/17 | (2006.01) |

(52) U.S. Cl.
CPC .............. C07K 16/18 (2013.01); A61P 25/28 (2018.01); G01N 33/6854 (2013.01); A61K 38/1716 (2013.01); A61K 39/0007 (2013.01); *A61K 2039/505* (2013.01); *A61K 49/0008* (2013.01); *C07K 2317/24* (2013.01); *C07K 2317/34* (2013.01); *C07K 2317/55* (2013.01); *C07K 2317/565* (2013.01); *C07K 2317/76* (2013.01); *C07K 2317/92* (2013.01); *G01N 33/6896* (2013.01); *G01N 2333/4709* (2013.01); *G01N 2800/2821* (2013.01)

(58) Field of Classification Search
CPC ................ C07K 16/18; C07K 2317/76; C07K 2319/00; C07K 5/1021; C07K 5/1024; C07K 7/64; C07K 7/06; C07K 14/4711; A61K 2300/00; A61K 2039/505; A61K 38/57; A61K 39/00; A61K 38/00; A61K 47/646; A61K 38/12; A61K 35/30; A61K 39/0008; A61P 25/28; A61L 15/32; A61L 15/44; A61L 2300/252; G01N 33/6896; C12N 5/0622; C12N 5/0623; C12N 5/16; C12N 5/0618; C12N 5/0619; Y02A 50/464; Y02A 50/466
See application file for complete search history.

(56) References Cited

U.S. PATENT DOCUMENTS

| | | | |
|---|---|---|---|
| 5,283,185 A | 2/1994 | Epand et al. |
| 5,562,909 A | 10/1996 | Allcock |
| 5,593,846 A | 1/1997 | Schenk et al. |
| 5,770,429 A | 6/1998 | Lonberg et al. |
| 5,814,014 A | 9/1998 | Elsberry et al. |
| 6,043,283 A | 3/2000 | Giulian |
| 6,071,493 A | 6/2000 | Giulian |
| 6,114,598 A | 9/2000 | Kucherlapati et al. |
| 6,150,584 A | 11/2000 | Kucherlapati et al. |
| 6,319,498 B1 | 11/2001 | Findeis et al. |

(Continued)

FOREIGN PATENT DOCUMENTS

| | | |
|---|---|---|
| AU | 2007234495 A1 | 12/2007 |
| CN | 101670105 A | 3/2010 |

(Continued)

OTHER PUBLICATIONS

Guo et al., PNAS 2004; 101:9205-9210.*

(Continued)

*Primary Examiner* — Chang-Yu Wang

(74) *Attorney, Agent, or Firm* — Bereskin & Parr LLP; Carmela De Luca; Alissa Hyppolite

(57) ABSTRACT

The disclosure pertains to antibodies that bind A-beta oligomers and methods of making and using said antibodies.

19 Claims, 1 Drawing Sheet

Specification includes a Sequence Listing.

(56) References Cited

U.S. PATENT DOCUMENTS

| | | |
|---|---|---|
| 6,451,544 B2 | 9/2002 | Giulian |
| 6,475,742 B2 | 11/2002 | Giulian |
| 6,475,745 B1 | 11/2002 | Giulian |
| 6,890,535 B1 | 5/2005 | Schenk |
| 6,913,745 B1 | 7/2005 | Schenk |
| 7,012,061 B1 | 3/2006 | Reiss et al. |
| 7,179,892 B2 | 2/2007 | Basi et al. |
| 7,189,819 B2 | 3/2007 | Basi et al. |
| 7,256,273 B2 | 8/2007 | Basi et al. |
| 7,288,523 B2 | 10/2007 | Nordstedt et al. |
| 7,575,880 B1 | 8/2009 | Schenk |
| 7,582,733 B2 | 9/2009 | Basi et al. |
| 7,588,766 B1 | 9/2009 | Schenk |
| 7,625,560 B2 | 12/2009 | Basi et al. |
| 7,700,751 B2 | 4/2010 | Basi et al. |
| 7,790,856 B2 | 9/2010 | Schenk |
| 7,871,615 B2 | 1/2011 | Basi et al. |
| 7,893,214 B2 | 2/2011 | Schenk |
| 7,932,048 B2 | 4/2011 | Mendez |
| 7,964,192 B1 | 6/2011 | Schenk |
| 7,977,316 B2 | 7/2011 | Schenk |
| 8,003,097 B2 | 8/2011 | Schroeter et al. |
| 8,034,339 B2 | 10/2011 | Schenk |
| 8,124,081 B2 | 2/2012 | Schenk |
| 8,128,928 B2 | 3/2012 | Basi et al. |
| 8,216,577 B2 | 7/2012 | Bardoff et al. |
| 8,613,920 B2 | 12/2013 | Lieberburg et al. |
| 8,613,931 B2 | 12/2013 | Mandler |
| 8,623,365 B2 | 1/2014 | Davies |
| 8,784,810 B2 | 7/2014 | Lieberburg et al. |
| 8,916,165 B2 | 12/2014 | Basi et al. |
| 9,051,363 B2 | 6/2015 | Basi et al. |
| 9,067,981 B1 | 6/2015 | Basi |
| 9,084,832 B2 | 7/2015 | Nordstrom et al. |
| 9,216,217 B2 | 12/2015 | Cashman |
| 9,221,812 B2 | 12/2015 | Kroth et al. |
| 9,334,303 B2 | 5/2016 | Mediannikov et al. |
| 9,493,496 B2 | 11/2016 | Geng et al. |
| 9,535,076 B2 | 1/2017 | Kayed et al. |
| 9,644,025 B2 | 5/2017 | Black et al. |
| 10,751,382 B2* | 8/2020 | Cashman .............. C07K 5/0808 |
| 10,774,120 B2* | 9/2020 | Cashman ............... C07K 5/101 |
| 2001/0016326 A1 | 8/2001 | Giulian |
| 2001/0016327 A1 | 8/2001 | Giulian |
| 2005/0267029 A1 | 12/2005 | Ancsin et al. |
| 2007/0110750 A1 | 5/2007 | Glabe et al. |
| 2008/0107649 A1 | 5/2008 | Zubriggen |
| 2008/0299111 A1 | 12/2008 | Delacourte |
| 2009/0246191 A1 | 10/2009 | O'Nuallain et al. |
| 2010/0104504 A1 | 4/2010 | Echeverria Moran |
| 2011/0171243 A1 | 7/2011 | Mandler et al. |
| 2012/0328605 A1 | 12/2012 | Larocque et al. |
| 2013/0136747 A1 | 5/2013 | Bardroff et al. |
| 2013/0252901 A1 | 9/2013 | Mediannikov et al. |
| 2015/0105344 A1 | 4/2015 | Geng et al. |
| 2015/0322143 A1 | 11/2015 | Kayed |
| 2017/0021020 A1 | 1/2017 | Bollyky et al. |
| 2018/0030429 A1* | 2/2018 | King .................. C07K 14/435 |
| 2018/0125920 A1* | 5/2018 | Cashman ................ C12N 5/16 |
| 2018/0319856 A1* | 11/2018 | Cashman ............. A61K 47/646 |
| 2018/0330045 A1* | 11/2018 | Plotkin .................. G16B 15/20 |
| 2018/0346535 A1* | 12/2018 | Cashman ........... A61K 39/0008 |
| 2019/0151401 A1* | 5/2019 | Cashman ............... A61K 38/07 |
| 2020/0172602 A1* | 6/2020 | Cashman ........... A61K 51/1018 |
| 2021/0087243 A1 | 3/2021 | Cashman et al. |
| 2021/0087244 A1* | 3/2021 | Cashman ........... A61K 39/0007 |

FOREIGN PATENT DOCUMENTS

| | | |
|---|---|---|
| CN | 102112488 A | 6/2011 |
| CN | 102858796 A | 1/2013 |
| CN | 102869680 A | 1/2013 |
| EP | 1676859 A1 | 5/2006 |
| EP | 2377860 A1 | 10/2011 |
| EP | 2511296 A1 | 10/2012 |
| JP | 2011-504360 A | 2/2011 |
| JP | 2012-524023 A | 10/2012 |
| JP | 2013-500941 A | 1/2013 |
| JP | 2013-537424 A | 10/2013 |
| JP | 2019-533426 | 11/2019 |
| WO | 88/09336 A1 | 5/1988 |
| WO | 90/14387 A1 | 5/1990 |
| WO | 91/17271 A1 | 5/1991 |
| WO | 92/01047 A1 | 7/1991 |
| WO | 96/14831 A1 | 11/1994 |
| WO | 95/17211 A1 | 12/1994 |
| WO | 1995/006477 A1 | 3/1995 |
| WO | 95/34323 A2 | 6/1995 |
| WO | 96/06627 A1 | 7/1995 |
| WO | 01/62801 A2 | 2/2001 |
| WO | 2001/39796 A2 | 6/2001 |
| WO | 2001062801 A2 | 8/2001 |
| WO | 02/064734 A2 | 8/2002 |
| WO | 2003/070760 A2 | 2/2003 |
| WO | 2003/070760 A2 | 8/2003 |
| WO | 2003070760 A2 | 8/2003 |
| WO | 2004/029629 A1 | 4/2004 |
| WO | 2004/058239 A1 | 7/2004 |
| WO | 2004/071408 A2 | 8/2004 |
| WO | 2006/066089 A1 | 12/2005 |
| WO | 2006/095041 A1 | 9/2006 |
| WO | 2006/125324 A1 | 11/2006 |
| WO | 2007/068429 A1 | 12/2006 |
| WO | 2007/059000 A2 | 5/2007 |
| WO | 2008/060364 A2 | 5/2008 |
| WO | 2008/088983 A1 | 7/2008 |
| WO | 2008088983 A1 | 7/2008 |
| WO | 2008/156621 A1 | 12/2008 |
| WO | 2008/156622 A1 | 12/2008 |
| WO | 2009086539 A2 | 12/2008 |
| WO | 2009/048537 A2 | 4/2009 |
| WO | 2009/048538 A2 | 4/2009 |
| WO | 2009/052439 A2 | 4/2009 |
| WO | 2009/065054 A2 | 5/2009 |
| WO | 2009056490 A1 | 5/2009 |
| WO | 2009143489 A2 | 11/2009 |
| WO | 2009/149487 A2 | 12/2009 |
| WO | 2010/002251 A1 | 1/2010 |
| WO | 2010/040209 A1 | 4/2010 |
| WO | 2010119704 A1 | 10/2010 |
| WO | 2010/128139 A1 | 11/2010 |
| WO | 2011016238 A1 | 2/2011 |
| WO | 2011/033046 A1 | 3/2011 |
| WO | 2011/104696 A1 | 9/2011 |
| WO | 2011/106885 A1 | 9/2011 |
| WO | 2012104824 A1 | 8/2012 |
| WO | 2002/096937 A2 | 12/2012 |
| WO | 2013/020723 A1 | 2/2013 |
| WO | 2013/071267 A1 | 5/2013 |
| WO | 2013/164357 A1 | 11/2013 |
| WO | 2014/031697 A3 | 2/2014 |
| WO | 2014/161875 A1 | 4/2014 |
| WO | 2015/017900 A1 | 2/2015 |
| WO | 2015031698 A1 | 3/2015 |
| WO | 2015/113169 A1 | 8/2015 |
| WO | 2017025918 A1 | 2/2017 |
| WO | 2017/079831 A1 | 5/2017 |
| WO | 2017/079832 A1 | 5/2017 |
| WO | 2017/079833 A1 | 5/2017 |
| WO | 2017/079834 A1 | 5/2017 |
| WO | 2017/079835 A1 | 5/2017 |
| WO | 2017/079836 A1 | 5/2017 |
| WO | 2018/014126 A1 | 1/2018 |

OTHER PUBLICATIONS

Tayebati, Mech. Ageing Dev. 2006. 127: 100-8.*
Sarter, Neurosci. and Biobehav. Rev. 2004. 28: 645-650.*
Henstridge et al. Nat. Rev. Neurosci. 2019; 20: 94-107.*
Swerdlow, Clin. Interv. Ageing 2007; 2:347-359.*
Atwood et al., J. Alzheimer's Disease; 2015; 47:33-47.*
Anger. Neurotoxicology 1991. 12: 403-13.*
Burgess et al. J of Cell Bio. 1990, 111:2129-2138.*

(56) References Cited

OTHER PUBLICATIONS

Pawson et al. 2003, Science 300:445-452.*
Alaoui-Ismaili et al., Cytokine Growth Factor Rev. 2009; 20:501-507.*
European Patent Application No. 17830149.5 Extended European Search Report dated Jan. 31, 2020.
Fritschi, Sarah K. et al. Highly potent soluble amyloid-β seeds in human Alzheimer brain but not cerebrospinal fluid. Brain: a journal of neurology 137: Pt 11. 2909-2915 Nov. 2014.
Kaplan Johanne. Harnessing the Power of Precision Medicine to Conquer Neurodegenerative Diseases. Presented Sep. 14, 2016.
Wilcock, Donna M. et al. Passive immunotherapy against Aβ in aged APP-transgenic mice reverses cognitive deficits and depletes parenchymal amyloid deposits in spite of increased vascular amyloid and microhemorrhage. Journal of Neuroinflammation, 2004, 1:24.
Racke, Margaret M. et al. Exacerbation of Cerebral Amyloid Angiopathy-Associated Microhemorrhage in Amyloid Precursor Protein Transgenic Mice by Immunotherapy Is Dependent on Antibody Recognition of Deposited Forms of Amyloid β. The Journal of Neuroscience, Jan. 19, 2005. 25(3):629-636.
Pfeifer M. et al. Cerebral Hemorrhage After Passive Anti-Aβ Immunotherapy. Science. vol. 298 Nov. 15, 2002.
Wilcock, Donna M. et al. Deglycosylated Anti-Amyloid-β Antibodies Eliminate Cognitive Deficits and Reduce Parenchymal Amyloid with Minimal Vascular Consequences in Aged Amyloid Precursor Protein Transgenic Mice. Journal of Neuroscience. May 17, 2006. 26(20):5340-5346.
Goni, Fernando et al. Production of Monoclonal Antibodies to Pathologic β-sheet Oligomeric Conformers in Neurodegenerative Diseases. Scientific Reports. Aug. 2017.
Langer, Franziska et al. Soluble Aβ Seeds Are Potent Inducers of Cerebral β-Amyloid Deposition. J Neurosci 31: 41. 14488-14495 Oct. 2011.
Sardar Sinha, Maitrayee et al. Alzheimer's disease pathology propagetion by exosomes containing toxic amyloid-beta oligomers. Acta Neuropathologica. Jun. 2018.
Giulian, D. et al. The HHQK Domain of b-Amyloid Provides a Structural Basis for the Immunopathology of Alzheimer's Disease. The Journal of Biological Chemistry. vol. 273, No. 45, issue of Nov. 6, pp. 29719-29726, 1998.
Winkler K. et al. Competition of Aβ amyloid peptide and apolipoprotein E for receptor-mediated endocytosis. Journal of Lipid Research, vol. 40, 1999.
Kaplan, Johanne. Pre-Clinical: Basic Therapeutics—Targeting Amyloid or TAU. Presented at the Alzheimer's International Conference Jul. 2007.
Aprile, Francesco A. et al. Selective targeting of primary and secondary nucleation pathways in Aβ42 aggregation using a rational antibody scanning method. Molecular Neuroscience, Science Advances; 2017, 3. Jun. 21, 2017.
Wang, J. et al. Effects of an amyloid-beta 1-42 oligomers antibody screened from a phage display library in APP/PS1 transgenic mice. Brain Res. Mar. 15, 2016, vol. 1635, pp. 169-179.
Silverman, Judith et al. Novel Amyloid-β Oligomer-Specific Epitopes: A Hypothesis Drivin Aproach to Alzheimer's Immunotherapeutics. Abstract presented at the Alzheimer's Association International Conference Jul. 2016.
Gibbs, Ebrima et al. Rational generation of Aβ oligomer-specific antibodies through computational identification of conformational epitopes. Abstract presented at 13th International Conference on Alzheimer's & Parkinson's (AD/PD), Apr. 2017.
Plotkin, Steven et al. A computational Method to Predict Disease-Specific Epitopes in Aβ, and its Application to Oligomer-Selective Antibodies for Alzheimer's Immunotherapy. Presented at the Alzheimer's association international conference on Jul. 27, 2016.
Hollta, Mikko et al. Evaluating Amyloid-β Oligomers in Cerebrospinal Fluid as a Biomarker for Alzheimer's Disease. Plos One. Jun. 2013, vol. 8, Issue 6.
Plotkin, Steven et al. Achieving the optimal profile for Alzheimer's immunotherapy: Rational generation of antibodies specific for toxic Aβ oligomers. Abstract presented at the American Academy of Neurology conference on Apr. 2017.
Cashman, Neil et al. Epitope Identification of Toxic Propagating Strains of Aβ Oligomers. presented at PRION 2017, the International Conference Deciphering Neurodegenerative Disorders in Edinburgh, Scottland on May 25, 2017.
Fukumoto, H. et al. High-molecular-weight beta-amyloid oligomers are elevated in cerebrospinal fluid of Alzheimer patients. The FASEB Journal 24, 2716-2726, 2010.
Lesne, S. E. et al. Brain amyloid-beta oligomers in ageing and Alzheimer's disease. Brain 136, 1383-1398, 2013.
Ferreira, S. T., et al. Soluble amyloid-b oligomers as synaptotoxins leading to cognitive impairment in Alzheimer's disease. Frontiers in Cellular Neuroscience 9, (2015).
Figueiredo, C. P. et al. Memantine rescues transient cognitive impairment caused by high-molecular-weight abeta oligomers but not the persistent impairment induced by low-molecular-weight oligomers. J Neurosci 33, 9626-9634, 2013.
Tapiola, Tero, et al. Cerebrospinal Fluid β-Amyloid 42 and Tau Proteins as Biomarkers of Alzheimer-Type Pathologic Changes in the Brain. Arch Neurol. 2009, 66(3):382-389.
Krafft, Grant et al. ACU-193: A candidate therapeutic antibody that selectively targets soluble beta-amyloid oligomers, Alzheimer's & Dementia: The Journal of the Alzheimer's Association, Jan. 1, 2013, pp. P326-P326.
Hillen, Heinz et al. Generation and Therapeutic Efficacy of Highly Oligomer-Specific beta-Amyloid Antibodies, The Journal of Neuroscience, Society for Neuroscience, US, vol. 30, No. 31, Aug. 4, 2010, pp. 10369-10379.
Hoogerhout, Peter et al. A Cyclic Undecamer Peptide Mimics a Turn in Folded Alzheimer Amyloid β and Elicits Antibodies against Oligomeric and Fibrillar Amyloid and Plaques, Plos One, vol. 6, No. 4, Jan. 1, 2011, pp. e19110-e19110.
Arai, Tadamasa et al. A Cyclic KLVFF-Derived Peptide Aggregation Inhibitor Induces the Formation of Less-Toxic Off-Pathway Amyloid-β Oligomers, Chembiochem, vol. 15, No. 17, Sep. 26, 2014, pp. 2577-2583.
Cho, Patricia Y. et al. A Cyclic Peptide Mimic of the β-Amyloid Binding Domain on Transthyretin, ACS Chemical Neuroscience, vol. 6, No. 5, Mar. 9, 2015, pp. 778-789.
Liu, Cong et al. Characteristics of Amyloid-Related Oligomers Revealed by Crystal Structures of Macrocyclic β-Sheet Mimics, Journal of the American Chemical Society, vol. 133, No. 17, May 4, 2011, pp. 6736-6744.
Perez De La Lastra, J. M. et al. Epitope mapping of 10 monoclonal antibodies against the pig analogue of human membrane cofactor protein (MCP), Immunology, vol. 96, No. 4, Apr. 1, 1999, pp. 663-670.
McLaurin, JoAnne et al. Interactions of Alzheimer amyloid-β peptides with glucosaminoglycans. Effects on fibril nucleation and growth. E ur. J. Biochem. 266, 1101-1110 (1999).
Fraser, P.E. et al. Conformation and Fibrillogenesis of Alzheimer Aβ Peptides with Selected Substitution of Charges Residues. J. Mol. Biol. (1994) 244, 64-73.
Kaplan, Johanne. Harnessing the Power of Precision Medicine to Conquer Neurodegenerative Diseases (Presentation). CNS Diseases World Summit, Sep. 14, 2016.
Kaplan, Johanne et al. Targeting of Toxic Amyloid-Beta Oligomer Species by Monoclonal Antibody PMN310: Precision Drug Design for Alzheimer's Disease (Presentation). Alzheimer's Association International Conference, Jul. 17, 2017.
Kaplan, Johanne et al. Targeting of toxic amyloid-beta oligomer species by monoclonal antibody PMN310: Precision drug design for Alzheimer's disease (Abstract). Alzheimer's Association International Conference, Jul. 17, 2017.
Plotkin, Steven S. et al. Achieving the optimal profile for Alzheimer's immunotherapy: Rational generation of antibodies specific for toxic Aβ oligomers (Poster). American Academy of Neurology, Apr. 2017.
Plotkin, Steven S. et al. Achieving the optimal profile for Alzheimer's immunotherapy: Rational generation of antibodies specific for toxic Aβ oligomers (Abstract). American Academy of Neurology, Apr. 2017.

(56) References Cited

OTHER PUBLICATIONS

Silverman, Judith M. et al. Novel Aβ Oligomer-Specific Epitopes: A Hypothesis-Driven Approach to Alzheimer's Immunotherapeutics (Poster). Alzheimer's Association International Conference, Jul. 19, 2016.
Silverman, Judith M. et al. Novel Aβ Oligomer-Specific Epitopes: A Hypothesis-Driven Approach to Alzheimer's Immunotherapeutics (Abstract). Alzheimer's Association International Conference, Jul. 19, 2016.
Peng, Xubiao. et al. A Computational Method to Predict Disease-Specific Epitopes in Aβ, and Its Application to Oligomer-Selective Antibodies for Alzheimer's Immunotherapy (Poster). Alzheimer's Association International Conference. Jul. 21, 2016.
Peng, Xubiao. et al. A Computational Method to Predict Disease-Specific Epitopes in Aβ, and Its Application to Oligomer-Selective Antibodies for Alzheimer's Immunotherapy (Abstract). Alzheimer's Association International Conference. Jul. 21, 2016.
Gibbs, Ebrima et a. Rational generation of Aβ oligomer-specific antibodies through computational identification of conformational epitopes (Poster/Presentation). 13th International Conference on Alzheimer's & Parkinson's, Apr. 2017.
Gibbs, Ebrima et a. Rational generation of Aβ oligomer-specific antibodies through computational identification of conformational epitopes (Abstract). 13th International Conference on Alzheimer's & Parkinson's, Apr. 2017.
Peng, Xubiao et al. A Computational Method to Predict Disease-Specific Epitopes in Aβ peptide, and Its Application to Oligomer-Selective Antibodies for Alzheimer's Immunotherapy (Poster). Canadian Consortium for Neurodegeneration and Aging (CCNA), Oct. 6, 2016.
Zola, Stuart M. et al. "A Behavioral Task Predicts Conversion to Mild Cognitive Impairment and Alzheimer's Disease." American Journal of Alzheimer's Disease & Other Dementias. 28(2) 179-184 (2012).
Lu, J.X. et al. "Molecular Structure of Beta-Amyloid Fibrils in Alzheimer's Disease Brain Tissue" Cell vol. 154(6) p. 1257 (2013).
Xiao, Y. et al. A Beta (1-42) Fibril Structure Illuminates Self-Recognition and Replication of Amyloid in Alzheimer's Disease. Nat.Struct.Mol.Biol. vol. 22(6) p. 499-505 (2015).
Petkova, A.et al. Experimental Constraints on Quaternary Structure in Alzheimer's Beta-Amyloid Fibrils Biochemistry. vol. 45 p. 498 (2006).
Crespi, Gabriela A. N. et al. "Molecular basis for mid-region amyloid-b capture by leading Alzheimer's disease immunotherapies." Scientific Reports. 5 : 9649, 2015.
Hilser, Vincent J. et al. "Structure-based calculation of the equilibrium folding pathway of proteins. correlation with hydrogen exchange protection factors." J. Mol. Biol., 262:756-772, 1996.
Cohen, Samuel I. A. et al. Proliferation of amyloid-β42 aggregates occurs through a secondary nucleation mechanism. Proc. Natl.l Acad. Sci. USA, 110(24):9758-9763, 2013.
Sormanni, Pietro et al. The camsol method of rational design of protein mutants with enhanced solubility. Journal of Molecular Biology, 427(2):478-490, 2015.
Blacker, Deborah et al. Reliability and Validity of NINCDS-ADRDA Criteria for Alzheimer's Disease The National Institute of Mental Health Genetics Initiative. Arch Neurol. 51(12):1198-1204 (1994).
Hamley, I.W. "PEG-Peptide Conjugates" 2014; 15, 1543-1559; dx.doi.org/10.1021/bm500246w.
Roberts, MJ. et al. "Chemistry for peptide and protein PEGylation" 64: 116-127.
Karlin, Samuel et al. Methods for assessing the statistical significance of molecular sequence features by using general scoring schemes. Proc. Natl. Acad. Sci. U.S.A. 87:2264-2268.
Karlin, Samuel et al. Applications and statistics for multiple high-scoring segments in molecular sequences. 1993, Proc. Natl. Acad. Sci. U.S.A. 90:5873-5877.
Altschul et al. Basic Local Alignment Search Tool. 1990, J. Mol. Biol. 215:403.

Altschul et al. Gapped BLAST and PSI-BLAST: a new generation of protein database search programs. 1997, Nucleic Acids Res. 25:3389-3402.
Myers et al. Optimal alignments in linear space. 1988, CABIOS 4:11-17.
Kohler G. et al. Continuous cultures of fused cells secreting antibody of predefined specificity. Nature 256:495-497, 1975.
Ward et al. Binding activities of a repertoire of single immunoglobulin variable domains secreted from *Escherichia coli*. Nature 41:544-546 1989.
Riechmann et al. Reshaping human antibodies for therapy. Nature, 332:323-327, 1988.
Yu YZ, et al. Strikingly reduced amyloid burden and improved behavioral performance in Alzheimer's disease mice immunized with recombinant chimeric vaccines by hexavalent foldable A_1-15 fused to toxin-derived carrier proteins. J Alzheimers Dis 2014;41:243-60.
Wang, HC, et al. Peripherally administered sera antibodies recognizing amyloid-beta oligomers mitigate Alzheimer's disease-like pathology and cognitive decline in aged 3× Tg-AD mice, Vaccine 2016.
Paganetti PA et al. Amyloid precursor protein truncated at any of the γ-secretase sites is not cleaved to β-amyloid, J.Neurosci. Res. 46 (1996) 283-293.
Kahlert H. et al. Characterization of major allergens of Parietaria officinalis. Int Arch Allergy Immunol Feb. 1996; 109(2):141-9.
NCBI Blast: Protein Sequence (8 letters). CDR-H1 GYSFTSYW. Retrieved on Feb. 8, 2017 from blast.ncbi.nlm.nih.gov/Blast.cgi>>.
NCBI Blast: Protein Sequence (9 letters). CDR-H2 VHPGRGVST. Retrieved on Feb. 8, 2017 from <<blast.ncbi.nlm.nih.gov/Blast.cgi>>.
NCBI Blast: Protein Sequence (13 letters). CDR-H3 SRSHGNTYWFFDV. Retrieved on Feb. 8, 2017 from <<blast.ncbi.nlm.nih.gov/Blast.cgi>>.
NCBI Blast: Protein Sequence (11 letters). CDR-L1 QSIVHSNGNTY. Retrieved on Feb. 8, 2017 from blast.ncbi.nlm.nih.gov/Blast.cgi>>.
NCBI Blast: Protein Sequence (3 letters). CDR-L2 KVS. Retrieved on Feb. 8, 2017 from <blast.ncbi.nlm.nih.gov/Blast.cgi>>.
NCBI Blast: Protein Sequence (9 letters). CDR-L3 FQGSHVPFT. Retrieved on Feb. 8, 2017 from <blast.ncbi.nlm.nih.gov/Blast.cgi>>156622.
Tjernberg L.O., et al. Arrest of Amyloid Fibril Formation by a Pentapeptide Ligand. The Journal of Biological Chemistry. vol. 271, No. 15, Issue of Apr. 12, pp. 8545-8548, 1996.
Meek, Autumn R. et al. Searching for an endogenous anti-Alzheimer molecule: identifying small molecules in the brain that slow Alzheimer disease progression by inhibition of β-amyloid aggregation. J Psychiatry Neurosci 2013;38(4):269-75.
Hefti, Franz et al. The case for soluble Ab oligomers as a drug target in Alzheimer's disease. Trends in Pharmacological Sciences May 2013, vol. 34, No. 5, 261-266.
Adolfsson, Oskar et al. An Effector-Reduced Anti-β-Amyloid (Aβ) Antibody with Unique Aβ Binding Properties Promotes Neuroprotection and Glial Engulfment of Aβ. The Journal of Neuroscience, Jul. 11, 2012 • 32(28):9677-9689.
Sevigny, Jeff et al. The antibody aducanumab reduces Aβ plaques in Alzheimer's disease. Nature, vol. 537, Sep. 1, 2016.
Cleary, James P. et al. Natural oligomers of the amyloid-β protein specifically disrupt cognitive function. Nature Neuroscience, vol. 8, Issue 1, Jan. 2005, pp. 79-84.
Reed, Miranda N. et al. Cognitive effects of cell-derived and synthetically derived Aβ oligomers. Neurobiology of Aging 32 (2011) 1784-1794.
Freeman, Gary B. et al. Chronic Administration of an Aglycosylated Murine Antibody of Ponezumab Does Not Worsen Microhemorrhages in Aged Tg2576 Mice. Current Alzheimer Research, 2012, 9, 1059-1068.
Bohrmann, Bernd et al. Gantenerumab: A Novel Human Anti-Aβ Antibody Demonstrates Sustained Cerebral Amyloid-β Binding and Elicits Cell-Mediated Removal of Human Amyloid-β. Journal of Alzheimer's Disease 28 (2012) 49-69.

(56) References Cited

OTHER PUBLICATIONS

Tucker, Stina et al. The Murine Version of BAN2401 (mAb158) Selectively Reduces Amyloid-β Protofibrils in Brain and Cerebrospinal Fluid of tg-ArcSwe Mice. Journal of Alzheimer's Disease 43 (2015) 575-588.
Gardberg, Anna S. et al. Molecular basis for passive immunotherapy of Alzheimer's disease. PNAS, Oct. 2, 2017, vol. 104, No. 40, 15659-1564.
Imbimbo, Bruno P. et al. Solanezumab for the treatment of mild-to-moderate Alzheimer's disease. Expert Rev. Clin. Immunol. 8(2), 135-149 (2012).
Yang, Ting et al. Large Soluble Oligomers of Amyloid β-Protein from Alzheimer Brain Are Far Less Neuroactive Than the Smaller Oligomers to Which They Dissociate. The Journal of Neuroscience, Jan. 4, 2017, 37(1):152-163.
Dodart, Jean-Cosme et al. Immunization reverses memory deficits without reducing brain Aβ burden in Alzheimer's disease model. Nature Neuroscience, vol. 5, No. 5, May 2002, pp. 452-457.
Robert, Remy et al. Engineered antibody intervention strategies for Alzheimer's disease and related dementias by targeting amyloid and toxic oligomers. Protein Engineering, Design & Selection vol. 22 No. 3 pp. 199-208, 2009.
DeMattos, Ronald B. et al. A Plaque-Specific Antibody Clears Existing β-amyloid Plaques in Alzheimer's Disease Mice. Neuron 76, 908-920, Dec. 6, 2012.
Goure, William F. et al. Targeting the proper amyloid-beta neuronal toxins: a path forward for Alzheimer's disease immunotherapeutics. Alzheimer's Research & Therapy 2014, 6:42.
Carty, Niki C. et al. Intracranial administration of deglycosylated C-terminal-specific anti-Aβ antibody efficiently clears amyloid plaques without activating microglia in amyloid-depositing transgenic mice. Journal of Neuroinflammation 2006, 3:11.
Sengupta, Urmi et al. The Role of Amyloid-β Oligomers in Toxicity, Propagation, and Immunotherapy. EBioMedicine 6 (2016) 42-49.
Benilova, Iryna et al. The toxic Aβ oligomer and Alzheimer's disease: an emperor in need of clothes. Nature Neuroscience, vol. 15, No. 3, 349-357, Mar. 2012.
Antonios, Gregory et al. Alzheimer therapy with an antibody against N-terminal Abeta 4-X and pyroglutamate Abeta 3-X. Scientific Reports, 5:17338. Dec. 2015.
McLean, Catriona A. et al. Soluble Pool of Ab Amyloid as a Determinant of Severity of Neurodegeneration in Alzheimer's Disease. Ann Neurol 1999;46:860-866.
Balducci, Claudia et al. Synthetic amyloid-β oligomers impair long-term memory independently of cellular prion protein. PNAS, Feb. 2, 2010, vol. 7, No. 5, 2295-2300.
Fuller, James P. et al. Comparing the efficacy and neuroinflammatory potential of three anti-abeta antibodies. Acta Neuropathol (2015) 130:699-711.
Busche, Marc Aurel et al. Decreased amyloid-β and increased neuronal hyperactivity by immunotherapy in Alzheimer's models. Nature Neuroscience, Nov. 9, 2015.
Anonymous: "Antitope—Antibody huminization", Mar. 9, 2016 (Mar. 9, 2016), XP055256546, Retrieved from the Internet: URL:http://www.antitope.com/antibody-humanization [retrieved on Mar. 9, 2016]. "AvantGen's Antibody Humanization and Discovery Technologies", AvantGen, Jul. 27, 2009 (Jul. 27, 2009), XP055127073.
Anonymous: "Antibody Humanization | Antibody Engineering", Mar. 9, 2016 (Mar. 9, 2016), XP055256758, Retrieved from the Internet: lakepharma.com/productlist.php?category=2&secondary=3 [retrieved on Mar. 9, 2016].
Panka D J et al: "Variable Region Framework Differences Result in Decreased or Increased Affinity of Variant Anti-Digoxin Antibodies", Proceedings of the National Academy of Sciences, National Academy of Sciences, US, vol. 85, No. 9, May 1, 1988 (May 1, 1988), pp. 3080-3084.
Stephen I. Rudnick et al: "Affinity and Avidity in Antibody-Based Tumor Targeting", Cancer Biotherapy & Radiopharmaceuticals, vol. 24, No. 2, Apr. 1, 2009 (Apr. 1, 2009), pp. 155-161.

Rudikoff et al., Single amino acid substitution altering antigen-binding specificity. Proc Natl Acad Sci USA 1982; 79:1979-1983.
MacCallum et al., Antibody-antigen Interactions: Contact Analysis and Binding Site Topography. J. Mol. Biol., 1996;262:732-745.
Pascalis et al., Grafting of "Abbreviated" Complementarity-Determining Regions Containing Specificity-Determining Regions Containing Specificity-Determining Residues Essential for Ligand Contact to Engineer a Less Immunogenic Humanized Monoclonal Antibody. The Journal of Immunology, 2002; 169: 3076-3084.
Casset et al., A peptide mimetic of an anti-CD4 monoclonal antibody by rational design. BBRC, 2003; 307:198-205.
Vajdos et al., Comprehensive Functional Maps of the Antigen-binding Site of an Anti-ErbB2 Antibody Obtained with Shotgun Scanning Mutagenesis. J. Mol. Med., 2002; 320: 415-428.
Holm et al., Functional mapping and single chain construction of the anti-cytokeratin 8 monoclonal antibody TS1. Mol. Immunol., 2007; 44: 1075-1084.
Chen et al., Selection and Analysis of an Optimized Anti-VEGF Antibody: Crystal Structure of an Affinity-matured Fab in Complex with Antigen. J. Mol. Bio., 1999; 293: 865-881.
Wu et al., Humanization of a Murine Monoclonal Antibody by Simultaneousl Optimization of Framework and CDR Residues. J. Mol. Biol.,1999; 294: 151-162.
Burgess et al., Possible Dissociation of the Heparin-binding and Mitogenic Activities of Heparin-binding (Acidic Fibroblast) Growth Factor-1 from its Receptor-binding Activities by Site-directed Mutagenesis of a Single Lysine Residue. J of Cell Bio. 1990, 111:2129-2138.
Bowie et al., Deciphering the Message in Protein Sequences: Tikerance to Amino Acid Substitutions. Science, 1990, 247:1306-1310.
Pawson et al., Assembly of Cell Regulatory Systems Through Protein Interaction Domains. Science, 2003, 300:445-452.
Alaoui-Ismaili et al., Design of second generation therapeutic recombinant bone morphogenetic proteins. Cytokine Growth Factor Rev. 2009; 20:501-507.
Guo et al., Protein tolerance to random amino acid change. PNAS 2004; 101:9205-9210.
Gibbs, E. et al. Rational Generation of Aβ oligomer-specific antibodies through computational identification of conformational epitopes, Mar. 2017, Abstract from Neurodegenerative Diseases, vol. 17, Supplement 1.
Gibbs, E. et al. Rational Generation of Aβ oligomer-specific antibodies through computational identification of conformational epitopes, Apr. 22-28, 2017, Poster Presentation AAN 2017 Annual Meeting in Boston Massachusetts.
Plotkin, S. et al. Achieving the optimal profile for Alzheimer's immunotherapy: Rational generation of antibodies specific for toxic Aβ oligomers (P6.084), Apr. 17, 2017, Poster from Neurology, vol. 88, 16 Supplement; P6.084.
Kaplan, J. et al. Targeting of Toxic Amyloid-Beta Oligomer Species by Monoclonal Antibody PMN310: Precision Drug Design for Alzheimer's Disease, 2017, Abstract from Alzheimer's & Dementia. 13. P592. 10.1016/j.jalz.2017.07.225.
Cashman, N. Translating the Disruptive Science of Protein Misfolding to Neurodegenerative Disease, Sep. 28, 2017, Neurosciences, Oral Presentation.
Tjernberg L.O. et al. "Assembling amyloid fibrils from designed structures containing a significant amyloid B-peptide fragment", Biochem. J. (2002) 366: 343-351.
CAS RN 1347591-03-0, STN Entry Date Dec. 2, 2011.
CA RN 176390-22-0, STN Entry Date May 17, 1996.
CAS RN 176390-11-7, STN Entry Date May 17, 1996.
Ghosh, A. K. and Osswald, H. L., "BACE1 (B-Secretase) Inhibitors for the Treatment of Alzheimer's Disease", Chem Soc Rev. Oct. 7, 2014; 43(19): 6765-6813.
Walsh D. M. and Selkoe D. J., "AB Oligomers—a decade of discovery", Journal of Neurochemistry, 2007, 101, 1172-1184.
Hefti, F. et al. "The case for soluble AB oligomers as a drug target in Alzheimer's disease", Trends in Pharmacological Sciences, May 2013, vol. 34, No. 5, 261-266.
Neves V. et al. "Antibody approaches to treat brain illnesses", Trends in Biotechnology, 2015, 1-31.

(56) References Cited

OTHER PUBLICATIONS

Birks, J. "Cholinesterase inhibitors for Alzheimer's disease", Cochrane Database Syst Rev. Jan. 25, 2006; (1):CD005593.

Roy, Samir Sudhir. Designing Novel Peptidic Inhibitors of Beta Amyloid Oligomerization. PhD Disertation, Department of Chemistry, University of Calgary, 2010.

Simms, Gordon A. The Discovery of a Novel Series of Amyloid-Beta Antiaggregants Based on the Structure of 3-Hydroxyanthranilic Acid: A Detailed Analysis of the Mechanism of Action Underpinning Antiaggregant Activity. PhD Dissertation, Dalhousie University, Apr. 2015.

Nelson, Aaron L. Antiboy fragments. mAbs. Feb. 2010. Vol. 2, pp. 77-83.

Heinz Hillen et al. Generation and Therapeutic Efficacy of Highly Oligomer-Specific beta-Amyloid Antibodies. The Journal of Neuroscience, Society for Neuroscience, US vol. 30, No. 31, Aug. 4, 2010, pp. 10369-10379.

Janda, Alena et al. Ig Constant Region Effects on Variable Region Structure and Function. Frontiers in Microbiology, vol. 7, article 22, 2016.

\* cited by examiner

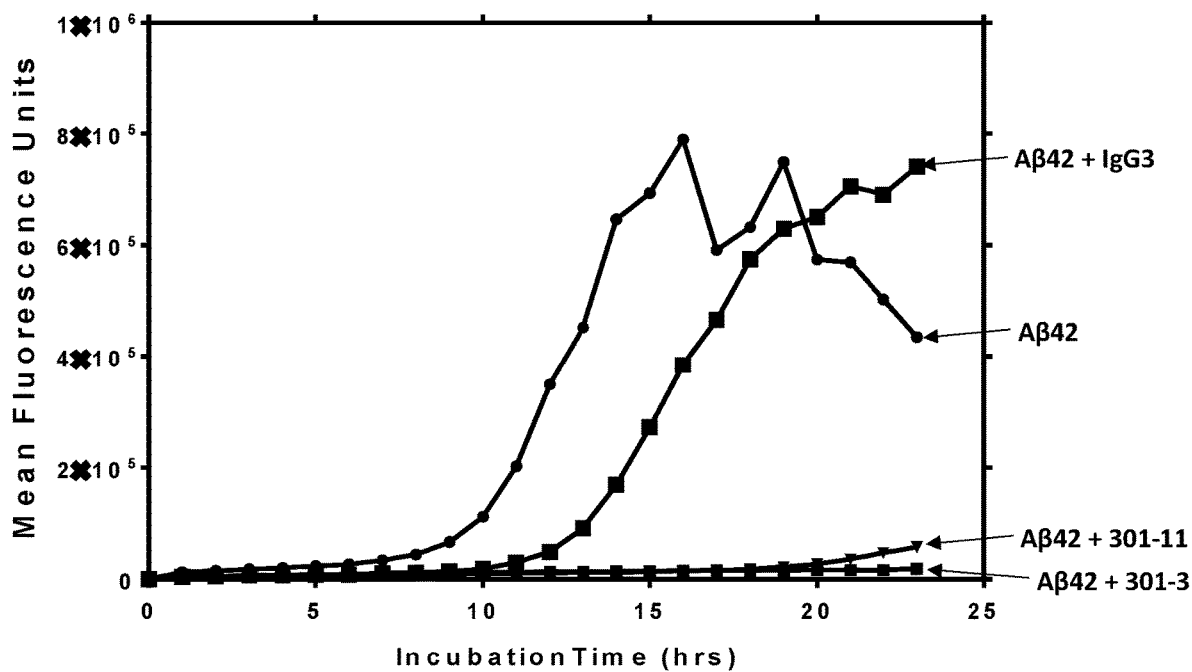

SEQUENCE LISTING

```
<160> NUMBER OF SEQ ID NOS: 101

<210> SEQ ID NO 1
<211> LENGTH: 8
<212> TYPE: PRT
<213> ORGANISM: Mus Musculus

<400> SEQUENCE: 1

Gly Phe Thr Phe Ser Asp Tyr Tyr
1               5

<210> SEQ ID NO 2
<211> LENGTH: 8
<212> TYPE: PRT
<213> ORGANISM: Mus Musculus

<400> SEQUENCE: 2

Ile Ser Asp Gly Gly Ser Tyr Thr
1               5

<210> SEQ ID NO 3
<211> LENGTH: 16
<212> TYPE: PRT
<213> ORGANISM: Mus Musculus

<400> SEQUENCE: 3

Ala Arg Asp Tyr Tyr Gly Ser Ser Ser Tyr Thr Ser Gly Phe Ala Tyr
1               5                   10                  15

<210> SEQ ID NO 4
<211> LENGTH: 12
<212> TYPE: PRT
<213> ORGANISM: Mus Musculus

<400> SEQUENCE: 4

Gln Ser Leu Leu Asn Ser Arg Thr Arg Lys Asn Tyr
1               5                   10

<210> SEQ ID NO 5
<211> LENGTH: 3
<212> TYPE: PRT
<213> ORGANISM: Mus Musculus

<400> SEQUENCE: 5

Trp Ala Ser
1

<210> SEQ ID NO 6
<211> LENGTH: 8
<212> TYPE: PRT
<213> ORGANISM: Mus Musculus

<400> SEQUENCE: 6

Lys Gln Ser Tyr Asn Leu Tyr Thr
1               5
```

<210> SEQ ID NO 7
<211> LENGTH: 4
<212> TYPE: PRT
<213> ORGANISM: Homo Sapiens

<400> SEQUENCE: 7

His His Gln Lys
1

<210> SEQ ID NO 8
<211> LENGTH: 426
<212> TYPE: DNA
<213> ORGANISM: Mus Musculus

<400> SEQUENCE: 8

```
atgaactttg ggctcagctt gattttcctt gtccttgttt taaaaggtgt ccagtgtgaa      60
gtgcagctgg tggagtctgg gggaggctta gtgaagcctg agggtccct gaaactctcc     120
tgtgcagcct ctggattcac tttcagtgac tattacatgt attgggttcg ccagactccg     180
gaaaagaggc tggagtgggt cgcaaccatt agtgatggtg gtagttacac ctcctatcca     240
gacagtgtga aggacgatt caccatctcc agagacaatg ccaagaacaa cctgtacctg     300
caaatgagca gtctgaggtc tgaggacaca gccatgtatt actgtgcaag agattactac     360
ggtagtagta gctacacctc gggctttgct tactggggcc aagggactct ggtcactgtc     420
tctgca                                                                 426
```

<210> SEQ ID NO 9
<211> LENGTH: 142
<212> TYPE: PRT
<213> ORGANISM: Mus Musculus

<400> SEQUENCE: 9

Met Asn Phe Gly Leu Ser Leu Ile Phe Leu Val Leu Val Leu Lys Gly
1               5                   10                  15

Val Gln Cys Glu Val Gln Leu Val Glu Ser Gly Gly Gly Leu Val Lys
                20                  25                  30

Pro Gly Gly Ser Leu Lys Leu Ser Cys Ala Ala Ser Gly Phe Thr Phe
            35                  40                  45

Ser Asp Tyr Tyr Met Tyr Trp Val Arg Gln Thr Pro Glu Lys Arg Leu
        50                  55                  60

Glu Trp Val Ala Thr Ile Ser Asp Gly Gly Ser Tyr Thr Ser Tyr Pro
65                  70                  75                  80

Asp Ser Val Lys Gly Arg Phe Thr Ile Ser Arg Asp Asn Ala Lys Asn
                85                  90                  95

Asn Leu Tyr Leu Gln Met Ser Ser Leu Arg Ser Glu Asp Thr Ala Met
            100                 105                 110

Tyr Tyr Cys Ala Arg Asp Tyr Tyr Gly Ser Ser Ser Tyr Thr Ser Gly
        115                 120                 125

Phe Ala Tyr Trp Gly Gln Gly Thr Leu Val Thr Val Ser Ala
    130                 135                 140

<210> SEQ ID NO 10
<211> LENGTH: 396
<212> TYPE: DNA
<213> ORGANISM: Mus Musculus

<400> SEQUENCE: 10

```
atggattcac aggcccaggt tcttatattg ctgctgctat gggtatctgg tacctgtggg      60
```

```
gacattgtga tgtcacagtc tccatcctcc ctggctgtgt caacaggaga gaaggtcact    120
atgagctgca aatccagtca gagtctgctc aacagtagaa cccgaaagaa ctacttggct    180
tggtaccagc agaaaccagg gcagtctcct aaactgctga tctactgggc atccactagg    240
gaatctgggg tccctgatcg cttcacaggc agtggatctg ggacagattt cactctcacc    300
atcagcagtg tgcaggctga agacctggca gtttattact gcaagcaatc ttataatctg    360
tacacgttcg gagggggac caagctggaa ataaaa                              396
```

<210> SEQ ID NO 11
<211> LENGTH: 132
<212> TYPE: PRT
<213> ORGANISM: Mus Musculus

<400> SEQUENCE: 11

```
Met Asp Ser Gln Ala Gln Val Leu Ile Leu Leu Leu Leu Trp Val Ser
1               5                   10                  15

Gly Thr Cys Gly Asp Ile Val Met Ser Gln Ser Pro Ser Ser Leu Ala
            20                  25                  30

Val Ser Thr Gly Glu Lys Val Thr Met Ser Cys Lys Ser Ser Gln Ser
        35                  40                  45

Leu Leu Asn Ser Arg Thr Arg Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys Lys Gln Ser Tyr Asn Leu Tyr Thr Phe Gly Gly Gly Thr Lys
        115                 120                 125

Leu Glu Ile Lys
    130
```

<210> SEQ ID NO 12
<211> LENGTH: 7
<212> TYPE: PRT
<213> ORGANISM: Artificial Sequence
<220> FEATURE:
<223> OTHER INFORMATION: Artificial Construct

<400> SEQUENCE: 12

```
Cys Gly His His Gln Lys Gly
1               5
```

<210> SEQ ID NO 13
<211> LENGTH: 366
<212> TYPE: DNA
<213> ORGANISM: Mus Musculus

<400> SEQUENCE: 13

```
caggtccaac tgcagcagcc tggggctgag cttgtgaagc ctggggcttc agtgaagatg    60
tcctgcaagg cttctggatt cactttcagt gactattaca taaactgggt gaagcagagg    120
cctggacaag gccttgagtg gattggagat attagtgatg gtggtagtta cacctacaat    180
gctaagttca agagcaaggc cacactgact ctggacacat cctccagcac agcctacatg    240
cagctcagca gcctgacatc tgaggactct gcggtctatt actgtgcaag agattactac    300
```

```
ggtagtagta gctacacctc gggctttgct tactggggcg caggcaccac ggtcaccgtc    360
tcctca                                                              366
```

<210> SEQ ID NO 14
<211> LENGTH: 122
<212> TYPE: PRT
<213> ORGANISM: Mus Musculus

<400> SEQUENCE: 14

Gln Val Gln Leu Gln Gln Pro Gly Ala Glu Leu Val Lys Pro Gly Ala
1               5                   10                  15

Ser Val Lys Met Ser Cys Lys Ala Ser Gly Phe Thr Phe Ser Asp Tyr
            20                  25                  30

Tyr Ile Asn Trp Val Lys Gln Arg Pro Gly Gln Gly Leu Glu Trp Ile
        35                  40                  45

Gly Asp Ile Ser Asp Gly Gly Ser Tyr Thr Tyr Asn Ala Lys Phe Lys
    50                  55                  60

Ser Lys Ala Thr Leu Thr Leu Asp Thr Ser Ser Thr Ala Tyr Met
65                  70                  75                  80

Gln Leu Ser Ser Leu Thr Ser Glu Asp Ser Ala Val Tyr Tyr Cys Ala
                85                  90                  95

Arg Asp Tyr Tyr Gly Ser Ser Tyr Thr Ser Gly Phe Ala Tyr Trp
            100                 105                 110

Gly Ala Gly Thr Thr Val Thr Val Ser Ser
        115                 120

<210> SEQ ID NO 15
<211> LENGTH: 366
<212> TYPE: DNA
<213> ORGANISM: Artificial Sequence
<220> FEATURE:
<223> OTHER INFORMATION: Synthetic Construct

<400> SEQUENCE: 15

```
caggtccaac tggtgcagtc tggggctgag cttaagaagc ctggggcttc agtgaagatg    60
tcctgcaagg cttctggatt cactttcagt gactattaca aaactgggt gaagcagagg    120 cctggacaag gccttgagtg gattggagat attagtgatg gtggtagtta cacctacaat    180
gctaagttca agagcagagc cacactgact ctggacacat ccataagcac agcctacatg    240
cagctcagca gcctgacatc tgaggactct gcggtctatt actgtgcaag agattactac    300
ggtagtagta gctacacctc gggctttgct tactggggcc aaggcaccac ggtcaccgtc    360
tcctca                                                              366
```

<210> SEQ ID NO 16
<211> LENGTH: 122
<212> TYPE: PRT
<213> ORGANISM: Artificial Sequence
<220> FEATURE:
<223> OTHER INFORMATION: Synthetic Construct

<400> SEQUENCE: 16

Gln Val Gln Leu Val Gln Ser Gly Ala Glu Leu Lys Lys Pro Gly Ala
1               5                   10                  15

Ser Val Lys Met Ser Cys Lys Ala Ser Gly Phe Thr Phe Ser Asp Tyr
            20                  25                  30

Tyr Ile Asn Trp Val Lys Gln Arg Pro Gly Gln Gly Leu Glu Trp Ile
        35                  40                  45

Gly Asp Ile Ser Asp Gly Gly Ser Tyr Thr Tyr Asn Ala Lys Phe Lys
            50                  55                  60

Ser Arg Ala Thr Leu Thr Leu Asp Thr Ser Ile Ser Thr Ala Tyr Met
 65                  70                  75                  80

Gln Leu Ser Ser Leu Thr Ser Glu Asp Ser Ala Val Tyr Tyr Cys Ala
                 85                  90                  95

Arg Asp Tyr Tyr Gly Ser Ser Tyr Thr Ser Gly Phe Ala Tyr Trp
            100                 105                 110

Gly Gln Gly Thr Thr Val Thr Val Ser Ser
            115                 120

<210> SEQ ID NO 17
<211> LENGTH: 366
<212> TYPE: DNA
<213> ORGANISM: Artificial Sequence
<220> FEATURE:
<223> OTHER INFORMATION: Synthetic Construct

<400> SEQUENCE: 17
caggtccaac tggtgcagtc tgggctgag gtgaagaagc ctggggcttc agtgaagatg     60
tcctgcaagg cttctggatt cactttcagt gactattaca aaactgggt gaagcagagg    120 cctggacaag gccttgagtg gattggagat attagtgatg gtggtagtta cacctacaat    180
gctaagttca agagcagagc cacactgact ctggacacat ccataagcac agcctacatg    240
gagctcagca gcctgagatc tgaggacacg gcggtctatt actgtgcaag agattactac    300
ggtagtagta gctacacctc gggctttgct tactggggcc aaggcaccac ggtcaccgtc    360
tcctca                                                               366

<210> SEQ ID NO 18
<211> LENGTH: 122
<212> TYPE: PRT
<213> ORGANISM: Artificial Sequence
<220> FEATURE:
<223> OTHER INFORMATION: Synthetic Construct

<400> SEQUENCE: 18

Gln Val Gln Leu Val Gln Ser Gly Ala Glu Val Lys Lys Pro Gly Ala
 1               5                  10                  15

Ser Val Lys Met Ser Cys Lys Ala Ser Gly Phe Thr Phe Ser Asp Tyr
            20                  25                  30

Tyr Ile Asn Trp Val Lys Gln Arg Pro Gly Gln Gly Leu Glu Trp Ile
            35                  40                  45

Gly Asp Ile Ser Asp Gly Gly Ser Tyr Thr Tyr Asn Ala Lys Phe Lys
            50                  55                  60

Ser Arg Ala Thr Leu Thr Leu Asp Thr Ser Ile Ser Thr Ala Tyr Met
 65                  70                  75                  80

Glu Leu Ser Ser Leu Arg Ser Glu Asp Thr Ala Val Tyr Tyr Cys Ala
                 85                  90                  95

Arg Asp Tyr Tyr Gly Ser Ser Tyr Thr Ser Gly Phe Ala Tyr Trp
            100                 105                 110

Gly Gln Gly Thr Thr Val Thr Val Ser Ser
            115                 120

<210> SEQ ID NO 19
<211> LENGTH: 366
<212> TYPE: DNA
<213> ORGANISM: Artificial Sequence
<220> FEATURE:

<223> OTHER INFORMATION: Synthetic Construct

<400> SEQUENCE: 19

```
caggtccaac tggtgcagtc tggggctgag gtgaagaagc ctggggcttc agtgaaggtg      60
tcctgcaagg cttctggatt cactttcagt gactattaca taaactgggt gcgacagagg     120
cctggacaag gccttgagtg gattggagat attagtgatg gtggtagtta cacctacaat     180
gctaagttca agagcagagc cacactgact ctggacacat ccataagcac agcctacatg     240
gagctcagca gcctgagatc tgaggacacg gcggtctatt actgtgcaag agattactac     300
ggtagtagta gctacacctc gggctttgct tactggggcc aaggcaccac ggtcaccgtc     360
tcctca                                                                366
```

<210> SEQ ID NO 20
<211> LENGTH: 122
<212> TYPE: PRT
<213> ORGANISM: Artificial Sequence
<220> FEATURE:
<223> OTHER INFORMATION: Synthetic Construct

<400> SEQUENCE: 20

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Asp Tyr
            20                  25                  30

Tyr Ile Asn Trp Val Arg Gln Arg Pro Gly Gln Gly Leu Glu Trp Ile
        35                  40                  45

Gly Asp Ile Ser Asp Gly Gly Ser Tyr Thr Tyr Asn Ala Lys Phe Lys
    50                  55                  60

Ser Arg Ala Thr Leu Thr Leu Asp Thr Ser Ile Ser Thr Ala Tyr Met
65                  70                  75                  80

Glu Leu Ser Ser Leu Arg Ser Glu Asp Thr Ala Val Tyr Tyr Cys Ala
                85                  90                  95

Arg Asp Tyr Tyr Gly Ser Ser Ser Tyr Thr Ser Gly Phe Ala Tyr Trp
            100                 105                 110

Gly Gln Gly Thr Thr Val Thr Val Ser Ser
        115                 120
```

<210> SEQ ID NO 21
<211> LENGTH: 366
<212> TYPE: DNA
<213> ORGANISM: Artificial Sequence
<220> FEATURE:
<223> OTHER INFORMATION: Synthetic Construct

<400> SEQUENCE: 21

```
caggtccaac tggtgcagtc tggggctgag gtgaagaagc ctggggcttc agtgaaggtg      60
tcctgcaagg cttctggatt cactttcagt gactattaca taaactgggt gcgacagagg     120
cctggacaag gccttgagtg gattggagat attagtgatg gtggtagtta cacctacaat     180
gctaagttca agagcagagt cacactgact ctggacacat ccataagcac agcctacatg     240
gagctcagca gcctgagatc tgaggacacg gcggtctatt actgtgcaag agattactac     300
ggtagtagta gctacacctc gggctttgct tactggggcc aaggcaccac ggtcaccgtc     360
tcctca                                                                366
```

<210> SEQ ID NO 22
<211> LENGTH: 122

```
<212> TYPE: PRT
<213> ORGANISM: Artificial Sequence
<220> FEATURE:
<223> OTHER INFORMATION: Synthetic Construct

<400> SEQUENCE: 22

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Asp Tyr
            20                  25                  30

Tyr Ile Asn Trp Val Arg Gln Arg Pro Gly Gln Gly Leu Glu Trp Ile
        35                  40                  45

Gly Asp Ile Ser Asp Gly Gly Ser Tyr Thr Tyr Asn Ala Lys Phe Lys
    50                  55                  60

Ser Arg Val Thr Leu Thr Leu Asp Thr Ser Ile Ser Thr Ala Tyr Met
65                  70                  75                  80

Glu Leu Ser Ser Leu Arg Ser Glu Asp Thr Ala Val Tyr Tyr Cys Ala
                85                  90                  95

Arg Asp Tyr Tyr Gly Ser Ser Tyr Thr Ser Gly Phe Ala Tyr Trp
            100                 105                 110

Gly Gln Gly Thr Thr Val Thr Val Ser Ser
        115                 120

<210> SEQ ID NO 23
<211> LENGTH: 366
<212> TYPE: DNA
<213> ORGANISM: Artificial Sequence
<220> FEATURE:
<223> OTHER INFORMATION: Synthetic Construct

<400> SEQUENCE: 23
caggtccaac tggtgcagtc tgggctgag gtgaagaagc tggggcttc agtgaaggtg      60 tcctgcaagg cttctggatt cactttcagt gactattaca taaactgggt gcgacagagg    120
cctggacaag gccttgagtg gatgggagat attagtgatg gtggtagtta cacctacaat    180
gctaagttca agagcagagt cacactgact agggacacat ccataagcac agcctacatg    240
gagctcagca gcctgagatc tgaggacacg gcggtctatt actgtgcaag agattactac    300
ggtagtagta gctacaccte gggctttgct tactggggcc aaggcaccac ggtcaccgtc    360
tcctca                                                                366

<210> SEQ ID NO 24
<211> LENGTH: 122
<212> TYPE: PRT
<213> ORGANISM: Artificial Sequence
<220> FEATURE:
<223> OTHER INFORMATION: Synthetic Construct

<400> SEQUENCE: 24

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Asp Tyr
            20                  25                  30

Tyr Ile Asn Trp Val Arg Gln Arg Pro Gly Gln Gly Leu Glu Trp Met
        35                  40                  45

Gly Asp Ile Ser Asp Gly Gly Ser Tyr Thr Tyr Asn Ala Lys Phe Lys
    50                  55                  60

Ser Arg Val Thr Leu Thr Arg Asp Thr Ser Ile Ser Thr Ala Tyr Met
65                  70                  75                  80
```

Glu Leu Ser Ser Leu Arg Ser Glu Asp Thr Ala Val Tyr Tyr Cys Ala
                85                  90                  95

Arg Asp Tyr Tyr Gly Ser Ser Tyr Thr Ser Gly Phe Ala Tyr Trp
            100                 105                 110

Gly Gln Gly Thr Thr Val Thr Val Ser Ser
        115                 120

<210> SEQ ID NO 25
<211> LENGTH: 366
<212> TYPE: DNA
<213> ORGANISM: Artificial Sequence
<220> FEATURE:
<223> OTHER INFORMATION: Synthetic Construct

<400> SEQUENCE: 25
caggtccaac tggtgcagtc tggggctgag gtgaagaagc ctggggcttc agtgaaggtg      60
tcctgcaagg cttctggatt cactttcagt gactattaca aaactgggt gcgacagagg     120 cctggacaag gccttgagtg gatgggagat attagtgatg gtggtagtta cacctacaat    180
gctaagttcc agggcagagt cacaatgact aggacacat ccataagcac agcctacatg     240
gagctcagca gcctgagatc tgaggacacg gcggtctatt actgtgcaag agattactac    300
ggtagtagta gctacaccctc gggctttgct tactggggcc aaggcaccac ggtcaccgtc   360
tcctca                                                                366

<210> SEQ ID NO 26
<211> LENGTH: 122
<212> TYPE: PRT
<213> ORGANISM: Artificial Sequence
<220> FEATURE:
<223> OTHER INFORMATION: Synthetic Construct

<400> SEQUENCE: 26

Gln Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Ser Asp Tyr
            20                  25                  30

Tyr Ile Asn Trp Val Arg Gln Arg Pro Gly Gln Gly Leu Glu Trp Met
        35                  40                  45

Gly Asp Ile Ser Asp Gly Gly Ser Tyr Thr Tyr Asn Ala Lys Phe Gln
    50                  55                  60

Gly Arg Val Thr Met Thr Arg Asp Thr Ser Ile Ser Thr Ala Tyr Met
65                  70                  75                  80

Glu Leu Ser Ser Leu Arg Ser Glu Asp Thr Ala Val Tyr Tyr Cys Ala
                85                  90                  95

Arg Asp Tyr Tyr Gly Ser Ser Tyr Thr Ser Gly Phe Ala Tyr Trp
            100                 105                 110

Gly Gln Gly Thr Thr Val Thr Val Ser Ser
        115                 120

<210> SEQ ID NO 27
<211> LENGTH: 336
<212> TYPE: DNA
<213> ORGANISM: Mus Musculus

<400> SEQUENCE: 27
gatgttttga tgacccaaac tccactctcc ctgcctgtca gtcttggaga tcaagcctcc      60
atctcttgca gatctagtca gagtctgctc aacagtagaa cccgaaagaa ctacttagaa    120
tggtacctgc agaaaccagg ccagtctcca aagctcctga tctactgggc atccaaccga    180
ttttctgggg tcccagacag gttcagtggc agtggatcag ggacagattt cacactcaag    240
atcagcagag tggaggctga ggatctggga gtttattact gcaagcaatc ttataatctg    300
tacacgtttg gcagcgggac caagctggag atcaaa                              336

<210> SEQ ID NO 28
<211> LENGTH: 112
<212> TYPE: PRT
<213> ORGANISM: Mus Musculus

<400> SEQUENCE: 28

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Leu Leu Asn Ser
            20                  25                  30

Arg Thr Arg Lys Asn Tyr Leu Glu Trp Tyr Leu Gln Lys Pro Gly Gln
        35                  40                  45

Ser Pro Lys Leu Leu Ile Tyr Trp Ala Ser Asn Arg Phe Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Leu Gly Val Tyr Tyr Cys Lys Gln
                85                  90                  95

Ser Tyr Asn Leu Tyr Thr Phe Gly Ser Gly Thr Lys Leu Glu Ile Lys
            100                 105                 110

<210> SEQ ID NO 29
<211> LENGTH: 336
<212> TYPE: DNA
<213> ORGANISM: Artificial Sequence
<220> FEATURE:
<223> OTHER INFORMATION: Synthetic Construct

<400> SEQUENCE: 29
gatgttttga tgacccaatc tccactctcc ctgcctgtca cccttggaca gccggcctcc     60
atctcttgca gatctagtca gagtctgctc aacagtagaa cccgaaagaa ctacttagaa    120
tggtttcagc agaaaccagg ccagtctcca aggcgcctga tctactgggc atccaaccga    180
ttttctgggg tcccagacag gttcagtggc agtggatcag ggacagattt cacactcaag    240
atcagcagag tggaggctga ggatgttgga gtttattact gcaagcaatc ttataatctg    300
tacacgtttg gccaagggac caagctggag atcaaa                              336

<210> SEQ ID NO 30
<211> LENGTH: 112
<212> TYPE: PRT
<213> ORGANISM: Artificial Sequence
<220> FEATURE:
<223> OTHER INFORMATION: Synthetic Construct

<400> SEQUENCE: 30

Asp Val Leu Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asn Ser
            20                  25                  30

Arg Thr Arg Lys Asn Tyr Leu Glu Trp Phe Gln Gln Lys Pro Gly Gln
        35                  40                  45

```
Ser Pro Arg Arg Leu Ile Tyr Trp Ala Ser Asn Arg Phe Ser Gly Val
        50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Lys Gln
                 85                  90                  95

Ser Tyr Asn Leu Tyr Thr Phe Gly Gln Gly Thr Lys Leu Glu Ile Lys
            100                 105                 110
```

<210> SEQ ID NO 31
<211> LENGTH: 336
<212> TYPE: DNA
<213> ORGANISM: Artificial Sequence
<220> FEATURE:
<223> OTHER INFORMATION: Synthetic Construct

<400> SEQUENCE: 31

```
gatgttgtga tgacccaatc tccactctcc ctgcctgtca cccttggaca gccggcctcc    60
atctcttgca gatctagtca gagtctgctc aacagtagaa cccgaaagaa ctacttagaa   120
tggtttcagc agaaaccagg ccagtctcca aggcgcctga tctactgggc atccaaccga   180 tttctgggg tcccagacag gttcagtggc agtggatcag ggacagattt cacactcaag   240
atcagcagag tggaggctga ggatgttgga gtttattact gcaagcaatc ttataatctg   300
tacacgtttg gccagggac caagctggag atcaaa                              336
```

<210> SEQ ID NO 32
<211> LENGTH: 112
<212> TYPE: PRT
<213> ORGANISM: Artificial Sequence
<220> FEATURE:
<223> OTHER INFORMATION: Synthetic Construct

<400> SEQUENCE: 32

```
Asp Val Val Met Thr Gln Ser Pro Leu Ser Leu Pro Val Thr Leu Gly
  1               5                  10                  15

Gln Pro Ala Ser Ile Ser Cys Arg Ser Ser Gln Ser Leu Leu Asn Ser
             20                  25                  30

Arg Thr Arg Lys Asn Tyr Leu Glu Trp Phe Gln Gln Lys Pro Gly Gln
         35                  40                  45

Ser Pro Arg Arg Leu Ile Tyr Trp Ala Ser Asn Arg Phe Ser Gly Val
    50                   55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Lys Gln
                 85                  90                  95

Ser Tyr Asn Leu Tyr Thr Phe Gly Gln Gly Thr Lys Leu Glu Ile Lys
            100                 105                 110
```

<210> SEQ ID NO 33
<211> LENGTH: 336
<212> TYPE: DNA
<213> ORGANISM: Artificial Sequence
<220> FEATURE:
<223> OTHER INFORMATION: Synthetic Construct

<400> SEQUENCE: 33

```
gatgttgtga tgacccaatc tccactctcc ctgcctgtca cccttggaca gccggcctcc    60
atctcttgca gatctagtca gagtctgctc aacagtagaa cccgaaagaa ctacttagaa   120
```

```
tggtttcagc agaggccagg ccagtctcca aggcgcctga tctactgggc atccaaccga    180
ttttctgggg tcccagacag gttcagtggc agtggatcag ggacagattt cacactcaag    240
atcagcagag tggaggctga ggatgttgga gtttattact gcaagcaatc ttataatctg    300
tacacgtttg gccagggac caagctggag atcaaa                               336
```

<210> SEQ ID NO 34
<211> LENGTH: 112
<212> TYPE: PRT
<213> ORGANISM: Artificial Sequence
<220> FEATURE:
<223> OTHER INFORMATION: Synthetic Construct

<400> SEQUENCE: 34

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asn Ser
            20                  25                  30

Arg Thr Arg Lys Asn Tyr Leu Glu Trp Phe Gln Arg Pro Gly Gln
        35                  40                  45

Ser Pro Arg Arg Leu Ile Tyr Trp Ala Ser Asn Arg Phe Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Lys Gln
                85                  90                  95

Ser Tyr Asn Leu Tyr Thr Phe Gly Gln Gly Thr Lys Leu Glu Ile Lys
            100                 105                 110
```

<210> SEQ ID NO 35
<211> LENGTH: 336
<212> TYPE: DNA
<213> ORGANISM: Artificial Sequence
<220> FEATURE:
<223> OTHER INFORMATION: Synthetic Construct

<400> SEQUENCE: 35

```
gatgttctga tgacccaatc tccactctcc ctgcctgtca cccttggaca gccggcctcc     60
atctcttgca gatctagtca gagtctgctc aacagtagaa cccgaaagaa ctacttagaa    120
tggtacctgc agaggccagg ccagtctcca aagctgctga tctactgggc atccaaccga    180
ttttctgggg tcccagacag gttcagtggc agtggatcag ggacagattt cacactcaag    240
atcagcagag tggaggctga ggatgttgga gtttattact gcaagcaatc ttataatctg    300
tacacgtttg gccagggac caagctggag atcaaa                               336
```

<210> SEQ ID NO 36
<211> LENGTH: 112
<212> TYPE: PRT
<213> ORGANISM: Artificial Sequence
<220> FEATURE:
<223> OTHER INFORMATION: Synthetic Construct

<400> SEQUENCE: 36

```
Asp Val Leu Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asn Ser
            20                  25                  30

Arg Thr Arg Lys Asn Tyr Leu Glu Trp Tyr Leu Gln Arg Pro Gly Gln
        35                  40                  45
```

```
Ser Pro Lys Leu Leu Ile Tyr Trp Ala Ser Asn Arg Phe Ser Gly Val
         50                  55                  60

Pro Asp Arg Phe Ser Gly Ser Gly Ser Gly Thr Asp Phe Thr Leu Lys
 65              70                  75                  80

Ile Ser Arg Val Glu Ala Glu Asp Val Gly Val Tyr Tyr Cys Lys Gln
                 85                  90                  95

Ser Tyr Asn Leu Tyr Thr Phe Gly Gln Gly Thr Lys Leu Glu Ile Lys
            100                 105                 110
```

<210> SEQ ID NO 37
<211> LENGTH: 336
<212> TYPE: DNA
<213> ORGANISM: Artificial Sequence
<220> FEATURE:
<223> OTHER INFORMATION: Synthetic Construct

<400> SEQUENCE: 37

```
gatgttctga tgacccaatc tccactctcc ctgcctgtca cccttggaca gccggcctcc      60
atctcttgca gatctagtca gagtctgctc aacagtagaa cccgaaagaa ctacttagaa     120
tggtaccagc agaggccagg ccagtctcca aggctgctga tctactgggc atccaaccga     180
ttttctgggg tcccagacag gttcagtggc agtggatcag ggacagattt cacactcaag     240
atcagcagag tggaggctga ggatgttgga gtttattact gcaagcaatc ttataatctg     300
tacacgtttg gccaagggac caagctggag atcaaa                               336
```

<210> SEQ ID NO 38
<211> LENGTH: 112
<212> TYPE: PRT
<213> ORGANISM: Artificial Sequence
<220> FEATURE:
<223> OTHER INFORMATION: Synthetic Construct

<400> SEQUENCE: 38

```
Asp Val Leu Met Thr Gln Ser Pro Leu Ser Leu Pro Val Thr Leu Gly
 1               5                  10                  15

Gln Pro Ala Ser Ile Ser Cys Arg Ser Ser Gln Ser Leu Leu Asn Ser
             20                  25                  30

Arg Thr Arg Lys Asn Tyr Leu Glu Trp Tyr Gln Gln Arg Pro Gly Gln
         35                  40                  45

Ser Pro Arg Leu Leu Ile Tyr Trp Ala Ser Asn Arg Phe Ser Gly Val
     50                  55                  60

Pro Asp Arg Phe Ser Gly Ser Gly Ser Gly Thr Asp Phe Thr Leu Lys
 65              70                  75                  80

Ile Ser Arg Val Glu Ala Glu Asp Val Gly Val Tyr Tyr Cys Lys Gln
                 85                  90                  95

Ser Tyr Asn Leu Tyr Thr Phe Gly Gln Gly Thr Lys Leu Glu Ile Lys
            100                 105                 110
```

<210> SEQ ID NO 39
<211> LENGTH: 336
<212> TYPE: DNA
<213> ORGANISM: Artificial Sequence
<220> FEATURE:
<223> OTHER INFORMATION: Synthetic Construct

<400> SEQUENCE: 39

```
gatgttgtga tgacccaatc tccactctcc ctgcctgtca cccttggaca gccggcctcc      60
atctcttgca gatctagtca gagtctgctc aacagtagaa cccgaaagaa ctacttagaa     120
```

```
tggtaccagc agaggccagg ccagtctcca aggctgctga tctactgggc atccaaccga    180
ttttctgggg tcccagacag gttcagtggc agtggatcag ggacagattt cacactcaag    240
atcagcagag tggaggctga ggatgttgga gtttattact gcaagcaatc ttataatctg    300
tacacgtttg gccaagggac caagctggag atcaaa                              336
```

<210> SEQ ID NO 40
<211> LENGTH: 112
<212> TYPE: PRT
<213> ORGANISM: Artificial Sequence
<220> FEATURE:
<223> OTHER INFORMATION: Synthetic Construct

<400> SEQUENCE: 40

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asn Ser
            20                  25                  30

Arg Thr Arg Lys Asn Tyr Leu Glu Trp Tyr Gln Gln Arg Pro Gly Gln
        35                  40                  45

Ser Pro Arg Leu Leu Ile Tyr Trp Ala Ser Asn Arg Phe Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Lys Gln
                85                  90                  95

Ser Tyr Asn Leu Tyr Thr Phe Gly Gln Gly Thr Lys Leu Glu Ile Lys
            100                 105                 110
```

<210> SEQ ID NO 41
<211> LENGTH: 360
<212> TYPE: DNA
<213> ORGANISM: Mus Musculus

<400> SEQUENCE: 41

```
caggtccaac tgcagcagcc tggggctgag cttgtgaagc ctggggcttc agtgaagatg    60
tcctgcaagg cttctggcta cagcttcacc agctactgga taaactgggt gaagcagagg   120
cctggacaag gccttgagtg gattggagat gtgcatcctg gtagaggcgt gtccacatac   180
aatgctaagt tcaagagcaa ggccacactg actctggaca tcctccag cacagcctac     240 atgcagctca gcagcctgac atctgaggac tctgcggtct attactgtag cagatcccat   300
ggtaacacct actggttttt tgacgtctgg ggcgcaggca ccacggtcac cgtctcctca   360
```

<210> SEQ ID NO 42
<211> LENGTH: 120
<212> TYPE: PRT
<213> ORGANISM: Mus Musculus

<400> SEQUENCE: 42

```
Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Ser Phe Thr Ser Tyr
            20                  25                  30

Trp Ile Asn Trp Val Lys Gln Arg Pro Gly Gln Gly Leu Glu Trp Ile
        35                  40                  45

Gly Asp Val His Pro Gly Arg Gly Val Ser Thr Tyr Asn Ala Lys Phe
    50                  55                  60
```

```
Lys Ser Lys Ala Thr Leu Thr Leu Asp Thr Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ser Arg Ser His Gly Asn Thr Tyr Trp Phe Phe Asp Val Trp Gly Ala
            100                 105                 110

Gly Thr Thr Val Thr Val Ser Ser
        115                 120

<210> SEQ ID NO 43
<211> LENGTH: 360
<212> TYPE: DNA
<213> ORGANISM: Artificial Sequence
<220> FEATURE:
<223> OTHER INFORMATION: Synthetic Construct

<400> SEQUENCE: 43
caggtccaac tggtgcagtc tggggctgag cttaagaagc ctggggcttc agtgaagatg      60
tcctgcaagg cttctggcta cagcttcacc agctactgga taaactgggt gaagcagagg     120
cctggacaag gccttgagtg gattggagat gtgcatcctg gtagaggcgt gtccacatac     180
aatgctaagt tcaagagcag agccacactg actctggaca catccataag cacagcctac     240
atgcagctca gcagcctgac atctgaggac tctgcggtct attactgtag cagatcccat     300
ggtaacacct actggttttt tgacgtctgg ggccaaggca ccacggtcac cgtctcctca     360

<210> SEQ ID NO 44
<211> LENGTH: 120
<212> TYPE: PRT
<213> ORGANISM: Artificial Sequence
<220> FEATURE:
<223> OTHER INFORMATION: Synthetic Construct

<400> SEQUENCE: 44

Gln Val Gln Leu Val Gln Ser Gly Ala Glu Leu Lys Lys Pro Gly Ala
  1               5                  10                  15

Ser Val Lys Met Ser Cys Lys Ala Ser Gly Tyr Ser Phe Thr Ser Tyr
             20                  25                  30

Trp Ile Asn Trp Val Lys Gln Arg Pro Gly Gln Gly Leu Glu Trp Ile
         35                  40                  45

Gly Asp Val His Pro Gly Arg Gly Val Ser Thr Tyr Asn Ala Lys Phe
     50                  55                  60

Lys Ser Arg Ala Thr Leu Thr Leu Asp Thr Ser Ile Ser Thr Ala Tyr
 65                  70                  75                  80

Met Gln Leu Ser Ser Leu Thr Ser Glu Asp Ser Ala Val Tyr Tyr Cys
                 85                  90                  95

Ser Arg Ser His Gly Asn Thr Tyr Trp Phe Phe Asp Val Trp Gly Gln
            100                 105                 110

Gly Thr Thr Val Thr Val Ser Ser
        115                 120

<210> SEQ ID NO 45
<211> LENGTH: 360
<212> TYPE: DNA
<213> ORGANISM: Artificial Sequence
<220> FEATURE:
<223> OTHER INFORMATION: Synthetic Construct

<400> SEQUENCE: 45
```

```
caggtccaac tggtgcagtc tggggctgag gtgaagaagc tggggcttc agtgaagatg      60 tcctgcaagg cttctggcta cagcttcacc agctactgga taaactgggt gaagcagagg    120
cctggacaag gccttgagtg gattggagat gtgcatcctg gtagaggcgt gtccacatac    180
aatgctaagt tcaagagcag agccacactg actctggaca catccataag cacagcctac    240
atggagctca gcagcctgag atctgaggac acggcggtct attactgtag cagatcccat    300
ggtaacacct actggttttt tgacgtctgg ggccaaggca ccacggtcac cgtctcctca    360
```

<210> SEQ ID NO 46
<211> LENGTH: 120
<212> TYPE: PRT
<213> ORGANISM: Artificial Sequence
<220> FEATURE:
<223> OTHER INFORMATION: Synthetic Construct

<400> SEQUENCE: 46

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Ser Phe Thr Ser Tyr
            20                  25                  30

Trp Ile Asn Trp Val Lys Gln Arg Pro Gly Gln Gly Leu Glu Trp Ile
        35                  40                  45

Gly Asp Val His Pro Gly Arg Gly Val Ser Thr Tyr Asn Ala Lys Phe
    50                  55                  60

Lys Ser Arg Ala Thr Leu Thr Leu Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ser Arg Ser His Gly Asn Thr Tyr Trp Phe Phe Asp Val Trp Gly Gln
            100                 105                 110

Gly Thr Thr Val Thr Val Ser Ser
        115                 120

<210> SEQ ID NO 47
<211> LENGTH: 360
<212> TYPE: DNA
<213> ORGANISM: Artificial Sequence
<220> FEATURE:
<223> OTHER INFORMATION: Synthetic Construct

<400> SEQUENCE: 47

```
caggtccaac tggtgcagtc tggggctgag gtgaagaagc tggggcttc agtgaaggtg      60 tcctgcaagg cttctggcta cagcttcacc agctactgga taaactgggt gcgacagagg    120
cctggacaag gccttgagtg gattggagat gtgcatcctg gtagaggcgt gtccacatac    180
aatgctaagt tcaagagcag agccacactg actctggaca catccataag cacagcctac    240
atggagctca gcagcctgag atctgaggac acggcggtct attactgtag cagatcccat    300
ggtaacacct actggttttt tgacgtctgg ggccaaggca ccacggtcac cgtctcctca    360
```

<210> SEQ ID NO 48
<211> LENGTH: 120
<212> TYPE: PRT
<213> ORGANISM: Artificial Sequence
<220> FEATURE:
<223> OTHER INFORMATION: Synthetic Construct

<400> SEQUENCE: 48

Gln Val Gln Leu Val Gln Ser Gly Ala Glu Val Lys Lys Pro Gly Ala

```
1               5                   10                  15
Ser Val Lys Val Ser Cys Lys Ala Ser Gly Tyr Ser Phe Thr Ser Tyr
            20                  25                  30

Trp Ile Asn Trp Val Arg Gln Arg Pro Gly Gln Gly Leu Glu Trp Ile
            35                  40                  45

Gly Asp Val His Pro Gly Arg Gly Val Ser Thr Tyr Asn Ala Lys Phe
    50                  55                  60

Lys Ser Arg Ala Thr Leu Thr Leu Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ser Arg Ser His Gly Asn Thr Tyr Trp Phe Phe Asp Val Trp Gly Gln
            100                 105                 110

Gly Thr Thr Val Thr Val Ser Ser
            115                 120
```

<210> SEQ ID NO 49
<211> LENGTH: 360
<212> TYPE: DNA
<213> ORGANISM: Artificial Sequence
<220> FEATURE:
<223> OTHER INFORMATION: Synthetic Construct

<400> SEQUENCE: 49

```
caggtccaac tggtgcagtc tggggctgag gtgaagaagc ctggggcttc agtgaaggtg      60
tcctgcaagg cttctggcta cagcttcacc agctactgga taaactgggt gcgacagagg     120
cctggacaag gccttgagtg gattggagat gtgcatcctg gtagaggcgt gtccacatac     180
aatgctaagt tcaagagcag agtcacactg actctggaca catccataag cacagcctac     240
atggagctca gcagcctgag atctgaggac acggcggtct attactgtag cagatcccat     300
ggtaacacct actggttttt tgacgtctgg ggccaaggca ccacggtcac cgtctcctca     360
```

<210> SEQ ID NO 50
<211> LENGTH: 120
<212> TYPE: PRT
<213> ORGANISM: Artificial Sequence
<220> FEATURE:
<223> OTHER INFORMATION: Synthetic Construct

<400> SEQUENCE: 50

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Trp Ile Asn Trp Val Arg Gln Arg Pro Gly Gln Gly Leu Glu Trp Ile
            35                  40                  45

Gly Asp Val His Pro Gly Arg Gly Val Ser Thr Tyr Asn Ala Lys Phe
    50                  55                  60

Lys Ser Arg Val Thr Leu Thr Leu Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ser Arg Ser His Gly Asn Thr Tyr Trp Phe Phe Asp Val Trp Gly Gln
            100                 105                 110

Gly Thr Thr Val Thr Val Ser Ser
            115                 120
```

<210> SEQ ID NO 51
<211> LENGTH: 360
<212> TYPE: DNA
<213> ORGANISM: Artificial Sequence
<220> FEATURE:
<223> OTHER INFORMATION: Synthetic Construct

<400> SEQUENCE: 51

```
caggtccaac tggtgcagtc tggggctgag gtgaagaagc ctggggcttc agtgaaggtg    60
tcctgcaagg cttctggcta cagcttcacc agctactgga taaactgggt gcgacagagg   120
cctggacaag gccttgagtg gatgggagat gtgcatcctg gtagaggcgt gtccacatac   180
aatgctaagt tcaagagcag agtcacactg actagggaca catccataag cacagcctac   240
atggagctca gcagcctgag atctgaggac acggcggtct attactgtag cagatcccat   300
ggtaacacct actggttttt tgacgtctgg ggccaaggca ccacggtcac cgtctcctca   360
```

<210> SEQ ID NO 52
<211> LENGTH: 120
<212> TYPE: PRT
<213> ORGANISM: Artificial Sequence
<220> FEATURE:
<223> OTHER INFORMATION: Synthetic Construct

<400> SEQUENCE: 52

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Ser Phe Thr Ser Tyr
            20                  25                  30
Trp Ile Asn Trp Val Arg Gln Arg Pro Gly Gln Gly Leu Glu Trp Met
        35                  40                  45
Gly Asp Val His Pro Gly Arg Gly Val Ser Thr Tyr Asn Ala Lys Phe
    50                  55                  60
Lys Ser Arg Val Thr Leu Thr Arg Asp Thr Ser Ile Ser Thr Ala Tyr
65                  70                  75                  80
Met Glu Leu Ser Ser Leu Arg Ser Glu Asp Thr Ala Val Tyr Tyr Cys
                85                  90                  95
Ser Arg Ser His Gly Asn Thr Tyr Trp Phe Phe Asp Val Trp Gly Gln
            100                 105                 110
Gly Thr Thr Val Thr Val Ser Ser
        115                 120

<210> SEQ ID NO 53
<211> LENGTH: 360
<212> TYPE: DNA
<213> ORGANISM: Artificial Sequence
<220> FEATURE:
<223> OTHER INFORMATION: Synthetic Construct

<400> SEQUENCE: 53

```
caggtccaac tggtgcagtc tggggctgag gtgaagaagc ctggggcttc agtgaaggtg    60
tcctgcaagg cttctggcta cagcttcacc agctactgga taaactgggt gcgacagagg   120
cctggacaag gccttgagtg gatgggagat gtgcatcctg gtagaggcgt gtccacatac   180
aatgctaagt tccagggcag agtcacaatg actagggaca catccataag cacagcctac   240
atggagctca gcagcctgag atctgaggac acggcggtct attactgtag cagatcccat   300
ggtaacacct actggttttt tgacgtctgg ggccaaggca ccacggtcac cgtctcctca   360
```

-continued

<210> SEQ ID NO 54
<211> LENGTH: 120
<212> TYPE: PRT
<213> ORGANISM: Artificial Sequence
<220> FEATURE:
<223> OTHER INFORMATION: Synthetic Construct

<400> SEQUENCE: 54

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Trp Ile Asn Trp Val Arg Gln Arg Pro Gly Gln Gly Leu Glu Trp Met
        35                  40                  45

Gly Asp Val His Pro Gly Arg Gly Val Ser Thr Tyr Asn Ala Lys Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ser Arg Ser His Gly Asn Thr Tyr Trp Phe Phe Asp Val Trp Gly Gln
            100                 105                 110

Gly Thr Thr Val Thr Val Ser Ser
        115                 120

<210> SEQ ID NO 55
<211> LENGTH: 336
<212> TYPE: DNA
<213> ORGANISM: Mus Musculus

<400> SEQUENCE: 55
gatgttttga tgacccaaac tccactctcc ctgcctgtca gtcttggaga tcaagcctcc      60
atctcttgca gatctagtca gagcattgta catagtaatg aaacacccta tttagaatgg     120
tacctgcaga aaccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tattactgct ttcaaggttc acatgttcct     300 ttcactttg gcagcgggac caagctggag atcaaa                                336

<210> SEQ ID NO 56
<211> LENGTH: 112
<212> TYPE: PRT
<213> ORGANISM: Mus Musculus

<400> SEQUENCE: 56

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

```
Ser His Val Pro Phe Thr Phe Gly Ser Gly Thr Lys Leu Glu Ile Lys
            100                 105                 110
```

<210> SEQ ID NO 57
<211> LENGTH: 336
<212> TYPE: DNA
<213> ORGANISM: Artificial Sequence
<220> FEATURE:
<223> OTHER INFORMATION: Synthetic Construct

<400> SEQUENCE: 57

```
gatgttttga tgacccaatc tccactctcc ctgcctgtca cccttggaca gccggcctcc      60
atctcttgca gatctagtca gagcattgta catagtaatg gaaacaccta tttagaatgg     120
tttcagcaga aaccaggcca gtctccaagg cgcctgatct acaaagtttc caaccgattt     180
tctggggtcc cagacaggtt cagtggcagt ggatcaggga cagatttcac actcaagatc     240
agcagagtgg aggctgagga tgttggagtt tattactgct ttcaaggttc acatgttcct     300
ttcacttttg gccaagggac caagctggag atcaaa                              336
```

<210> SEQ ID NO 58
<211> LENGTH: 112
<212> TYPE: PRT
<213> ORGANISM: Artificial Sequence
<220> FEATURE:
<223> OTHER INFORMATION: Synthetic Construct

<400> SEQUENCE: 58

```
Asp Val Leu Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Gly Asn Thr Tyr Leu Glu Trp Phe Gln Gln Lys Pro Gly Gln Ser
        35                  40                  45

Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Phe Thr Phe Gly Gln Gly Thr Lys Leu Glu Ile Lys
            100                 105                 110
```

<210> SEQ ID NO 59
<211> LENGTH: 336
<212> TYPE: DNA
<213> ORGANISM: Artificial Sequence
<220> FEATURE:
<223> OTHER INFORMATION: Synthetic Construct

<400> SEQUENCE: 59

```
gatgttgtga tgacccaatc tccactctcc ctgcctgtca cccttggaca gccggcctcc      60
atctcttgca gatctagtca gagcattgta catagtaatg gaaacaccta tttagaatgg     120
tttcagcaga aaccaggcca gtctccaagg cgcctgatct acaaagtttc caaccgattt     180
tctggggtcc cagacaggtt cagtggcagt ggatcaggga cagatttcac actcaagatc     240
agcagagtgg aggctgagga tgttggagtt tattactgct ttcaaggttc acatgttcct     300
ttcacttttg gccaagggac caagctggag atcaaa                              336
```

-continued

<210> SEQ ID NO 60
<211> LENGTH: 112
<212> TYPE: PRT
<213> ORGANISM: Artificial Sequence
<220> FEATURE:
<223> OTHER INFORMATION: Synthetic Construct

<400> SEQUENCE: 60

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Gly Asn Thr Tyr Leu Glu Trp Phe Gln Gln Lys Pro Gly Gln Ser
        35                  40                  45

Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Phe Thr Phe Gly Gln Gly Thr Lys Leu Glu Ile Lys
            100                 105                 110

<210> SEQ ID NO 61
<211> LENGTH: 336
<212> TYPE: DNA
<213> ORGANISM: Artificial Sequence
<220> FEATURE:
<223> OTHER INFORMATION: Synthetic Construct

<400> SEQUENCE: 61
gatgttgtga tgacccaatc tccactctcc ctgcctgtca cccttggaca gccggcctcc      60
atctcttgca gatctagtca gagcattgta catagtaatg gaaacaccta tttagaatgg     120
tttcagcaga ggccaggcca gtctccaagg cgcctgatct acaaagtttc caaccgattt     180
tctggggtcc cagacaggtt cagtggcagt ggatcaggga cagatttcac actcaagatc     240
agcagagtgg aggctgagga tgttggagtt tattactgct ttcaaggttc acatgttcct     300
ttcacttttg gccaagggac caagctggag atcaaa                               336

<210> SEQ ID NO 62
<211> LENGTH: 112
<212> TYPE: PRT
<213> ORGANISM: Artificial Sequence
<220> FEATURE:
<223> OTHER INFORMATION: Synthetic Construct

<400> SEQUENCE: 62

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Gly Asn Thr Tyr Leu Glu Trp Phe Gln Gln Arg Pro Gly Gln Ser
        35                  40                  45

Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Phe Thr Phe Gly Gln Gly Thr Lys Leu Glu Ile Lys
            100                 105                 110

<210> SEQ ID NO 63
<211> LENGTH: 336
<212> TYPE: DNA
<213> ORGANISM: Artificial Sequence
<220> FEATURE:
<223> OTHER INFORMATION: Synthetic Construct

<400> SEQUENCE: 63
gatgttctga tgacccaatc tccactctcc ctgcctgtca cccttggaca gccggcctcc      60
atctcttgca gatctagtca gagcattgta catagtaatg gaaacaccta tttagaatgg     120
tacctgcaga ggccaggcca gtctccaaag ctgctgatct acaaagtttc caaccgattt     180
tctggggtcc cagacaggtt cagtggcagt ggatcaggga cagatttcac actcaagatc     240
agcagagtgg aggctgagga tgttggagtt tattactgct ttcaaggttc acatgttcct     300
ttcacttttg gccaagggac caagctggag atcaaa                               336

<210> SEQ ID NO 64
<211> LENGTH: 112
<212> TYPE: PRT
<213> ORGANISM: Artificial Sequence
<220> FEATURE:
<223> OTHER INFORMATION: Synthetic Construct

<400> SEQUENCE: 64

Asp Val Leu Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Gly Asn Thr Tyr Leu Glu Trp Tyr Leu Gln Arg Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Phe Thr Phe Gly Gln Gly Thr Lys Leu Glu Ile Lys
            100                 105                 110

<210> SEQ ID NO 65
<211> LENGTH: 336
<212> TYPE: DNA
<213> ORGANISM: Artificial Sequence
<220> FEATURE:
<223> OTHER INFORMATION: Synthetic Construct

<400> SEQUENCE: 65
gatgttctga tgacccaatc tccactctcc ctgcctgtca cccttggaca gccggcctcc      60
atctcttgca gatctagtca gagcattgta catagtaatg gaaacaccta tttagaatgg     120
taccagcaga ggccaggcca gtctccaagg ctgctgatct acaaagtttc caaccgattt     180
tctggggtcc cagacaggtt cagtggcagt ggatcaggga cagatttcac actcaagatc     240
agcagagtgg aggctgagga tgttggagtt tattactgct ttcaaggttc acatgttcct     300
ttcacttttg gccaagggac caagctggag atcaaa                               336

<210> SEQ ID NO 66
<211> LENGTH: 112
<212> TYPE: PRT
<213> ORGANISM: Artificial Sequence
<220> FEATURE:
<223> OTHER INFORMATION: Synthetic Construct

<400> SEQUENCE: 66

```
Asp Val Leu Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Gly Asn Thr Tyr Leu Glu Trp Tyr Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Phe Thr Phe Gly Gln Gly Thr Lys Leu Glu Ile Lys
            100                 105                 110
```

<210> SEQ ID NO 67
<211> LENGTH: 336
<212> TYPE: DNA
<213> ORGANISM: Artificial Sequence
<220> FEATURE:
<223> OTHER INFORMATION: Synthetic Construct

<400> SEQUENCE: 67

```
gatgttgtga tgacccaatc tccactctcc ctgcctgtca cccttggaca gccggcctcc      60
atctcttgca gatctagtca gagcattgta catagtaatg gaaacaccta tttagaatgg     120
taccagcaga ggccaggcca gtctccaagg ctgctgatct acaaagtttc caaccgattt     180
tctggggtcc cagacaggtt cagtggcagt ggatcaggga cagatttcac actcaagatc     240
agcagagtgg aggctgagga tgttggagtt tattactgct ttcaaggttc acatgttcct     300
ttcacttttg gccaagggac caagctggag atcaaa                               336
```

<210> SEQ ID NO 68
<211> LENGTH: 112
<212> TYPE: PRT
<213> ORGANISM: Artificial Sequence
<220> FEATURE:
<223> OTHER INFORMATION: Synthetic Construct

<400> SEQUENCE: 68

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Gly Asn Thr Tyr Leu Glu Trp Tyr Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
```

85                  90                  95
Ser His Val Pro Phe Thr Phe Gly Gln Gly Thr Lys Leu Glu Ile Lys
                100                 105                 110

<210> SEQ ID NO 69
<211> LENGTH: 984
<212> TYPE: DNA
<213> ORGANISM: Artificial Sequence
<220> FEATURE:
<223> OTHER INFORMATION: Synthetic Construct

<400> SEQUENCE: 69
gcttccacca agggcccatc cgtcttcccc ctggcgccct gctccaggag cacctccgag      60
agcacagccg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacgaagacc     240
tacacctgca atgtagatca caagcccagc aacaccaagg tggacaagag agttgagtcc     300
aaatatggtc ccccatgccc accatgccca gcacctgagt tcctgggggg accatcagtc     360
ttcctgttcc ccccaaaacc caaggacact ctcatgatct cccggacccc tgaggtcacg     420
tgcgtggtgg tggacgtgag ccaggaagac cccgaggtcc agttcaactg gtacgtggat     480
ggcgtggagg tgcataatgc caagacaaag ccgcgggagg agcagttcaa cagcacgtac     540
cgtgtggtca gcgtcctcac cgtcctgcac caggactggc tgaacggcaa ggagtacaag     600
tgcaaggtct ccaacaaagg cctcccgtcc tccatcgaga aaaccatctc aaaagccaaa     660
gggcagcccc gagagccaca ggtgtacacc ctgcccccat cccaggagga gatgaccaag     720
aaccaggtca gcctgacctg cctggtcaaa ggcttctacc ccagcgacat cgccgtggag     780
tgggagagca atgggcagcc ggagaacaac tacaagacca cgcctcccgt gctggactcc     840
gacggctcct tcttcctcta cagcaggcta accgtggaca agagcaggtg gcaggagggg     900
aatgtcttct catgctccgt gatgcatgag gctctgcaca accactacac acagaagagc     960
ctctccctgt ctctgggtaa atga                                            984

<210> SEQ ID NO 70
<211> LENGTH: 327
<212> TYPE: PRT
<213> ORGANISM: Artificial Sequence
<220> FEATURE:
<223> OTHER INFORMATION: Synthetic Construct

<400> SEQUENCE: 70

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
                100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 71
<211> LENGTH: 324
<212> TYPE: DNA
<213> ORGANISM: Artificial Sequence
<220> FEATURE:
<223> OTHER INFORMATION: Synthetic Construct

<400> SEQUENCE: 71
cgaactgtgg ctgcaccatc tgtcttcatc ttcccgccat ctgatgagca gttgaaatct     60
ggaactgcct ctgttgtgtg cctgctgaat aacttctatc ccagagaggc caaagtacag    120
tggaaggtgg ataacgccct ccaatcgggt aactcccagg agagtgtcac agagcaggac    180
agcaaggaca gcacctacag cctcagcagc accctgacgc tgagcaaagc agactacgag    240
aaacacaaag tctacgcctg cgaagtcacc catcagggcc tgagctcgcc cgtcacaaag    300
agcttcaaca ggggagagtg ttag                                           324

<210> SEQ ID NO 72
<211> LENGTH: 107
<212> TYPE: PRT
<213> ORGANISM: Artificial Sequence
<220> FEATURE:
<223> OTHER INFORMATION: Synthetic Construct

<400> SEQUENCE: 72

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe

-continued

```
                20                  25                  30
Tyr Pro Arg Glu Ala Lys Val Gln Trp Lys Val Asp Asn Ala Leu Gln
                35                  40                  45

Ser Gly Asn Ser Gln Glu Ser Val Thr Glu Gln Asp Ser Lys Asp Ser
            50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 73
<211> LENGTH: 42
<212> TYPE: PRT
<213> ORGANISM: Homo Sapiens

<400> SEQUENCE: 73

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
                20                  25                  30

Gly Leu Met Val Gly Gly Val Val Ile Ala
            35                  40

<210> SEQ ID NO 74
<211> LENGTH: 8
<212> TYPE: PRT
<213> ORGANISM: Mus Musculus

<400> SEQUENCE: 74

Gly Tyr Ser Phe Thr Ser Tyr Trp
1               5

<210> SEQ ID NO 75
<211> LENGTH: 9
<212> TYPE: PRT
<213> ORGANISM: Mus Musculus

<400> SEQUENCE: 75

Val His Pro Gly Arg Gly Val Ser Thr
1               5

<210> SEQ ID NO 76
<211> LENGTH: 13
<212> TYPE: PRT
<213> ORGANISM: Mus Musculus

<400> SEQUENCE: 76

Ser Arg Ser His Gly Asn Thr Tyr Trp Phe Phe Asp Val
1               5                   10

<210> SEQ ID NO 77
<211> LENGTH: 11
<212> TYPE: PRT
<213> ORGANISM: Mus Musculus

<400> SEQUENCE: 77

Gln Ser Ile Val His Ser Asn Gly Asn Thr Tyr
1               5                   10
```

```
<210> SEQ ID NO 78
<211> LENGTH: 3
<212> TYPE: PRT
<213> ORGANISM: Mus Musculus

<400> SEQUENCE: 78

Lys Val Ser
1

<210> SEQ ID NO 79
<211> LENGTH: 9
<212> TYPE: PRT
<213> ORGANISM: Mus Musculus

<400> SEQUENCE: 79

Phe Gln Gly Ser His Val Pro Phe Thr
1               5

<210> SEQ ID NO 80
<211> LENGTH: 16
<212> TYPE: PRT
<213> ORGANISM: Mus Musculus

<400> SEQUENCE: 80

Ala Arg Asp Tyr Tyr Gly Ser Asn Ser Tyr Thr Ser Gly Phe Ala Tyr
1               5                   10                  15

<210> SEQ ID NO 81
<211> LENGTH: 11
<212> TYPE: PRT
<213> ORGANISM: Mus Musculus

<400> SEQUENCE: 81

Gln Ser Ile Val His Ser Asn Gly Asn Thr Tyr
1               5                   10

<210> SEQ ID NO 82
<211> LENGTH: 3
<212> TYPE: PRT
<213> ORGANISM: Mus Musculus

<400> SEQUENCE: 82

Lys Val Ser
1

<210> SEQ ID NO 83
<211> LENGTH: 9
<212> TYPE: PRT
<213> ORGANISM: Mus Musculus

<400> SEQUENCE: 83

Phe Gln Gly Ser His Val Pro Leu Thr
1               5

<210> SEQ ID NO 84
<211> LENGTH: 426
<212> TYPE: DNA
<213> ORGANISM: Mus Musculus

<400> SEQUENCE: 84
atgaacttcg ggctcagctt gattttcctt gtccttgttt taaaaggtgt ccagtgtgaa      60
gtgcagctgg tggagtctgg gggaggctta gtgaagcctg agggtccct gaaactctcc      120 tgtgcagcct ctggattcac tttcagtgac tattacatgt attgggttcg ccagactccg      180
```

```
gaaaagaggc tggagtgggt cgcaaccatt agtgatggtg gtagttacac ctcctatcca    240
gacagtgtga aggggcgatt caccatctcc agagacagtg ccaagaacaa cctgtacctg    300
caaatgagca gtctgaagtc tgaggacaca gccatgtatt actgtgcaag agattactac    360
ggtagtaata gttacacctc gggctttgct tactggggcc aagggactct ggtcactgtc    420
tctgca                                                                426
```

<210> SEQ ID NO 85
<211> LENGTH: 142
<212> TYPE: PRT
<213> ORGANISM: Mus Musculus

<400> SEQUENCE: 85

```
Met Asn Phe Gly Leu Ser Leu Ile Phe Leu Val Leu Val Leu Lys Gly
1               5                   10                  15

Val Gln Cys Glu Val Gln Leu Val Glu Ser Gly Gly Gly Leu Val Lys
            20                  25                  30

Pro Gly Gly Ser Leu Lys Leu Ser Cys Ala Ala Ser Gly Phe Thr Phe
        35                  40                  45

Ser Asp Tyr Tyr Met Tyr Trp Val Arg Gln Thr Pro Glu Lys Arg Leu
    50                  55                  60

Glu Trp Val Ala Thr Ile Ser Asp Gly Gly Ser Tyr Thr Ser Tyr Pro
65                  70                  75                  80

Asp Ser Val Lys Gly Arg Phe Thr Ile Ser Arg Asp Ser Ala Lys Asn
                85                  90                  95

Asn Leu Tyr Leu Gln Met Ser Ser Leu Lys Ser Glu Asp Thr Ala Met
            100                 105                 110

Tyr Tyr Cys Ala Arg Asp Tyr Tyr Gly Ser Asn Ser Tyr Thr Ser Gly
        115                 120                 125

Phe Ala Tyr Trp Gly Gln Gly Thr Leu Val Thr Val Ser Ala
    130                 135                 140
```

<210> SEQ ID NO 86
<211> LENGTH: 396
<212> TYPE: DNA
<213> ORGANISM: Mus Musculus

<400> SEQUENCE: 86

```
atggattcac aggcccaggt tcttatattg ctgctgctat gggtatctgg tacctgtggg    60
gacattgtga tgtcacagtc tccatcctcc ctggctgtgt cagcaggaga gaaggtcact    120
atgagctgca aatccagtca gagtctgctc aatagtagaa cccgaaagaa ctacttggct    180
tggtaccagc agaaaccagg gcagtctcct aaactgctga tctactgggc atccactagg    240
gaatctgggg tccctgatcg cttcacaggc agtggatctg ggacagattt cactctcacc    300
atcagcagtg tgcaggctga agacctggca gtttattact gcaagcaatc ttataatctg    360
tacacgttcg gaggggggac caagctggaa ataaaa                               396
```

<210> SEQ ID NO 87
<211> LENGTH: 132
<212> TYPE: PRT
<213> ORGANISM: Mus Musculus

<400> SEQUENCE: 87

```
Met Asp Ser Gln Ala Gln Val Leu Ile Leu Leu Leu Leu Trp Val Ser
1               5                   10                  15

Gly Thr Cys Gly Asp Ile Val Met Ser Gln Ser Pro Ser Ser Leu Ala
```

```
                20                  25                  30
Val Ser Ala Gly Glu Lys Val Thr Met Ser Cys Lys Ser Gln Ser
            35                  40                  45

Leu Leu Asn Ser Arg Thr Arg Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys Lys Gln Ser Tyr Asn Leu Tyr Thr Phe Gly Gly Gly Thr Lys
        115                 120                 125

Leu Glu Ile Lys
        130
```

<210> SEQ ID NO 88
<211> LENGTH: 393
<212> TYPE: DNA
<213> ORGANISM: Mus Musculus

<400> SEQUENCE: 88

```
atgaagttgc ctgttaggct gttggtgctg atgttctgga ttcctgcttc cagcagtgat      60
gttttgatga cccaaactcc actctccctg cctgtcagtc ttggagatca agcctccatc     120
tcttgcagat ctagtcagag cattgtacat agtaatggaa acacctattt agaatggtac     180
ctgcagaaac aggccagtc tccaaagctc ctgatctaca agtttccaa ccgatttct       240
ggggtcccag acaggttcag tggcagtgga tcagggacag atttcacact caagatcagc     300
agagtggagg ctgaggatct gggagtttat ttctgctttc aaggttcaca tgttcctctc     360
acgttcggtg ctgggaccaa gctggagctg aaa                                  393
```

<210> SEQ ID NO 89
<211> LENGTH: 131
<212> TYPE: PRT
<213> ORGANISM: Mus Musculus

<400> SEQUENCE: 89

```
Met Lys Leu Pro Val Arg Leu Leu Val Leu Met Phe Trp Ile Pro Ala
1               5                   10                  15

Ser Ser Ser Asp Val Leu Met Thr Gln Thr Pro Leu Ser Leu Pro Val
            20                  25                  30

Ser Leu Gly Asp Gln Ala Ser Ile Ser Cys Arg Ser Ser Gln Ser Ile
        35                  40                  45

Val His Ser Asn Gly Asn Thr Tyr Leu Glu Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Phe Gln Gly Ser His Val Pro Leu Thr Phe Gly Ala Gly Thr Lys Leu
        115                 120                 125

Glu Leu Lys
        130
```

<210> SEQ ID NO 90
<211> LENGTH: 1338
<212> TYPE: DNA
<213> ORGANISM: Artificial Sequence
<220> FEATURE:
<223> OTHER INFORMATION: Synthetic Construct

<400> SEQUENCE: 90

```
caggtgcagc tgcagcagcc tggcgctgag ctggtgaagc ctggagcctc cgtgaagatg      60
tcctgcaagg cctccggcta ctccttcacc agctactgga tcaactgggt gaagcagagg     120
cccggacagg gcctggagtg gattggagac gtgcaccctg gccggggagt gtccacctac     180
aacgccaagt tcaagtccaa ggccaccctg accctggaca cctccagctc accgcctac     240
atgcagctgt cctccctgac ctccgaggac tccgccgtgt actactgcag caggtcccac     300
ggcaacacct actggttttt cgacgtgtgg ggcgccggaa ccacagtgac cgtgtcctcc     360
gccaaaacga cccccccatc tgtctatcca ctggcccctg gatctgctgc caaactaac      420
tccatggtga ccctgggatg cctggtcaag ggctatttcc ctgagccagt gacagtgacc     480
tggaactctg gatccctgtc cagcggtgtg cacaccttcc cagctgtcct ggagtctgac     540
ctctacactc tgagcagctc agtgactgtc ccctccagcc ctcggcccag cgagaccgtc     600
acctgcaacg ttgcccaccc ggccagcagc accaaggtgg acaagaaaat tgtgcccagg     660
gattgtggtt gtaagccttg catatgtaca gtcccagaag tatcatctgt cttcatcttc     720
ccccaaaagc ccaaggatgt gctcaccatt actctgactc ctaaggtcac gtgtgttgtg     780
gtagacatca gcaaggatga tcccgaggtc cagttcagct ggtttgtaga tgatgtggag     840
gtgcacacag ctcagacgca accccgggag gagcagttca acagcacttt ccgctcagtc     900
agtgaacttc ccatcatgca ccaggactgg ctcaatggca aggagttcaa atgcagggtc     960
aacagtgcag ctttccctgc ccccatcgag aaaaccatct ccaaaaccaa aggcagaccg    1020
aaggctccac aggtgtacac cattccacct cccaaggagc agatgccaa ggataaagtc     1080
agtctgacct gcatgataac agacttcttc cctgaagaca ttactgtgga gtggcagtgg    1140
aatgggcagc cagcggagaa ctacaagaac actcagccca tcatgaacac gaatggctct    1200
tacttcgtct acagcaagct caatgtgcag aagagcaact gggaggcagg aaatactttc    1260
acctgctctg tgttacatga gggcctgcac aaccaccata ctgagaagag cctctcccac    1320
tctcctggta aatgatga                                                  1338
```

<210> SEQ ID NO 91
<211> LENGTH: 444
<212> TYPE: PRT
<213> ORGANISM: Artificial Sequence
<220> FEATURE:
<223> OTHER INFORMATION: Synthetic Construct

<400> SEQUENCE: 91

```
Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Ser Phe Thr Ser Tyr
            20                  25                  30

Trp Ile Asn Trp Val Lys Gln Arg Pro Gly Gln Gly Leu Glu Trp Ile
        35                  40                  45

Gly Asp Val His Pro Gly Arg Gly Val Ser Thr Tyr Asn Ala Lys Phe
    50                  55                  60
```

```
            Lys Ser Lys Ala Thr Leu Thr Leu Asp Thr Ser Ser Thr Ala Tyr
             65                  70                  75                  80

Met Gln Leu Ser Ser Leu Thr Ser Glu Asp Ser Ala Val Tyr Tyr Cys
                             85                  90                  95

Ser Arg Ser His Gly Asn Thr Tyr Trp Phe Phe Asp Val Trp Gly Ala
                        100                 105                 110

Gly Thr Thr Val Thr Val Ser Ser Ala Lys Thr Thr Pro Pro Ser Val
                        115                 120                 125

Tyr Pro Leu Ala Pro Gly Ser Ala Ala Gln Thr Asn Ser Met Val Thr
                        130                 135                 140

Leu Gly Cys Leu Val Lys Gly Tyr Phe Pro Glu Pro Val Thr Val Thr
            145                 150                 155                 160

Trp Asn Ser Gly Ser Leu Ser Ser Gly Val His Thr Phe Pro Ala Val
                            165                 170                 175

Leu Glu Ser Asp Leu Tyr Thr Leu Ser Ser Val Thr Val Pro Ser
                        180                 185                 190

Ser Pro Arg Pro Ser Glu Thr Val Thr Cys Asn Val Ala His Pro Ala
                        195                 200                 205

Ser Ser Thr Lys Val Asp Lys Lys Ile Val Pro Arg Asp Cys Gly Cys
                210                 215                 220

Lys Pro Cys Ile Cys Thr Val Pro Glu Val Ser Ser Val Phe Ile Phe
            225                 230                 235                 240

Pro Pro Lys Pro Lys Asp Val Leu Thr Ile Thr Leu Thr Pro Lys Val
                            245                 250                 255

Thr Cys Val Val Val Asp Ile Ser Lys Asp Asp Pro Glu Val Gln Phe
                        260                 265                 270

Ser Trp Phe Val Asp Asp Val Glu Val His Thr Ala Gln Thr Gln Pro
                        275                 280                 285

Arg Glu Glu Gln Phe Asn Ser Thr Phe Arg Ser Val Ser Glu Leu Pro
                290                 295                 300

Ile Met His Gln Asp Trp Leu Asn Gly Lys Glu Phe Lys Cys Arg Val
            305                 310                 315                 320

Asn Ser Ala Ala Phe Pro Ala Pro Ile Glu Lys Thr Ile Ser Lys Thr
                            325                 330                 335

Lys Gly Arg Pro Lys Ala Pro Gln Val Tyr Thr Ile Pro Pro Pro Lys
                        340                 345                 350

Glu Gln Met Ala Lys Asp Lys Val Ser Leu Thr Cys Met Ile Thr Asp
                        355                 360                 365

Phe Phe Pro Glu Asp Ile Thr Val Glu Trp Gln Trp Asn Gly Gln Pro
            370                 375                 380

Ala Glu Asn Tyr Lys Asn Thr Gln Pro Ile Met Asn Thr Asn Gly Ser
            385                 390                 395                 400

Tyr Phe Val Tyr Ser Lys Leu Asn Val Gln Lys Ser Asn Trp Glu Ala
                            405                 410                 415

Gly Asn Thr Phe Thr Cys Ser Val Leu His Glu Gly Leu His Asn His
                        420                 425                 430

His Thr Glu Lys Ser Leu Ser His Ser Pro Gly Lys
                        435                 440

<210> SEQ ID NO 92
<211> LENGTH: 1356
<212> TYPE: DNA
<213> ORGANISM: Artificial Sequence
<220> FEATURE:
<223> OTHER INFORMATION: Synthetic Construct
```

<400> SEQUENCE: 92

```
caggtgcagc tgcagcagcc tggcgctgag ctggtgaagc ctggagcctc cgtgaagatg      60
tcctgcaagg cctccggcta ctccttcacc agctactgga tcaactgggt gaagcagagg     120
cccggacagg gcctggagtg gattggagac gtgcaccctg gcggggagt gtccacctac      180
aacgccaagt tcaagtccaa ggccaccctg accctggaca cctccagctc accgcctac      240
atgcagctgt cctccctgac ctccgaggac tccgccgtgt actactgcag caggtcccac     300
ggcaacacct actggttttt cgacgtgtgg ggcgccggaa ccacagtgac cgtgtcctcc     360
gccaaaacaa cagccccatc ggtctatcca ctggcccctg tgtgtggaga tacaactggc     420
tcctcggtga ctctaggatg cctggtcaag ggttatttcc ctgagccagt gaccttgacc     480
tggaactctg gatccctgtc cagtggtgtg cacaccttcc cagctgtcct gcagtctgac     540
ctctacaccc tcagcagctc agtgactgta acctcgagca cctggcccag ccagtccatc     600
acctgcaatg tggcccaccc ggcaagcagc accaaggtgg acaagaaaat tgagcccaga     660
gggcccacaa tcaagccctg tcctccatgc aaatgcccag cacctaacct cttgggtgga     720
ccatccgtct tcatcttccc tccaaagatc aaggatgtac tcatgatctc cctgagcccc     780
atagtcacat gtgtggtggt ggatgtgagc gaggatgacc cagatgtcca gatcagctgg     840
tttgtgaaca acgtggaagt acacacagct cagacacaaa cccatagaga ggattacaac     900
agtactctcc gggtggtcag tgccctcccc atccagcacc aggactggat gagtggcaag     960
gagttcaaat gcaaggtcaa caacaaagac ctcccagcgc catcgagag aaccatctca    1020
aaacccaaag ggtcagtaag agctccacag gtatatgtct tgcctccacc agaagaagag    1080
atgactaaga aacaggtcac tctgacctgc atggtcacag acttcatgcc tgaagacatt    1140
tacgtggagt ggaccaacaa cggaaaaca gagctaaact acaagaacac tgaaccagtc    1200
ctggactctg atggttctta cttcatgtac agcaagctga gagtgaaaaa gaagaactgg    1260
gtggaaagaa atagctactc ctgttcagtg gtccacgagg gtctgcacaa tcaccacacg    1320
actaagagct ctcccggac tccgggtaaa tgatga                               1356
```

<210> SEQ ID NO 93
<211> LENGTH: 450
<212> TYPE: PRT
<213> ORGANISM: Artificial Sequence
<220> FEATURE:
<223> OTHER INFORMATION: Synthetic Construct

<400> SEQUENCE: 93

```
Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Ser Phe Thr Ser Tyr
            20                  25                  30

Trp Ile Asn Trp Val Lys Gln Arg Pro Gly Gln Gly Leu Glu Trp Ile
        35                  40                  45

Gly Asp Val His Pro Gly Arg Gly Val Ser Thr Tyr Asn Ala Lys Phe
    50                  55                  60

Lys Ser Lys Ala Thr Leu Thr Leu Asp Thr Ser Ser Thr Ala Tyr
65                  70                  75                  80

Met Gln Leu Ser Ser Leu Thr Ser Glu Asp Ser Ala Val Tyr Tyr Cys
                85                  90                  95

Ser Arg Ser His Gly Asn Thr Tyr Trp Phe Phe Asp Val Trp Gly Ala
            100                 105                 110
```

Gly Thr Thr Val Thr Val Ser Ser Ala Lys Thr Thr Ala Pro Ser Val
            115                 120                 125

Tyr Pro Leu Ala Pro Val Cys Gly Asp Thr Thr Gly Ser Ser Val Thr
130                 135                 140

Leu Gly Cys Leu Val Lys Gly Tyr Phe Pro Glu Pro Val Thr Leu Thr
145                 150                 155                 160

Trp Asn Ser Gly Ser Leu Ser Ser Gly Val His Thr Phe Pro Ala Val
            165                 170                 175

Leu Gln Ser Asp Leu Tyr Thr Leu Ser Ser Ser Val Thr Val Thr Ser
            180                 185                 190

Ser Thr Trp Pro Ser Gln Ser Ile Thr Cys Asn Val Ala His Pro Ala
            195                 200                 205

Ser Ser Thr Lys Val Asp Lys Lys Ile Glu Pro Arg Gly Pro Thr Ile
            210                 215                 220

Lys Pro Cys Pro Pro Cys Lys Cys Pro Ala Pro Asn Leu Leu Gly Gly
225                 230                 235                 240

Pro Ser Val Phe Ile Phe Pro Pro Lys Ile Lys Asp Val Leu Met Ile
            245                 250                 255

Ser Leu Ser Pro Ile Val Thr Cys Val Val Asp Val Ser Glu Asp
            260                 265                 270

Asp Pro Asp Val Gln Ile Ser Trp Phe Val Asn Asn Val Glu Val His
            275                 280                 285

Thr Ala Gln Thr Gln Thr His Arg Glu Asp Tyr Asn Ser Thr Leu Arg
            290                 295                 300

Val Val Ser Ala Leu Pro Ile Gln His Gln Asp Trp Met Ser Gly Lys
305                 310                 315                 320

Glu Phe Lys Cys Lys Val Asn Asn Lys Asp Leu Pro Ala Pro Ile Glu
            325                 330                 335

Arg Thr Ile Ser Lys Pro Lys Gly Ser Val Arg Ala Pro Gln Val Tyr
            340                 345                 350

Val Leu Pro Pro Pro Glu Glu Glu Met Thr Lys Lys Gln Val Thr Leu
            355                 360                 365

Thr Cys Met Val Thr Asp Phe Met Pro Glu Asp Ile Tyr Val Glu Trp
370                 375                 380

Thr Asn Asn Gly Lys Thr Glu Leu Asn Tyr Lys Asn Thr Glu Pro Val
385                 390                 395                 400

Leu Asp Ser Asp Gly Ser Tyr Phe Met Tyr Ser Lys Leu Arg Val Glu
            405                 410                 415

Lys Lys Asn Trp Val Glu Arg Asn Ser Tyr Ser Cys Ser Val Val His
            420                 425                 430

Glu Gly Leu His Asn His His Thr Thr Lys Ser Phe Ser Arg Thr Pro
            435                 440                 445

Gly Lys
    450

<210> SEQ ID NO 94
<211> LENGTH: 720
<212> TYPE: DNA
<213> ORGANISM: Artificial Sequence
<220> FEATURE:
<223> OTHER INFORMATION: Synthetic Construct

<400> SEQUENCE: 94
atgaaactgc ccgtgaggct gctggtgctc atgttctgga tccctgcctc cagctccgat    60

```
gtgctgatga cccagacccc tctgtccctg cctgtgtccc tgggcgatca ggccagcatc    120
tcctgcaggt cctcccagtc catcgtgcac tccaacggca cacctacct ggagtggtac    180 ctgcagaagc ccggccagtc ccccaagctg ctgatctaca aggtgtccaa ccggttctcc    240
ggcgtgcccg ataggttctc cggatccggc tccggcaccg actttaccct gaagatctcc    300
agggtggagg ccgaggacct gggcgtgtac tactgctttc agggctccca cgtgcccttc    360
accttcggct ccggcaccaa gctggagatc aagcgggctg atgctgcacc aactgtatcc    420
atcttcccac catccagtga gcagttaaca tctggaggtg cctcagtcgt gtgcttcttg    480
aacaacttct accccaaaga catcaatgtc aagtggaaga ttgatggcag tgaacgacaa    540
aatggcgtcc tgaacagttg gactgatcag gacagcaaag acagcaccta cagcatgagc    600
agcaccctca cgttgaccaa ggacgagtat gaacgacata acagctatac ctgtgaggcc    660
actcacaaga tcaacttc acccattgtc aagagcttca caggaatga gtgttgatga    720
```

<210> SEQ ID NO 95
<211> LENGTH: 219
<212> TYPE: PRT
<213> ORGANISM: Artificial Sequence
<220> FEATURE:
<223> OTHER INFORMATION: Synthetic Construct

<400> SEQUENCE: 95

```
Asp Val Leu Met Thr Gln Thr Pro Leu Ser Leu Pro Val Ser Leu Gly
 1               5                  10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215
```

<210> SEQ ID NO 96
<211> LENGTH: 9
<212> TYPE: PRT
<213> ORGANISM: Homo sapiens

```
<400> SEQUENCE: 96

Ala Glu Phe Arg His Asp Ser Gly Tyr
1               5

<210> SEQ ID NO 97
<211> LENGTH: 14
<212> TYPE: PRT
<213> ORGANISM: Homo sapiens

<400> SEQUENCE: 97

Val His His Gln Lys Leu Val Phe Phe Ala Glu Asp Val Gly
1               5                   10

<210> SEQ ID NO 98
<211> LENGTH: 6
<212> TYPE: PRT
<213> ORGANISM: Homo Sapiens

<400> SEQUENCE: 98

His Gln Lys Leu Val Phe
1               5

<210> SEQ ID NO 99
<211> LENGTH: 10
<212> TYPE: PRT
<213> ORGANISM: Homo sapiens

<400> SEQUENCE: 99

His Gln Lys Leu Val Phe Phe Ala Glu Asp
1               5                   10

<210> SEQ ID NO 100
<211> LENGTH: 7
<212> TYPE: PRT
<213> ORGANISM: Artificial Sequence
<220> FEATURE:
<223> OTHER INFORMATION: Synthetic construct

<400> SEQUENCE: 100

Glu Val His His Gln Lys Leu
1               5

<210> SEQ ID NO 101
<211> LENGTH: 14
<212> TYPE: PRT
<213> ORGANISM: Artificial Sequence
<220> FEATURE:
<223> OTHER INFORMATION: Synthetic construct

<400> SEQUENCE: 101

Val His His Ala Glu Asp Val Phe Phe Ala Glu Asp Val Gly
1               5                   10
```

METHODS OF REDUCING TOXICITY INDUCED BY AMYLOID BETA (A-BETA) OLIGOMERS USING ANTIBODIES SPECIFIC TO A-BETA OLIGOMERS

CROSS-REFERENCE TO RELATED APPLICATIONS

This application is a national phase entry of International PCT application PCT/CA2017/050866, filed Jul. 18, 2017, which claims priority from U.S. provisional application Ser. No. 62/363,566 filed Jul. 18, 2016, International application PCT/CA2016/051303 filed Nov. 9, 2016, U.S. provisional Ser. No. 62/507,587 filed May 17, 2017, U.S. provisional Ser. No. 62/507,633 filed May 17, 2017 and U.S. provisional Ser. No. 62/443,766 filed Jan. 8, 2017, each of these applications being incorporated herein in their entirety by reference.

INCORPORATION OF SEQUENCE LISTING

A computer readable form of the Sequence Listing "P50442US04_SL.txt" (82,193 bytes), submitted via EFS-WEB and created on Nov. 12, 2021, is herein incorporated by reference.

FIELD

The present disclosure relates to antibodies that are selective for Amyloid beta (A-beta or Aβ) oligomers as well as compositions and uses thereof.

BACKGROUND

Amyloid-beta (A-beta), which exists as a 36-43 amino acid peptide, is a product released from amyloid precursor protein (APP) by the enzymes β and γ secretase. In AD patients, A-beta can be present in soluble monomers, insoluble fibrils and soluble oligomers. In monomer form, A-beta exists as a predominantly unstructured polypeptide chain. In fibril form, A-beta can aggregate into distinct morphologies, often referred to as strains. Several of these structures have been determined by solid-state NMR.

For, example, structures for several strains of fibrils are available in the Protein Data Bank (PDB), a crystallographic database of atomic resolution three dimensional structural data, including a 3-fold symmetric Aβ structure (PDB entry, 2M4J); a two-fold symmetric structure of Aβ-40 monomers (PDB entry 2LMN), and a single-chain, parallel in-register structure of Aβ-42 monomers (PDB entry 2MXU).

The structure of 2M4J is reported in Lu et al [8], and the structure of 2MXU is reported in Xiao et al [9]. The structure of 2LMN is reported in Petkova et al [10].

A-beta oligomers have been shown to kill cell lines and neurons in culture and block a critical synaptic activity that subserves memory, referred to as long term potentiation (LTP), in slice cultures and living animals.

The structure of the oligomer has not been determined to date. Moreover, NMR and other evidence indicates that the oligomer exists not in a single well-defined structure, but in a conformationally-plastic, malleable structural ensemble with limited regularity. Moreover, the concentration of toxic oligomer species is far below either that of the monomer or fibril (estimates vary but are on the order of 1000-fold below or more), making this target elusive.

Antibodies that bind A-beta have been described.

WO2009048538A2 titled USE OF ANTI-AMYLOID ANTIBODY IN OCULAR DISEASES discloses chimeric antibodies that recognize one or more binding sites on A-beta and are useful for the treatment for ocular diseases.

U.S. Pat. No. 9,221,812B2 titled COMPOUNDS FOR THE TREATMENT OF DISEASES ASSOCIATED WITH AMYLOID OR AMYLOID-LIKE PROTEINS describes pharmaceutical compositions and discontinuous antibodies that bind A-beta including an epitope between amino acid residues 12 to 24 for the treatment of amyloid-related diseases.

WO2003070760A2 titled ANTI-AMYLOID BETA ANTIBODIES AND THEIR USE discloses antibodies that recognize an A-beta discontinuous epitope, wherein the first region comprises the amino acid sequence AEFRHDSGY (SEQ ID NO: 96) or a fragment thereof and wherein the second region comprises the amino acid sequence VHHQKLVFFAEDVG (SEQ ID NO: 97) or a fragment thereof.

US20110171243A1 titled COMPOUNDS TREATING AMYLOIDOSES discloses a peptide mimotope capable of inducing the in vivo formation of antibodies that bind HQKLVF (SEQ ID NO: 98) and/or HQKLVFFAED (SEQ ID NO: 99), and its use.

WO2008088983A1 and WO2001062801A2 disclose a pegylated antibody fragment that binds A-beta amino acids 13-28 and its use in treating A-beta related diseases. Solanezumab and Crenezumab bind amino acids 16-26 on A-beta. Crenezumab interacts with the monomer, oligomer and fibril. Midregion antibodies, including solanezumab (picomolar affinity) and crenezumab (nanomolar affinity), appear to preferentially bind monomeric A-beta [13].

WO2009149487A2 titled COMPOUNDS FOR TREATING SYMPTOMS ASSOCIATED WITH PARKINSON'S DISEASE describes compounds comprising a peptide having binding capacity for an antibody specific for an A-beta epitope such as EVHHQKL (SEQ ID NO: 100), HQKLVF (SEQ ID NO: 98) and HQKLVFFAED (SEQ ID NO: 99).

The HHQK (SEQ ID NO: 7) domain is described as involved in plaque induction of neurotoxicity in human microglia, as described in Giulian D et al. [11] and Winkler et al. [12]. Non-antibody therapeutic agents that bind HHQK (SEQ ID NO: 7) have been disclosed for the treatment of protein folding diseases (US20150105344A1, WO2006125324A1).

U.S. Pat. Nos. 5,766,846; 5,837,672; and 5,593,846 (which are incorporated herein by reference) describe the production of murine monoclonal antibodies to the central domain of the Aβ peptide. WO 01/62801 describes antibodies that bind A-beta between amino acids 13-28. WO2004071408 discloses humanized antibodies.

WO2009086539A2 titled TREATMENT AND PROPHYLAXIS OF AMYLOIDOSIS is directed to Amyloidosis and amyloid light chain amyloidosis, by administering peptides comprising neoepitopes, such as amyloid protein A (AA) fragments from a C-terminal region of AA, and antibodies specific for neoepitopes of aggregated amyloid proteins, for example, antibodies specific for the C-terminal region of AA fibrils.

WO2003070760 titled ANTI-AMYLOID BETA ANTIBODIES AND THEIR USE is directed towards antibody molecules capable of specifically recognizing two regions of the R-A4 peptide, wherein the first region comprises the amino acid sequence AEFRHDSGY (SEQ ID NO: 96) or a fragment thereof and wherein the second region comprises the amino acid sequence VHHAEDVFFAEDVG (SEQ ID NO: 101) or a fragment thereof.

WO2006066089 titled HUMANIZED AMYLOID BETA ANTIBODIES FOR USE IN IMPROVING COGNITION is directed to improved agents and methods for treatment of diseases associated with beta amyloid and in particular to the identification and characterization of a monoclonal antibody, 12A11, that specifically binds to Aβ peptide and is effective at reducing plaque burden associated with amyloidogenic disorders (e.g., AD).

WO2007068429 titled ANTIBODIES AGAINST AMYLOID BETA 4 WITH GLYCOSYLATED IN THE VARIABLE REGION is directed to a purified antibody molecule preparation being characterized in that at least one antigen binding site comprises a glycosylated asparagine (Asn) in the variable region of the heavy chain ($V_H$).

WO 03/016466 is directed variant 266 antibodies that are engineered to lack an N-glycosylation site within the CDR2 of the heavy chain, pharmaceutical compositions thereof, and polynucleotide sequences, vectors, and transformed cells useful to express the variant antibodies. The variants are described to sequester soluble A-beta peptide from human biological fluids and specifically bind an epitope contained within position 13-28 of the amyloid beta peptide.

Yu et al. describes a hexavalent foldable Aβ1-15 (6Aβ15) fused to PADRE or toxin-derived carrier proteins. Wang et al 2016 report that peripheral administration of this antibody mitigates Alzheimer's disease like pathology and cognitive decline in a transgenic animal of aged Alzheimer Disease [14], [15].

Antibodies that preferentially or selectively bind A-beta oligomers over monomers or over fibrils or over both monomers and fibrils are desirable.

SUMMARY

An aspect includes an isolated antibody comprising a light chain variable region and a heavy chain variable region, optionally fused, the heavy chain variable region comprising complementarity determining regions CDR-H1, CDR-H2 and CDR-H3, the light chain variable region comprising complementarity determining region CDR-L1, CDR-L2 and CDR-L3 and with the amino acid sequences of said CDRs comprising or consisting of the sequences SEQ ID NOs: 1-6; or SEQ ID NOs:1, 2, 80 and 4-6, or SEQ ID NOs: 1, 2, 80-83, for example as shown in Table 2.

In an embodiment, the isolated antibody is conformation specific and/or selective.

In an embodiment, an antibody described herein, optionally the antibody having CDRs comprising or consisting of SEQ ID NOs:1-6 or SEQ ID NOs:1, 2, 80 and 4-6 or SEQ ID NOs: 1, 2, 80-83, selectively binds to a cyclic compound comprising HHQK (SEQ ID NO: 7) over a corresponding linear peptide, optionally wherein the antibody is at least 2 fold, 3 fold, at least 5 fold, at least 10 fold, at least 20 fold, at least 30 fold, at least 40 fold, at least 50 fold, at least 100 fold, at least 500 fold, at least 1000 fold more selective for the cyclic compound over the corresponding linear compound.

In another embodiment, an antibody described herein, optionally the antibody having CDRs comprising or consisting of SEQ ID NOs:1-6 or SEQ ID NOs:1, 2, 80 and 4-6 or SEQ ID NOs: 1, 2, 80-83 selectively binds does not specifically and/or selectively bind a linear peptide comprising sequence HHQK (SEQ ID NO: 7), optionally wherein the sequence of the linear peptide is a linear version of a cyclic compound used to raise the antibody.

In another embodiment, the antibody having a CDR set as listed in Table 2, selectively binds A-beta oligomer over A-beta monomer and/or A-beta fibril.

In another embodiment, the selectivity is at least 2 fold, at least 3 fold, at least 5 fold, at least 10 fold, at least 20 fold, at least 30 fold, at least 40 fold, at least 50 fold, at least 100 fold, at least 500 fold, at least 1000 fold more selective for A-beta oligomer over A-beta monomer and/or A-beta fibril.

In another embodiment, the antibody lacks or has negligible binding to A-beta fibril plaques in situ.

In another embodiment, the antibody is a monoclonal antibody or a polyclonal antibody.

In another embodiment, the antibody having CDRs comprising or consisting of SEQ ID NOs:1-6 or SEQ ID NOs:1, 2, 80 and 4-6 or SEQ ID NOs: 1, 2, 80-83 is a humanized antibody. In an embodiment, the humanized antibody has a heavy chain variable region having a sequence and/or a light chain variable region having a sequence selected from the sequences in Table 4A.

Also provided in another aspect, is a hybridoma expressing an antibody comprising CDRs described in Table 2.

A further aspect is a humanized antibody wherein the humanized antibody has a heavy chain variable region having a sequence and/or a light chain variable region having a sequence selected from the sequences in Table 4B.

In an embodiment, the humanized antibody selectively or specifically binds a cyclic peptide having sequence of SEQ ID NO: 12, relative to a linear peptide of the same sequence or selectively or specifically binds oligomeric Abeta relative to A-beta monomer and/or A-beta fibril.

In another embodiment, the antibody is an antibody binding fragment of an antibody described herein selected from Fab, Fab', F(ab')2, scFv, dsFv, ds-scFv, dimers, nanobodies, minibodies, diabodies, and multimers thereof.

An aspect includes immunoconjugate comprising the antibody described herein and a detectable label or cytotoxic agent.

In an embodiment, the detectable label comprises a positron emitting radionuclide, optionally for use in subject imaging such as PET imaging.

An aspect includes a composition comprising the antibody described herein, or the immunoconjugate described herein, optionally with a diluent.

An aspect includes a nucleic acid molecule encoding a proteinaceous portion of the compound or immunogen described herein, the antibody described herein or proteinaceous immunoconjugates described herein.

An aspect includes a vector comprising the nucleic acid described herein.

An aspect includes a cell expressing an antibody described herein, optionally wherein the cell is a hybridoma comprising the vector described herein.

An aspect includes a kit comprising the antibody described herein, the immunoconjugate described herein, the composition described herein, the nucleic acid molecule described herein, the vector described herein or the cell described herein.

An aspect includes a method of determining if a biological sample comprises A-beta, the method comprising:
a. contacting the biological sample with an antibody described herein or the immunoconjugate described herein; and
b. detecting the presence of any antibody complex.

In an embodiment, the biological sample contains A-beta oligomer the method comprising:
a. contacting the sample with the antibody described herein or the immunoconjugate described herein that is specific and/or selective for A-beta oligomers under conditions permissive for forming an antibody: A-beta oligomer complex; and b. detecting the presence of any complex;

wherein the presence of detectable complex is indicative that the sample may contain A-beta oligomer.

In another embodiment, the amount of complex is measured.

In another embodiment, the sample comprises brain tissue or an extract thereof, whole blood, plasma, serum and/or CSF.

In another embodiment, the sample is a human sample.

In another embodiment, the sample is compared to a control, optionally a previous sample.

In another embodiment, the level of A-beta is detected by an analytical assay including but not limited to SPR, Kinexa, Mesoscale, ELISA, Singulex, Luminex and Simoa.

An aspect includes a method of measuring a level of A-beta in a subject, the method comprising administering to a subject at risk or suspected of having or having AD, an immunoconjugate comprising an antibody described herein wherein the antibody is conjugated to a detectable label; and detecting the label, optionally quantitatively detecting the label.

In an embodiment, the label is a positron emitting radionuclide.

An aspect includes a method of inhibiting A-beta oligomer propagation, the method comprising contacting a cell or tissue expressing A-beta with or administering to a subject in need thereof an effective amount of an A-beta oligomer specific or selective antibody or immunoconjugate described herein, to inhibit A-beta aggregation and/or oligomer propagation.

An aspect includes a method of treating AD and/or other A-beta amyloid related diseases, the method comprising administering to a subject in need thereof 1) an effective amount of an antibody or immunoconjugate described herein, or a pharmaceutical composition comprising said antibody; 2) a nucleic acid or vector comprising a nucleic acid encoding the antibody of 1, to a subject in need thereof.

In an embodiment, a biological sample from the subject to be treated is assessed for the presence or levels of A-beta using an antibody described herein.

In another embodiment, the antibody, immunoconjugate, composition or nucleic acid or vector is administered directly to the brain or other portion of the CNS.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

An embodiment of the present disclosure will now be described in relation to the drawings in which:

FIG. 1 Graph reporting effect of antibodies on propagation of A-beta oligomers in vitro.

DETAILED DESCRIPTION OF THE DISCLOSURE

Provided herein are antibodies comprising CDRs having sequences as shown in Table 2, and/or having variable region sequences provided in any of Tables 3, 4A and 4B and/or the sequences in Table 8 are described, immunotherapeutic compositions thereof and methods of use thereof. Said antibodies may target epitopes preferentially accessible in toxic oligomeric species of A-beta, including oligomeric species associated with Alzheimer's disease (AD).

As shown in the Examples, antibodies raised using a cyclic peptide comprising HHQK (SEQ ID NO: 7), preferentially bound oligomeric Abeta and/or selectively bound the cyclic peptide compared to a linear peptide of the same sequence (e.g. corresponding linear sequence). Experimental results are described and identify epitope-specific and conformationally selective antibodies that bind synthetic oligomer selectively compared to synthetic monomers, bind CSF from AD patients preferentially over control CSF and/or bind soluble brain extract from AD patients preferentially over control soluble brain extract. Further staining of AD brain tissue identified antibodies that show no or negligible plaque binding and in vitro studies found that the antibodies inhibited Aб oligomer propagation and aggregation.

I. Definitions

As used herein, the term 'A-beta' may alternately be referred to as 'amyloid beta', 'amyloid β', A-beta, A-beta or 'Aβ'. Amyloid beta is a peptide of 36-43 amino acids and includes all wild-type and mutant forms of all species, particularly human A-beta. A-beta40 refers to the 40 amino acid form; A-beta42 refers to the 42 amino acid form, etc. The amino acid sequence of human wildtype A-beta42 is shown in SEQ ID NO: 73.

As used herein, the term "A-beta monomer" herein refers to any of the individual subunit forms of the A-beta (e.g. 1-40, 1-42, 1-43) peptide.

As used herein, the term "A-beta oligomer" herein refers to a plurality of any of the A-beta subunits wherein several (e.g. at least two) A-beta monomers are non-covalently aggregated in a conformationally-flexible, partially-ordered, three-dimensional globule of less than about 100, or more typically less than about 50 monomers. For example, an oligomer may contain 3 or 4 or 5 or more monomers. The term "A-beta oligomer" as used herein includes both synthetic A-beta oligomer and/or native A-beta oligomer. "Native A-beta oligomer" refers to A-beta oligomer formed in vivo, for example in the brain and CSF of a subject with AD.

As used herein, the term "A-beta fibril" refers to a molecular structure that comprises assemblies of non-covalently associated, individual A-beta peptides which show fibrillary structure under an electron microscope. The fibrillary structure is typically a "cross beta" structure; there is no theoretical upper limit on the size of multimers, and fibrils may comprise thousands or many thousands of monomers. Fibrils can aggregate by the thousands to form senile plaques, one of the primary pathological morphologies diagnostic of AD.

The term "HHQK" means the amino acid sequence histidine, histidine, glutamine, lysine, as shown in SEQ ID NO: 7. Depending on the context, the reference of the amino acid sequence can refer to a sequence in A-beta or an isolated peptide, such as the amino acid sequence of a cyclic compound.

The term "amino acid" includes all of the naturally occurring amino acids as well as modified L-amino acids. The atoms of the amino acid can include different isotopes. For example, the amino acids can comprise deuterium substituted for hydrogen nitrogen-15 substituted for nitrogen-14, and carbon-13 substituted for carbon-12 and other similar changes.

The term "antibody" as used herein is intended to include, monoclonal antibodies, polyclonal antibodies, single chain, veneered, humanized and other chimeric antibodies and binding fragments thereof, including for example a single chain Fab fragment, Fab'2 fragment or single chain Fv fragment. The antibody may be from recombinant sources and/or produced in animals such as rabbits, llamas, sharks etc. Also included are human antibodies that can be produced in transgenic animals or using biochemical techniques or can be isolated from a library such as a phage library. Humanized or other chimeric antibodies may include sequences from one or more than one isotype or class or species.

The phrase "isolated antibody" refers to antibody produced in vivo or in vitro that has been removed from the source that produced the antibody, for example, an animal, hybridoma or other cell line (such as recombinant insect, yeast or bacteria cells that produce antibody). The isolated antibody is optionally "purified", which means at least: 80%, 85%, 90%, 95%, 98% or 99% purity.

The term "binding fragment" as used herein to a part or portion of an antibody or antibody chain comprising fewer amino acid residues than an intact or complete antibody or antibody chain and which binds the antigen or competes with intact antibody. Exemplary binding fragments include without limitations Fab, Fab', F(ab')2, scFv, dsFv, ds-scFv, dimers, nanobodies, minibodies, diabodies, and multimers thereof. Fragments can be obtained via chemical or enzymatic treatment of an intact or complete antibody or antibody chain. Fragments can also be obtained by recombinant means. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, dsFv, ds-scFv, dimers, minibodies, diabodies, bispecific antibody fragments and other fragments can also be constructed by recombinant expression techniques.

The terms "IMGT numbering" or "ImMunoGeneTics database numbering", which are recognized in the art, refer to a system of numbering amino acid residues which are more variable (i.e. hypervariable) than other amino acid residues in the heavy and light chain variable regions of an antibody, or antigen binding portion thereof.

As used herein, the term "conformational epitope" refers to an epitope where the epitope amino acid sequence has a particular three-dimensional structure wherein at least an aspect of the three-dimensional structure not present or less likely to be present in another form for example a corresponding linear peptide or Abeta monomer and is specifically and/or selectively recognized by the cognate antibody. Antibodies which specifically bind a conformation-specific epitope recognize the spatial arrangement of one or more of the amino acids of that conformation-specific epitope. For example, an HHQK (SEQ ID NO: 7) conformational epitope refers to an epitope of HHQK (SEQ ID NO:7) that is recognized by antibodies selectively, for example at least 2 fold, 3 fold, 5 fold, 10 fold, 50 fold, 100 fold, 250 fold, 500 fold or 1000 fold or greater more selectivity as compared to antibodies raised using linear HHQK (SEQ ID NO: 7). When an antibody is said to selectively bind an epitope such as a conformational epitope, such as HHQK (SEQ ID NO: 7), what is meant is that the antibody preferentially binds one or more particular conformations containing the specified residues or a part thereof with greater affinity than it binds said residues in another conformation. For example, when an antibody is said to selectively bind a cyclopeptide comprising HHQK or related epitope relative to a corresponding linear peptide, the antibody binds the cyclopeptide with at least a 2 fold greater affinity than it binds the linear peptide. Similarly, when an antibody is said to selectively bind oligomeric Abeta, the antibody binds the oligomeric species with at least a 2 fold greater affinity than it binds Abeta monomer and/or plaque fibrils.

The term "no or negligible plaque binding" or "lacks or has negligible plaque binding" as used herein with respect to an antibody means that the antibody does not show typical plaque morphology staining on immunohistochemistry (e.g. in situ, optionally as compared to plaque staining seen with Abeta antibody 6E10) and the level of staining is comparable to or no more than 2 fold the level seen with an IgG negative (e.g. irrelevant) isotype control.

The term "Isolated peptide" refers to peptide that has been produced, for example, by recombinant or synthetic techniques, and removed from the source that produced the peptide, such as recombinant cells or residual peptide synthesis reactants. The isolated peptide is optionally "purified", which means at least: 80%, 85%, 90%, 95%, 98% or 99% purity and optionally pharmaceutical grade purity.

The term "detectable label" as used herein refers to moieties such as peptide sequences (such a myc tag, HA-tag, V5-tag or NE-tag), fluorescent proteins that can be appended or introduced into a peptide or compound described herein and which is capable of producing, either directly or indirectly, a detectable signal. For example, the label may be radio-opaque, positron-emitting radionuclide (for example for use in PET imaging), or a radioisotope, such as $^{3}H$, $^{13}N$, $^{14}C$, $^{18}F$, $^{32}P$, $^{35}S$, $^{123}I$, $^{125}I$, $^{131}I$; a fluorescent (fluorophore) or chemiluminescent (chromophore) compound, such as fluorescein isothiocyanate, rhodamine or luciferin; an enzyme, such as alkaline phosphatase, beta-galactosidase or horseradish peroxidase; an imaging agent; or a metal ion. The detectable label may be also detectable indirectly for example using secondary antibody.

The term "epitope" as commonly used means an antibody binding site, typically a polypeptide segment, in an antigen that is specifically recognized by the antibody. As used herein "epitope" can also refer to the amino acid sequences or part thereof identified on A-beta using the collective coordinates method described. For example an antibody generated against an isolated peptide corresponding to a cyclic compound comprising the identified target region HHQK SEQ ID NO:7), recognizes part or all of said epitope sequence. An epitope is "accessible" in the context of the present specification when it is accessible to binding by an antibody.

The term "greater affinity" as used herein refers to a relative degree of antibody binding where an antibody X binds to target Y more strongly ($K_{on}$) and/or with a smaller dissociation constant ($K_{off}$) than to target Z, and in this context antibody X has a greater affinity for target Y than for Z. Likewise, the term "lesser affinity" herein refers to a degree of antibody binding where an antibody X binds to target Y less strongly and/or with a larger dissociation constant than to target Z, and in this context antibody X has a lesser affinity for target Y than for Z. The affinity of binding between an antibody and its target antigen, can be expressed as $K_A$ equal to $1/K_D$ where $K_D$ is equal to $k_{on}/k_{off}$. The $k_{on}$ and $k_{off}$ values can be measured using surface plasmon resonance technology, for example using a Molecular Affinity Screening System (MASS-1) (Sierra Sensors GmbH, Hamburg, Germany). An antibody that is selective for a conformation presented in a cyclic compound optional a cyclic peptide for example has a greater affinity for the cyclic compound (e.g. cyclic peptide) compared to a corresponding sequence in linear form (e.g. the sequence non-cyclized).

The term "corresponding linear compound" with regard to a cyclic compound refers to a compound, optionally a peptide, comprising or consisting of the same sequence or chemical moieties as the cyclic compound but in linear (i.e. non-cyclized) form, for example having properties as would be present in solution of a linear peptide. For example, the corresponding linear compound can be the synthesized peptide that is not cyclized.

As used herein "specifically binds" in reference to an antibody means that the antibody recognizes an epitope sequence and binds to its target antigen with a minimum affinity. For example a multivalent antibody binds its target with a $K_D$ of at least 1e-6, at least 1e-7, at least 1e-8, at least 1e-9, or at least 1e-10. Affinities greater than at least 1e-8 may be preferred. For example the $K_D$ may be in the nanomolar range or the picomolar range. An antigen binding fragment such as Fab fragment comprising one variable domain, may bind its target with a 10 fold or 100 fold less affinity than a multivalent interaction with a non-fragmented antibody.

The term "selectively binds" as used herein with respect to an antibody that selectively binds a form of A-beta (e.g. fibril, monomer or oligomer) or a cyclic compound means that the antibody binds the form with at least 2 fold, at least 3 fold, or at least 5 fold, at least 10 fold, at least 100 fold, at least 250 fold, at least 500 fold or at least 1000 fold or more greater affinity. Accordingly an antibody that is more selective for a particular conformation (e.g. oligomer) preferentially binds the particular form of A-beta with at least 2 fold etc. greater affinity compared to another form and/or a linear peptide.

The term "animal" or "subject" as used herein includes all members of the animal kingdom including mammals, optionally including or excluding humans.

A "conservative amino acid substitution" as used herein, is one in which one amino acid residue is replaced with another amino acid residue without abolishing the protein's desired properties. Suitable conservative amino acid substitutions can be made by substituting amino acids with similar hydrophobicity, polarity, and R-chain length for one another. Examples of conservative amino acid substitution include:

| Conservative Substitutions | |
| --- | --- |
| Type of Amino Acid | Substitutable Amino Acids |
| Hydrophilic | Ala, Pro, Gly, Glu, Asp, Gln, Asn, Ser, Thr |
| Sulphydryl | Cys |
| Aliphatic | Val, Ile, Leu, Met |
| Basic | Lys, Arg, His |
| Aromatic | Phe, Tyr, Trp |

The term "sequence identity" as used herein refers to the percentage of sequence identity between two polypeptide sequences or two nucleic acid sequences. To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions.times.100%). In one embodiment, the two sequences are the same length. The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, word length=12 to obtain nucleotide sequences homologous to a nucleic acid molecules of the present application. BLAST protein searches can be performed with the XBLAST program parameters set, e.g., to score-50, word length=3 to obtain amino acid sequences homologous to a protein molecule described herein. To obtain gapped alignments for comparison purposes, Gapped BLAST can be utilized as described in Altschul et al., 1997, Nucleic Acids Res. 25:3389-3402. Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used (see, e.g., the NCBI website). Another preferred non-limiting example of a mathematical algorithm utilized for the comparison of sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

For antibodies, percentage sequence identities can be determined when antibody sequences maximally aligned by IMGT or other (e.g. Kabat numbering convention). After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

The term "nucleic acid sequence" as used herein refers to a sequence of nucleoside or nucleotide monomers consisting of naturally occurring bases, sugars and intersugar (backbone) linkages. The term also includes modified or substituted sequences comprising non-naturally occurring monomers or portions thereof. The nucleic acid sequences of the present application may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine. The nucleic acid can be either double stranded or single stranded, and represents the sense or antisense strand. Further, the term "nucleic acid" includes the complementary nucleic acid sequences as well as codon optimized or synonymous codon equivalents. The term "isolated nucleic acid sequences" as used herein refers to a nucleic acid substantially free of cellular material or culture medium when produced by recombinant DNA techniques, or chemical precursors, or other chemicals when chemically synthesized. An isolated nucleic acid is also substantially free of sequences which naturally flank the nucleic acid (i.e. sequences located at the 5' and 3' ends of the nucleic acid) from which the nucleic acid is derived.

"Operatively linked" is intended to mean that the nucleic acid is linked to regulatory sequences in a manner which allows expression of the nucleic acid. Suitable regulatory sequences may be derived from a variety of sources, including bacterial, fungal, viral, mammalian, or insect genes. Selection of appropriate regulatory sequences is dependent on the host cell chosen and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

The term "vector" as used herein comprises any intermediary vehicle for a nucleic acid molecule which enables said nucleic acid molecule, for example, to be introduced into prokaryotic and/or eukaryotic cells and/or integrated into a genome, and include plasmids, phagemids, bacteriophages or viral vectors such as retroviral based vectors, Adeno Associated viral vectors and the like. The term "plasmid" as used herein generally refers to a construct of extrachromosomal genetic material, usually a circular DNA duplex, which can replicate independently of chromosomal DNA.

By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature (Tm=81.5° C.−16.6 (Log 10 [Na+])+0.41(% (G+C)− 600/l), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5× sodium chloride/sodium citrate (SSC)/5×Denhardt's solution/1.0% SDS at Tm−5° C. based on the above equation, followed by a wash of 0.2×SSC/0.1% SDS at 60° C. Moderately stringent hybridization conditions include a washing step in 3×SSC at 42° C. It is understood, however, that equivalent stringencies may be achieved using alternative buffers, salts and temperatures. Additional guidance regarding hybridization conditions may be found in: Current Protocols in Molecular Biology, John Wiley & Sons, N.Y., 2002, and in: Sambrook et al., Molecular Cloning: a Laboratory Manual, Cold Spring Harbor Laboratory Press, 2001.

The term "treating" or "treatment" as used herein and as is well understood in the art, means an approach for obtaining beneficial or desired results, including clinical results. Beneficial or desired clinical results can include, but are not limited to, alleviation or amelioration of one or more symptoms or conditions, diminishment of extent of disease, or stabilized (i.e. not worsening) state of disease.

The term "administered" as used herein means administration of a therapeutically effective dose of a compound or composition of the disclosure to a cell or subject.

As used herein, the phrase "effective amount" means an amount effective, at dosages and for periods of time necessary to achieve a desired result. Effective amounts when administered to a subject may vary according to factors such as the disease state, age, sex, weight of the subject. Dosage regime may be adjusted to provide the optimum therapeutic response.

The term "pharmaceutically acceptable" means that the carrier, diluent, or excipient is compatible with the other components of the formulation and not substantially deleterious to the recipient thereof.

Compositions or methods "comprising" or "including" one or more recited elements may include other elements not specifically recited. For example, a composition that "comprises" or "includes" an antibody may contain the antibody alone or in combination with other ingredients.

In understanding the scope of the present disclosure, the term "consisting" and its derivatives, as used herein, are intended to be close ended terms that specify the presence of stated features, elements, components, groups, integers, and/or steps, and also exclude the presence of other unstated features, elements, components, groups, integers and/or steps.

The recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about." Further, it is to be understood that "a," "an," and "the" include plural referents unless the content clearly dictates otherwise. The term "about" means plus or minus 0.1 to 50%, 5-50%, or 10-40%, preferably 10-20%, more preferably 10% or 15%, of the number to which reference is being made.

Further, the definitions and embodiments described in particular sections are intended to be applicable to other embodiments herein described for which they are suitable as would be understood by a person skilled in the art. For example, in the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The singular forms of the articles "a," "an," and "the" include plural references unless the context clearly dictates otherwise. For example, the term "a compound" or "at least one compound" can include a plurality of compounds, including mixtures thereof.

II. Antibodies and Nucleic acids

Disclosed herein are particular antibodies and uses thereof.

As demonstrated in the Examples, antibodies raised using cyclo(CGHHQKG) (SEQ ID NO: 12) were sequenced, selectively bound the cyclic compound relative to the corresponding linear peptide, selectively bound A-beta oligomer over monomer, and/or lacked appreciable plaque staining in AD tissue. Further said antibody was able to inhibit in vitro propagation of A-beta aggregation.

Accordingly an aspect includes an antibody comprising a light chain variable region and a heavy chain variable region, optionally fused, the heavy chain variable region comprising complementarity determining regions CDR-H1, CDR-H2 and CDR-H3, the light chain variable region comprising complementarity determining region CDR-L1, CDR-L2 and CDR-L3 and with the amino acid sequences of said CDRs comprising the sequences:

```
                               (SEQ ID NO: 1)
CDR-H1 GFTFSDYY (SEQ ID NO: 2)
CDR-H2 ISDGGSYT (SEQ ID NO: 3)
CDR-H3 ARDYYGSSSYTSGFAY (SEQ ID NO: 4)
CDR-L1 QSLLNSRTRKNY (SEQ ID NO: 5)
CDR-L2 WAS (SEQ ID NO: 6)
CDR-L3 KQSYNLYT
```

In an embodiment, the antibody comprises a heavy chain variable region comprising: i) an amino acid sequence as set forth in SEQ ID NO: 9; ii) an amino acid sequence with at least 50%, at least 60%, at least 70%, at least 80%, or at least 90% sequence identity to SEQ ID NO: 9, wherein the CDR sequences are as set forth in SEQ ID NO: 1, 2 and 3, or iii) a conservatively substituted amino acid sequence i) wherein the CDR sequences are as set forth in SEQ ID NO: 1, 2 and 3.

In another embodiment, the antibody comprises a light chain variable region comprising i) an amino acid sequence as set forth in SEQ ID NO: 11, ii) an amino acid sequence with at least 50%, at least 60%, at least 70%, at least 80%, or at least 90% sequence identity to SEQ ID NO: 11, wherein the CDR sequences are as set forth in SEQ ID NO: 4, 5 and 6, or iii) a conservatively substituted amino acid sequence of i) wherein the CDR sequences are as set forth in SEQ ID NO: 4, 5 and 6.

In another embodiment, the heavy chain variable region amino acid sequence is encoded by a nucleotide sequence as set forth in SEQ ID NO: 8 or a codon degenerate or optimized version thereof; and/or the antibody comprises a light chain variable region amino acid sequence encoded by a nucleotide sequence as set out in SEQ ID NO: 10 or a codon degenerate or optimized version thereof.

In another embodiment, the heavy chain variable region comprises or consists of an amino acid sequence as set forth in SEQ ID NO: 9 and/or the light chain variable region comprises or consists of an amino acid sequence as set forth in SEQ ID NO: 11.

In another embodiment, the antibody is an antibody that competes for binding to a cyclic peptide having sequence of SEQ ID NO: 12, and/or to human A-beta oligomers with an antibody comprising the CDR sequences as recited herein in SEQ ID NOs: 1-6.

In another embodiment, the antibody a cyclic peptide having sequence of SEQ ID NO: 12, and/or human A-beta oligomers with an antibody comprising the heavy chain variable chain sequence of SEQ ID NO: 9 and/or the light chain variable region sequence of SEQ ID NO: 11.

Another aspect includes an isolated conformation specific and/or selective antibody comprising a light chain variable region and a heavy chain variable region, optionally fused, the heavy chain variable region comprising complementarity determining regions CDR-H1, CDR-H2 and CDR-H3, the light chain variable region comprising complementarity determining region CDR-L1, CDR-L2 and CDR-L3 and with the amino acid sequences of said CDRs comprising the sequences:

```
                               (SEQ ID NO: 1)
CDR-H1 GFTFSDYY (SEQ ID NO: 2)
CDR-H2 ISDGGSYT (SEQ ID NO: 80)
CDR-H3 ARDYYGSNSYTSGFAY (SEQ ID NO: 4)
CDR-L1 QSLLNSRTRKNY (SEQ ID NO: 5)
CDR-L2 WAS (SEQ ID NO: 6)
CDR-L3 KQSYNLYT.
```

In an embodiment, the antibody comprises a heavy chain variable region comprising: i) an amino acid sequence as set forth in SEQ ID NO: 85; ii) an amino acid sequence with at least 50%, at least 60%, at least 70%, at least 80%, or at least 90% sequence identity to SEQ ID NO: 85, wherein the CDR sequences are as set forth in SEQ ID NO: 1, 2 and 80, or iii) a conservatively substituted amino acid sequence i) wherein the CDR sequences are as set forth in SEQ ID NO: 1, 2 and 80.

In another embodiment, the antibody comprises a light chain variable region comprising i) an amino acid sequence as set forth in SEQ ID NO: 87, ii) an amino acid sequence with at least 50%, at least 60%, at least 70%, at least 80%, or at least 90% sequence identity to SEQ ID NO: 89, wherein the CDR sequences are as set forth in SEQ ID NO: 4, 5 and 6, or iii) a conservatively substituted amino acid sequence of i) wherein the CDR sequences are as set forth in SEQ ID NO: 4, 5 and 6.

In another embodiment, the heavy chain variable region amino acid sequence is encoded by a nucleotide sequence as set forth in SEQ ID NO: 84 or a codon degenerate or optimized version thereof; and/or the antibody comprises a light chain variable region amino acid sequence encoded by a nucleotide sequence as set out in SEQ ID NO: 86 or a codon degenerate or optimized version thereof.

In another embodiment, the heavy chain variable region comprises or consists of an amino acid sequence as set forth in SEQ ID NO: 85 and/or the light chain variable region comprises or consists of an amino acid sequence as set forth in SEQ ID NO: 87.

In another embodiment, the antibody is an antibody that competes for binding to a cyclic peptide having sequence of SEQ ID NO: 12, and/or human A-beta oligomers with an antibody comprising the CDR sequences as recited herein in SEQ ID NOs: 1, 2, 80, 4-6.

In another embodiment, the antibody is an antibody that binds a cyclic peptide having sequence of SEQ ID NO: 12, and/or human A-beta oligomers with an antibody comprising the heavy chain variable chain sequence of SEQ ID NO: 85 and/or the light chain variable region sequence of SEQ ID NO: 87.

Another aspect includes an isolated conformation specific and/or selective antibody comprising a light chain variable region and a heavy chain variable region, optionally fused, the heavy chain variable region comprising complementarity determining regions CDR-H1, CDR-H2 and CDR-H3, the light chain variable region comprising complementarity determining region CDR-L1, CDR-L2 and CDR-L3 and with the amino acid sequences of said CDRs comprising the sequences:

```
                            (SEQ ID NO: 1)
CDR-H1 GFTFSDYY (SEQ ID NO: 2)
CDR-H2 ISDGGSYT (SEQ ID NO: 80)
CDR-H3 ARDYYGSNSYTSGFAY (SEQ ID NO: 81)
CDR-L1 QSIVHSNGNTY (SEQ ID NO: 82)
CDR-L2 KVS (SEQ ID NO: 83)
CDR-L3 FQGSHVPLT.
```

In an embodiment, the antibody comprises a heavy chain variable region comprising: i) an amino acid sequence as set forth in SEQ ID NO: 85; ii) an amino acid sequence with at least 50%, at least 60%, at least 70%, at least 80%, or at least 90% sequence identity to SEQ ID NO: 85, wherein the CDR sequences are as set forth in SEQ ID NO: 1, 2 and 80, or iii) a conservatively substituted amino acid sequence i) wherein the CDR sequences are as set forth in SEQ ID NO: 1, 2 and 80.

In another embodiment, the antibody comprises a light chain variable region comprising i) an amino acid sequence as set forth in SEQ ID NO: 89, ii) an amino acid sequence with at least 50%, at least 60%, at least 70%, at least 80%, or at least 90% sequence identity to SEQ ID NO: 89, wherein the CDR sequences are as set forth in SEQ ID NO: 81, 82 and 83, or iii) a conservatively substituted amino acid sequence of i) wherein the CDR sequences are as set forth in SEQ ID NO: 81, 82 and 83.

In another embodiment, the heavy chain variable region amino acid sequence is encoded by a nucleotide sequence as set forth in SEQ ID NO: 84 or a codon degenerate or optimized version thereof; and/or the antibody comprises a light chain variable region amino acid sequence encoded by a nucleotide sequence as set out in SEQ ID NO: 88 or a codon degenerate or optimized version thereof.

In another embodiment, the heavy chain variable region comprises or consists of an amino acid sequence as set forth in SEQ ID NO: 85 and/or the light chain variable region comprises or consists of an amino acid sequence as set forth in SEQ ID NO: 89.

In another embodiment, the antibody is an antibody that competes for binding to a cyclic peptide having sequence of SEQ ID NO: 12, and/or human A-beta oligomers with an antibody comprising the CDR sequences as recited herein in SEQ ID NOs: 1, 2, 80-3.

In another embodiment, the antibody is an antibody that binds a cyclic peptide having sequence of SEQ ID NO: 12, and/or human A-beta oligomers with an antibody comprising the heavy chain variable chain sequence of SEQ ID NO: 85 and/or the light chain variable region sequence of SEQ ID NO: 89.

In an embodiment, the antibody lacks binding a linear peptide comprising the sequence HHQK (SEQ ID NO: 7), optionally wherein the sequence of the linear peptide is a linear version of a cyclic sequence used to raise the antibody, optionally under conditions described in the Examples.

In an embodiment, the antibody specifically binds an epitope on A-beta as present in vivo, the epitope comprising or consisting HHQK (SEQ ID NO: 7), or a part thereof.

In an embodiment, the antibody does not specifically bind and/or is not selective for linear peptides consisting of HHQK (SEQ ID NO: 7). Selective binding can be measured using an ELISA or surface plasmon resonance measurement, as described herein.

In an embodiment, the antibody selectively binds a cyclic compound comprising HHQK (SEQ ID NO: 7) or a part thereof, optionally in the context of cyclo(CGHHQKG) (SEQ ID NO: 12) relative to a linear peptide comprising HHQK (SEQ ID NO: 7), optionally in the context of linear CGHHQKG (SEQ ID NO: 12). For example, in an embodiment the antibody selectively binds HHQK (SEQ ID NO: 7) in a cyclic conformation and has at least 2 fold, at least 5 fold, at least 10 fold at least 20 fold, at least 30 fold, at least 40 fold, at least 50 fold, at least 100 fold, at least 500 fold, at least 1000 fold more selective for HHQK (SEQ ID NO: 7) in the cyclic conformation compared to HHQK (SEQ ID NO: 7) in a linear compound such as a corresponding linear compound, for example as measured by ELISA or surface plasmon resonance, optionally using a method described herein.

In an embodiment, the antibody selectively binds a cyclic compound comprising the epitope sequence relative to linear peptide or a species of A-beta such as A-beta oligomer relative to monomer. In an embodiment, the selectivity is at least 2 fold, at least 3 fold, at least 5 fold, at least 10 fold, at least 20 fold, at least 30 fold, at least 40 fold, at least 50 fold, at least 100 fold, at least 500 fold, at least 1000 fold more selective for the cyclic compound and/or A-beta oligomer over a species of A-beta selected from A-beta monomer and/or A-beta fibril and/or linear HHQK (SEQ ID NO: 7), optionally linear CGHHQKG (SEQ ID NO: 12).

In an embodiment, the antibody is a monoclonal antibody. The production of monoclonals is described in the Examples.

To produce monoclonal antibodies, antibody producing cells (lymphocytes) can be harvested from a subject immunized with an immunogen described herein, and fused with myeloma cells by standard somatic cell fusion procedures thus immortalizing these cells and yielding hybridoma cells. Such techniques are well known in the art, (e.g. the hybridoma technique originally developed by Kohler and Milstein (Nature 256:495-497 (1975)) as well as other techniques such as the human B-cell hybridoma technique (Kozbor et al., Immunol. Today 4:72 (1983)), the EBV-hybridoma technique to produce human monoclonal antibodies (Cole et al., Methods Enzymol, 121: 140-67 (1986)), and screening of combinatorial antibody libraries (Huse et al., Science 246:1275 (1989)). Hybridoma cells can be screened immunochemically for production of antibodies specifically reactive with the desired epitopes and the monoclonal antibodies can be isolated.

Specific antibodies, or antibody fragments, reactive against particular antigens or molecules, may also be generated by screening expression libraries encoding immunoglobulin genes, or portions thereof, expressed in bacteria with cell surface components. For example, complete Fab fragments, VH regions and FV regions can be expressed in bacteria using phage expression libraries (see for example Ward et al., Nature 41:544-546 (1989); Huse et al., Science 246:1275-1281 (1989); and McCafferty et al., Nature 348: 552-554 (1990).

In an embodiment, the antibody is a humanized antibody. As demonstrated in the Examples, specific humanized antibodies are described.

The humanization of antibodies from non-human species has been well described in the literature. See for example EP-B1 0 239400 and Carter & Merchant 1997 (Curr Opin Biotechnol 8, 449-454, 1997 incorporated by reference in their entirety herein). Humanized antibodies are also readily obtained commercially (eg. Scotgen Limited, 2 Holly Road, Twickenham, Middlesex, Great Britain.).

Humanized forms of rodent antibodies are readily generated by CDR grafting (Riechmann et al. Nature, 332:323-327, 1988). In this approach the six CDR loops comprising the antigen binding site of the rodent monoclonal antibody are linked to corresponding human framework regions. CDR grafting often yields antibodies with reduced affinity as the amino acids of the framework regions may influence antigen recognition (Foote & Winter. J Mol Biol, 224: 487-499, 1992). To maintain the affinity of the antibody, it is often necessary to replace certain framework residues by site directed mutagenesis or other recombinant techniques and may be aided by computer modeling of the antigen binding site (Co et al. J Immunol, 152: 2968-2976, 1994).

Humanized forms of antibodies are optionally obtained by resurfacing (Pedersen et al. J Mol Biol, 235: 959-973, 1994). In this approach only the surface residues of a rodent antibody are humanized.

In an embodiment, the humanized antibody comprises CDRS as shown in Table 2.

Specific humanized sequences are provided in Tables 4A and 4B.

An aspect includes a humanized antibody comprising a sequence as set forth in Table 4A or 4B or having a sequence with at least 50% sequence identity a sequence as set forth in Table 4A or 4B wherein the CDR amino acid sequences are as shown therein.

In an embodiment, the humanized antibody comprises a heavy chain variable region comprising: i) an amino acid sequence as set forth in any one of SEQ ID NO: 16, 18, 20, 22, 24 and 26; ii) an amino acid sequence with at least 50%, at least 60%, at least 70%, at least 80%, or at least 90% sequence identity to any one of SEQ ID NO: 16, 18, 20, 22, 24 and 26, wherein the CDR sequences are as set forth in SEQ ID NO: 1, 2 and 3, or iii) a conservatively substituted amino acid sequence i) wherein the CDR sequences are as set forth in SEQ ID NO: 1, 2 and 3.

In another embodiment, the antibody comprises a light chain variable region comprising i) an amino acid sequence as set forth any one of SEQ ID NO: 30, 32, 34, 36, 38 and 40, ii) an amino acid sequence with at least 50%, at least 60%, at least 70%, at least 80%, or at least 90% sequence identity to any one of SEQ ID NO: 30, 32, 34, 36, 38 and 40, wherein the CDR sequences are as set forth in SEQ ID NO: 4, 5 and 6, or iii) a conservatively substituted amino acid sequence of i) wherein the CDR sequences are as set forth in SEQ ID NO: 4, 5 and 6.

In another embodiment, the heavy chain variable region amino acid sequence is encoded by a nucleotide sequence as set forth in any one of SEQ ID NO: 15, 17, 19, 21, 23 and 25 or a codon degenerate or optimized version thereof; and/or the antibody comprises a light chain variable region amino acid sequence encoded by a nucleotide sequence as set out in any one of SEQ ID NO: 29, 31, 33, 35, 37 and 39 or a codon degenerate or optimized version thereof.

In another embodiment, the heavy chain variable region comprises or consists of an amino acid sequence as set forth in any one of SEQ ID NO: 16, 18, 20, 22, 24 and 26 and/or the light chain variable region comprises or consists of an amino acid sequence as set forth in SEQ ID any one of SEQ ID NO: 30, 32, 34, 36, 38 and 40.

In another embodiment, the antibody is an antibody that competes for binding to a cyclic peptide having sequence of SEQ ID NO: 12, and/or human A-beta optionally human A-beta oligomers with an antibody comprising the heavy chain sequence as shown in Table 4A, optionally comprising a light chain sequence shown in Table 4A.

In another embodiment, the antibody is an antibody that competes for binding to a cyclic peptide having sequence of SEQ ID NO: 12, and/or human A-beta, optionally human A-beta oligomers with an antibody comprising the heavy chain variable chain sequence in any one of SEQ ID NO: 16, 18, 20, 22, 24 and 26 and/or the light chain variable region sequence as set forth in SEQ ID any one of SEQ ID NO: 30, 32, 34, 36, 38 and 40.

In an embodiment, the antibody comprises SEQ ID NO: 16 and 30; SEQ ID NO: 18 and 32; SEQ ID NO: 20 and 34; SEQ ID NO: 22 and 36; SEQ ID NO: 24 and 38; or SEQ ID NO: 36 and 40, or sequences with sequence with at least 50%, at least 60%, at least 70%, at least 80%, or at least 90% sequence identity thereto wherein the CDRs are maintained as shown in Table 2.

In another embodiment, the humanized antibody comprises a sequence as shown in Table 4B.

In an embodiment, the humanized antibody comprises a heavy chain variable region comprising: i) an amino acid sequence as set forth in any one of SEQ ID NO: 44, 46, 48, 50, 52 and 54; ii) an amino acid sequence with at least 50%, at least 60%, at least 70%, at least 80%, or at least 90% sequence identity to any one of SEQ ID NO: 44, 46, 48, 50, 52 and 54, wherein the CDR sequences are the sequences shown underlined therein (also in SEQ ID NO: 74-76), or iii) a conservatively substituted amino acid sequence of i) wherein the CDR sequences are the sequences shown underlined therein (e.g. SEQ ID NO: 74-76).

In another embodiment, the antibody comprises a light chain variable region comprising i) an amino acid sequence as set forth any one of SEQ ID NO: 58, 60, 62, 64, 66 and 68, ii) an amino acid sequence with at least 50%, at least 60%, at least 70%, at least 80%, or at least 90% sequence identity to any one of SEQ ID NO: 58, 60, 62, 64, 66 and 68, wherein the CDR sequences are the sequences shown underlined therein (also in SEQ ID NOs:77-79), or iii) a conservatively substituted amino acid sequence of i) wherein the CDR sequences are the sequences shown underlined therein (also in SEQ ID NOs:77-79).

In another embodiment, the heavy chain variable region amino acid sequence is encoded by a nucleotide sequence as set forth in any one of SEQ ID NO: 43, 45, 47, 49, 51 and 53; or a codon degenerate or optimized version thereof; and/or the antibody comprises a light chain variable region amino acid sequence encoded by a nucleotide sequence as set out in any one of SEQ ID NO: 57, 59, 61, 63, 65 and 67 or a codon degenerate or optimized version thereof.

In another embodiment, the heavy chain variable region comprises or consists of an amino acid sequence as set forth in any one of SEQ ID NO: 44, 46, 48, 50, 52 and 54 and/or the light chain variable region comprises or consists of an amino acid sequence as set forth in SEQ ID any one of SEQ ID NO: 58, 60, 62, 64, 66 and 68.

In another embodiment, the antibody is an antibody that competes for binding to a cyclic peptide having sequence of SEQ ID NO: 12, and/or human A-beta oligomers with an antibody comprising the heavy chain sequence as shown in Table 4B, optionally wherein the antibody further comprises a light chain sequence shown in Table 4B.

In another embodiment, the antibody is an antibody that competes for binding to a cyclic peptide having sequence to SEQ ID NO: 12, and/or human A-beta oligomers with an antibody comprising the heavy chain variable chain sequence of any one of SEQ ID NO: 44, 46, 48, 50, 52 and 54 and/or the light chain variable region sequence of any one of SEQ ID NO: 58, 60, 62, 64, 66 and 68.

In an embodiment, the antibody comprises SEQ ID NO: 44 and 58; SEQ ID NO: 46 and 60; SEQ ID NO: 48 and 62; SEQ ID NO: 50 and 64; SEQ ID NO: 52 and 66; or SEQ ID NO: 54 and 68, or sequences with sequence with at least 50%, at least 60%, at least 70%, at least 80%, or at least 90% sequence identity thereto wherein the CDRs are maintained as shown underlined therein (also in in SEQ ID NOs:74-79).

In an embodiment, an antibody described herein comprises a constant region having i) an amino acid sequence as set forth in SEQ ID NO:70 and/or 72; ii) an amino acid sequence with at least 50%, at least 60%, at least 70%, at least 80%, or at least 90% sequence identity to any one of SEQ ID NO:70 and/or 72; or iii) a conservatively substituted amino acid sequence i).

In another embodiment, the heavy chain constant region amino acid sequence is encoded by a nucleotide sequence as set forth in SEQ ID NO: 69; or a codon degenerate or optimized version thereof; and/or the antibody comprises a light chain constant region amino acid sequence encoded by a nucleotide sequence as set out in SEQ ID NO:71, or a codon degenerate or optimized version thereof.

Human antibodies specific to a particular antigen may be identified by a phage display strategy (Jespers et al. Bio/Technology, 12: 899-903, 1994). In one approach, the heavy chain of a rodent antibody directed against a specific antigen is cloned and paired with a repertoire of human light chains for display as Fab fragments on filamentous phage. The phage is selected by binding to antigen. The selected human light chain is subsequently paired with a repertoire of human heavy chains for display on phage, and the phage is again selected by binding to antigen. The result is a human antibody Fab fragment specific to a particular antigen. In another approach, libraries of phage are produced where members display different human antibody fragments (Fab or Fv) on their outer surfaces (Dower et al., WO 91/17271 and McCafferty et al., WO 92/01047). Phage displaying antibodies with a desired specificity are selected by affinity enrichment to a specific antigen. The human Fab or Fv fragment identified from either approach may be recloned for expression as a human antibody in mammalian cells.

Human antibodies are optionally obtained from transgenic animals (U.S. Pat. Nos. 6,150,584; 6,114,598; and 5,770,429). In this approach the heavy chain joining region (JH) gene in a chimeric or germ-line mutant mouse is deleted. Human germ-line immunoglobulin gene array is subsequently transferred to such mutant mice. The resulting transgenic mouse is then capable of generating a full repertoire of human antibodies upon antigen challenge.

Humanized antibodies are typically produced as antigen binding fragments such as Fab, Fab' F(ab')2, Fd, Fv and single domain antibody fragments, or as single chain antibodies in which the heavy and light chains are linked by a spacer. Also, the human or humanized antibodies may exist in monomeric or polymeric form. The humanized antibody optionally comprises one non-human chain and one humanized chain (i.e. one humanized heavy or light chain).

Antibodies including humanized or human antibodies are selected from any class of immunoglobulins including: IgM, IgG, IgD, IgA or IgE; and any isotype, including: IgG1, IgG2, IgG3 and IgG4. The humanized or human antibody may include sequences from one or more than one isotype or class.

Antibodies having the CDRs shown in SEQ ID NOs: 74-79 were codon optimized and made to IgG1 or IgG2a isotype. Sequences are shown in Table 8.

In an embodiment, the antibody has a sequence or a part thereof as provided in Table 8, the part comprising at least the CDRs, optionally the heavy chain CDRs and/or the light chain CDRs. In an embodiment, the part is the variable chain portion of a sequence selected from the sequences in Table 8.

The constant region shown in Table 8 (for example determinable by comparing to other sequences provided herein such as SEQ ID NOs: 42 and 56 can also be combined with the variable sequences of antibodies with CDRS having SEQ ID NOs:1-6, or 1, 2, 80, 4-6 or 1, 2, 80-83.

Additionally, antibodies specific for the epitopes described herein are readily isolated by screening antibody phage display libraries. For example, an antibody phage library is optionally screened by using a disease specific epitope of the current invention to identify antibody fragments specific for the disease specific epitope. Antibody fragments identified are optionally used to produce a variety of recombinant antibodies that are useful with different embodiments of the present invention. Antibody phage display libraries are commercially available, for example, through Xoma (Berkeley, Calif.) Methods for screening antibody phage libraries are well known in the art.

In an embodiment, the antibody is a monoclonal antibody. In an embodiment, the antibody is a chimeric antibody such as a humanized antibody comprising the CDR sequences as recited in Table 2.

Also provided in another embodiment, is an antibody comprising CDRs as listed in Table 2 and a light chain variable region and a heavy chain variable region, optionally in the context of a single chain antibody.

The antibodies herein can be single chain antibodies. The humanized antibodies described are also in an embodiment, single chain antibodies.

As mentioned also included are antibodies that compete for binding to a cyclic peptide having sequence of SEQ ID NO: 12, and/or human A-beta oligomers with an antibody comprising the CDR sequences as recited in Table 2, or comprising a sequence as provided in any one of Tables 3, 4A, 4B and 8.

Competition between antibodies can be determined for example using an assay in which an antibody under test is assessed for its ability to inhibit specific binding of a reference antibody to the common antigen. A test antibody competes with a reference antibody if an excess of a test antibody (e.g., at least a 2 fold, 5, fold, 10 fold or 20 fold) inhibits binding of the reference antibody by at least 50%, at least 75%, at least 80%, at least 90% or at least 95% as measured in a competitive binding assay.

In an embodiment the antibody is isolated. In an embodiment, the antibody is an exogenous antibody.

In an embodiment, the antibody does not bind monomeric A-beta, for example under conditions described in the Examples. In an embodiment, the antibody does not bind A-beta in senile plaques, for example in situ in AD brain tissue, for example under conditions described in the Examples.

In another embodiment, the antibody does not selectively bind monomeric A-beta compared to native- or synthetic-oligomeric A-beta.

In an embodiment, the A-beta oligomer comprises A-beta 1-42 subunits.

In an embodiment, the antibody lacks A-beta fibril plaque (also referred to as senile plaque) staining, for example as measured by immuohistochemistry. Absence of plaque staining can be assessed by comparing to a positive control such as A-beta-specific antibodies 6E10 and 4G8 (Biolegend, San Diego, Calif.), or 2C8 (Enzo Life Sciences Inc., Farmingdale, N.Y.) and an isotype control. An antibody described herein lacks or has negligible A-beta fibril plaque staining if the antibody does not show typical plaque morphology staining and the level of staining is comparable to or no more than 2 fold the level seen with an IgG negative isotype control. The scale can for example set the level of staining with isotype control at 1 and with 6E10 at 10. An antibody lacks A-beta fibril plaque staining if the level of staining on such a scale is 2 or less. In embodiment, the antibody shows minimal A-beta fibril plaque staining, for example on the foregoing scale, levels scored at less about or less than 3.

A further aspect is an antibody conjugated to a therapeutic, detectable label or cytotoxic agent. In an embodiment, the detectable label is a positron-emitting radionuclide. A positron-emitting radionuclide can be used for example in PET imaging.

A further aspect relates to an antibody complex comprising an antibody described herein and/or a binding fragment thereof and oligomeric A-beta.

A further aspect is an isolated nucleic acid encoding an antibody or part thereof described herein.

Nucleic acids encoding a heavy chain or a light chain or parts thereof are also provided, for example encoding a heavy chain comprising CDR-H1, CDR-H2 and/or CDR-H3 regions described herein or encoding a light chain comprising CDR-L1, CDR-L2 and/or CDR-L3 regions described herein, variable chains described herein and codon optimized and codon degenerate versions thereof.

The present disclosure also provides variants of the nucleic acid sequences that encode for the antibody and/or binding fragment thereof disclosed herein. For example, the variants include nucleotide sequences that hybridize to the nucleic acid sequences encoding the antibody and/or binding fragment thereof disclosed herein under at least moderately stringent hybridization conditions or codon degenerate or optimized sequences. In another embodiment, the variant nucleic acid sequences have at least 50%, at least 60%, at least 70%, most preferably at least 80%, even more preferably at least 90% and even most preferably at least 95% sequence identity to nucleic acid sequences encoding any of the amino acid sequences shown in Tables 2, 3, 4A, 4B and 8.

A further aspect is an isolated nucleic acid encoding an antibody described herein, for example the nucleic acids shown in any of Tables 2, 3, 4A, 4B and 8.

Another aspect is an expression cassette or vector comprising the nucleic acid herein disclosed. In an embodiment, the vector is an isolated vector.

The vector can be any vector, including vectors suitable for producing an antibody and/or binding fragment thereof or expressing a peptide sequence described herein.

The nucleic acid molecules may be incorporated in a known manner into an appropriate expression vector which ensures expression of the protein. Possible expression vectors include but are not limited to cosmids, plasmids, or modified viruses (e.g. replication defective retroviruses, adenoviruses and adeno-associated viruses). The vector should be compatible with the host cell used. The expression vectors are "suitable for transformation of a host cell", which means that the expression vectors contain a nucleic acid molecule encoding the peptides corresponding to epitopes or antibodies described herein.

In an embodiment, the vector is suitable for expressing for example single chain antibodies by gene therapy. The vector can be adapted for specific expression in neural tissue, for example using neural specific promoters and the like. In an embodiment, the vector comprises an IRES and allows for expression of a light chain variable region and a heavy chain variable region. Such vectors can be used to deliver antibody in vivo.

Suitable regulatory sequences may be derived from a variety of sources, including bacterial, fungal, viral, mammalian, or insect genes.

Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

In an embodiment, the regulatory sequences direct or increase expression in neural tissue and/or cells.

In an embodiment, the vector is a viral vector.

The recombinant expression vectors may also contain a marker gene which facilitates the selection of host cells transformed, infected or transfected with a vector for expressing an antibody or epitope peptide described herein.

The recombinant expression vectors may also contain expression cassettes which encode a fusion moiety (i.e. a "fusion protein") which provides increased expression or stability of the recombinant peptide; increased solubility of the recombinant peptide; and aid in the purification of the target recombinant peptide by acting as a ligand in affinity purification, including for example tags and labels described herein. Further, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-transferase (GST), maltose E binding protein, or protein A, respectively, to the recombinant protein.

Systems for the transfer of genes for example into neurons and neural tissue both in vitro and in vivo include vectors based on viruses, most notably Herpes Simplex Virus, Adenovirus, Adeno-associated virus (AAV) and retroviruses including lentiviruses. Alternative approaches for gene delivery include the use of naked, plasmid DNA as well as liposome-DNA complexes. Another approach is the use of AAV plasmids in which the DNA is polycation-condensed and lipid entrapped and introduced into the brain by intracerebral gene delivery (Leone et al. US Application No. 2002076394).

Accordingly, in another aspect, the compounds, immunogens, nucleic acids, vectors and antibodies described herein may be formulated in vesicles such as liposomes, nanoparticles, and viral protein particles, for example for delivery of antibodies, compounds, immunogens and nucleic acids described herein. In particular synthetic polymer vesicles, including polymersomes, can be used to administer antibodies.

Also provided in another aspect is a cell, optionally an isolated and/or recombinant cell, expressing an antibody described herein or comprising a vector herein disclosed.

The recombinant cell can be generated using any cell suitable for producing a polypeptide, for example suitable for producing an antibody and/or binding fragment thereof. For example to introduce a nucleic acid (e.g. a vector) into a cell, the cell may be transfected, transformed or infected, depending upon the vector employed.

Suitable host cells include a wide variety of prokaryotic and eukaryotic host cells. For example, the proteins described herein may be expressed in bacterial cells such as *E. coli*, insect cells (using baculovirus), yeast cells or mammalian cells.

In an embodiment, the cell is a eukaryotic cell selected from a yeast, plant, worm, insect, avian, fish, reptile and mammalian cell.

In another embodiment, the mammalian cell is a myeloma cell, a spleen cell, or a hybridoma cell.

In an embodiment, the cell is a neural cell.

Yeast and fungi host cells suitable for expressing an antibody or peptide include, but are not limited to *Saccharomyces cerevisiae, Schizosaccharomyces pombe*, the genera *Pichia* or *Kluyveromyces* and various species of the genus *Aspergillus*. Examples of vectors for expression in yeast *S. cerivisiae* include pYepSec1, pMFa, pJRY88, and pYES2 (Invitrogen Corporation, San Diego, Calif.). Protocols for the transformation of yeast and fungi are well known to those of ordinary skill in the art.

Mammalian cells that may be suitable include, among others: COS (e.g., ATCC No. CRL 1650 or 1651), BHK (e.g. ATCC No. CRL 6281), CHO (ATCC No. CCL 61), HeLa (e.g., ATCC No. CCL 2), 293 (ATCC No. 1573) and NS-1 cells. Suitable expression vectors for directing expression in mammalian cells generally include a promoter (e.g., derived from viral material such as polyoma, Adenovirus 2, cytomegalovirus and Simian Virus 40), as well as other transcriptional and translational control sequences. Examples of mammalian expression vectors include pCDM8 and pMT2PC.

In an embodiment, the cell is a fused cell such as a hybridoma cell, the hybridoma cell producing an antibody specific and/or selective for an epitope or epitope sequence described herein, including for example that selectively binds A-beta oligomers over A-beta monomers, selectively binds an epitope sequence presented in a cyclic compound relative to a linear compound or lacks or has negligible plaque binding.

A further aspect is a hybridoma cell line producing an antibody comprising the a CDR set described herein.

III. Compositions

A further aspect is a composition comprising a nucleic acid, vector or antibody described herein.

In an embodiment, the composition comprises a diluent.

Suitable diluents for nucleic acids include but are not limited to water, saline solutions and ethanol.

Suitable diluents for polypeptides, including antibodies or fragments thereof and/or cells include but are not limited to saline solutions, pH buffered solutions and glycerol solutions or other solutions suitable for freezing polypeptides and/or cells.

In an embodiment, the composition is a pharmaceutical composition comprising any of the antibodies, nucleic acids or vectors disclosed herein, and optionally comprising a pharmaceutically acceptable carrier.

The compositions described herein can be prepared by per se known methods for the preparation of pharmaceutically acceptable compositions that can be administered to subjects, optionally as a vaccine, such that an effective quantity of the active substance is combined in a mixture with a pharmaceutically acceptable vehicle.

Pharmaceutical compositions include, without limitation, lyophilized powders or aqueous or non-aqueous sterile injectable solutions or suspensions, which may further contain antioxidants, buffers, bacteriostats and solutes that render the compositions substantially compatible with the tissues or the blood of an intended recipient. Other components that may be present in such compositions include water, surfactants (such as Tween), alcohols, polyols, glycerin and vegetable oils, for example. Extemporaneous injection solutions and suspensions may be prepared from sterile powders, granules, tablets, or concentrated solutions or suspensions. The composition may be supplied, for example but not by way of limitation, as a lyophilized powder which is reconstituted with sterile water or saline prior to administration to the patient.

Pharmaceutical compositions may comprise a pharmaceutically acceptable carrier. Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, ethanol, N-(1(2,3-dioleyloxy)propyl)N, N,N-trimethylammonium chloride (DOTMA), diolesylphosphotidyl-ethanolamine (DOPE), and liposomes. Such compositions should contain a therapeutically effective amount of the compound, together with a suitable amount of carrier so as to provide the form for direct administration to the patient.

The composition may be in the form of a pharmaceutically acceptable salt which includes, without limitation, those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, In an embodiment, the composition comprises an antibody described herein. In another embodiment, the composition comprises an antibody described herein and a diluent. In an embodiment, the composition is a sterile composition.

A further aspect includes an antibody complex comprising an antibody described herein and A-beta, optionally A-beta oligomer. The complex may be in solution or comprised in a tissue, optionally in vitro.

IV. Kits

A further aspect relates to a kit comprising i) an antibody and/or binding fragment thereof, ii) a nucleic acid of said antibody or a part thereof, iii) composition comprising an antibody, nucleic acid or cell described herein or iv) a recombinant cell described herein, comprised in a vial such as a sterile vial or other housing and optionally a reference agent and/or instructions for use thereof.

In an embodiment, the kit further comprises one or more of a collection vial, standard buffer and detection reagent.

In another embodiment, the kit is for diagnosing or monitoring Alzheimer's disease or a condition involving oligomeric Abeta.

V. Methods

Included are methods for making the antibodies described herein.

In particular, provided are methods of making an antibody an antibody described herein selective for a conformational epitope of HHQK (SEQ ID NO: 7) using an antibody described herein, the method comprising administering to a subject, optionally a non-human subject, a cyclic compound comprising an epitope sequence described herein, and isolating antibody producing cells or antibodies that comprise the CDRs described herein.

In an embodiment, the method is for making a monoclonal antibody using for example a method as described herein.

In another embodiment, a method of making a chimeric antibody or binding fragment thereof is provided, the method comprising using recombinant technology to subcloning a nucleic acid encoding the variable region of an antibody (heavy and/or light) described herein into a vector comprising a nucleic acid encoding a human antibody constant domain (e.g. IgG1, 2, 3, or 4), optionally with or without the Fc portion to produce a chimeric antibody vector; and expressing the chimeric antibody vector in a cell; and isolating the antibody. In an embodiment, the chimera is a mouse human chimera.

In an embodiment, the method is for making a humanized antibody using for example a method described herein. In an embodiment, the method comprises making a chimeric intermediate. The variable regions of the chimeric intermediate are for example mutagenized to introduce one or more amino acid changes outside the CDR regions. In another embodiment, one or more CDR coding sequences described herein are inserted into a human antibody scaffold.

Antibodies produced using a cyclic compound are selected as described herein and in the Examples such. In an embodiment, the method comprises isolating antibodies that specifically or selectively bind cyclic peptide over linear peptide, are specific for the epitope sequence, specifically bind oligomer and/or lack or negligibly bind plaque in situ and/or corresponding linear peptide, optionally using a method described herein.

A further aspect provides a method of detecting whether a biological sample comprises A-beta the method comprising contacting the biological sample with an antibody described herein and/or detecting the presence of any antibody complex. In an embodiment, the method is for detecting whether a biological sample comprises oligomeric A-beta.

In an embodiment, the method comprises:
a. contacting the biologic sample with an antibody described herein that is specific and/or selective for A-beta oligomer herein under conditions permissive to produce an antibody: A-beta oligomer complex; and
b. detecting the presence of any complex;
wherein the presence of detectable complex is indicative that the sample may contain A-beta oligomer.

In an embodiment, the level of complex formed is compared to a test antibody such as a suitable Ig control or irrelevant antibody.

In an embodiment, the detection is quantitated and the amount of complex produced is measured. The measurement can for example be relative to a standard.

In an embodiment, the measured amount is compared to a control.

In another embodiment, the method comprises:
(a) contacting a test sample of said subject with an antibody described herein, under conditions permissive to produce an antibody-antigen complex;
(b) measuring the amount of the antibody-antigen complex in the test sample; and
(c) comparing the amount of antibody-antigen complex in the test sample to a control;
wherein detecting antibody-antigen complex in the test sample as compared to the control indicates that the sample comprises A-beta.

The control can be a sample control (e.g. from a subject without AD, or from a subject with a particular form of AD, mild, moderate or advanced), or be a previous sample from the same subject for monitoring changes in A-beta oligomer levels in the subject. Alternatively the control can be a value derived from a plurality of patients with or without AD.

In an embodiment, the antibody is an antibody having the CDR sequences described herein. In an embodiment, the antibody is a humanized antibody. In an embodiment, the antibody is a chimeric antibody.

In an embodiment, the sample is a biological sample. In an embodiment, the sample comprises brain tissue or an extract thereof and/or CSF. In an embodiment, the sample comprises whole blood, plasma or serum. In an embodiment, the sample is obtained from a human subject. In an embodiment, the subject is suspected of, at a risk of or has AD.

A number of methods can be used to detect an A-beta: antibody complex and thereby determine A-beta oligomers is present in a sample using the antibodies described herein, including immunoassays such as flow cytometry, Western blots, ELISA, SPR and immunoprecipitation followed by SDS-PAGE immunocytochemistry.

As described in the Examples surface plasmon resonance technology can be used to assess conformation specific binding. If the antibody is labeled or a detectably labeled secondary antibody specific for the complex antibody is used, the label can be detected. Commonly used reagents include fluorescent emitting and HRP labeled antibodies. In quantitative methods, the amount of signal produced can be measured by comparison to a standard or control. The measurement can also be relative.

A further aspect includes a method of measuring a level of or imaging A-beta in a subject or tissue, optionally where the A-beta to be measured or imaged is oligomeric A-beta. In an embodiment, the method comprises administering to a subject at risk or suspected of having or having AD, an antibody described herein conjugated to a detectable label; and detecting the label, optionally quantitatively detecting the label. The label in an embodiment is a positron emitting radionuclide which can for example be used in PET imaging.

The methods may also be combined with other tests for AD or cognitive impairment. For example, synaptic protein levels, such as SNAP-25 or synaptic vesicle glycoprotein 2a (SVG2a) (*Sci Transl Med.* 2016 Jul. 20; 8(348):348ra96. doi: 10.1126/scitranslmed.aaf6667) in CSF can be measured. For example, flourodeoxyglucose PET (FDG-PET) is used as an indirect measure of synaptic metabolism.

Detecting A-beta levels using an antibody described herein can be used alone or in combination with other methods to monitor response to treatment.

It is demonstrated herein that antibodies raised against cyclo(CGHHQKG) (SEQ ID NO: 12), comprising the CDR sets described herein can specifically and/or selectively bind A-beta oligomers. Oligomeric A-beta species are believed to be the toxic propagating species in AD. Further as shown in FIG. 1 and described in the Examples, these antibodies are specific for oligomers, inhibited A-beta aggregation and A-beta oligomer propagation. Accordingly, also provided are methods of inhibiting A-beta oligomer propagation, the method comprising contacting a cell or tissue expressing A-beta with or administering to a subject in need thereof an effective amount of an A-beta oligomer specific or selective antibody described herein to inhibit A-beta aggregation and/or oligomer propagation. In vitro the assay can be monitored as described in the Examples.

The antibodies may also be useful for treating AD and/or other A-beta amyloid related diseases. For example, variants of Lewy body dementia and in inclusion body myositis (a muscle disease) exhibit similar plaques as AD and A-beta can also form aggregates implicated in cerebral amyloid angiopathy. As mentioned, the antibodies comprising the CDR sets as well as when in the humanized antibodies sequences described herein bind oligomeric A-beta which is believed to be a toxigenic species of A-beta in AD and inhibit formation of toxigenic A-beta oligomers in vitro.

Accordingly a further aspect is a method of treating AD and/or other A-beta amyloid related diseases, the method comprising administering to a subject in need thereof an effective amount of an antibody described herein comprising a CDR set described herein, optionally a humanized antibody described in Table 4A or 4B or selective or a pharmaceutical composition comprising said antibody, to a subject in need thereof. In other embodiments, nucleic acids encoding the antibodies described herein can also be administered to the subject, optionally using vectors suitable for delivering nucleic acids in a subject.

In an embodiment, a biological sample from the subject to be treated is assessed for the presence or levels of A-beta using an antibody described herein. In an embodiment, a subject with detectable A-beta levels (e.g. A-beta antibody complexes measured in vitro or measured by imaging) is treated with the antibody.

The antibody, peptides and nucleic acids can for example be comprised in a pharmaceutical composition as described herein, and formulated for example in vesicles for improving delivery.

One or more antibodies targeting HHQK (SEQ ID NO: 7) can be administered in combination. In addition the antibodies disclosed herein can be administered with one or more other treatments such as a beta-secretase inhibitor or a cholinesterase inhibitor.

Also provided are uses of the compositions, antibodies, isolated peptides, and nucleic acids for treating AD or A-beta amyloid related diseases.

The compositions, antibodies, isolated peptides and nucleic acids, vectors etc. described herein can be administered for example, by parenteral, intravenous, subcutaneous, intramuscular, intracranial, intraventricular, intrathecal, intraorbital, ophthalmic, intraspinal, intracisternal, intraperitoneal, intranasal, aerosol or oral administration.

In certain embodiments, the pharmaceutical composition is administered systemically.

In other embodiments, the pharmaceutical composition is administered directly to the brain or other portion of the CNS. For example such methods include the use of an implantable catheter and a pump, which would serve to discharge a pre-determined dose through the catheter to the infusion site. A person skilled in the art would further recognize that the catheter may be implanted by surgical techniques that permit visualization of the catheter so as to position the catheter adjacent to the desired site of administration or infusion in the brain. Such techniques are described in Elsberry et al. U.S. Pat. No. 5,814,014 "Techniques of Treating Neurodegenerative Disorders by Brain Infusion", which is herein incorporated by reference. Also contemplated are methods such as those described in US patent application 20060129126 (Kaplitt and During "Infusion device and method for infusing material into the brain of a patient". Devices for delivering drugs to the brain and other parts of the CNS are commercially available (eg. an implantable infusion pump such as SynchroMed® EL Infusion System; Medtronic, Minneapolis, Minn.).

In another embodiment, the pharmaceutical composition is administered to the brain using methods such as modifying the compounds to be administered to allow receptor-mediated transport across the blood brain barrier.

Other embodiments contemplate the co-administration of the compositions, antibodies, isolated peptides and nucleic acids described herein with biologically active molecules known to facilitate the transport across the blood brain barrier.

Also contemplated in certain embodiments, are methods for administering the compositions, antibodies, isolated peptides, and nucleic acids described herein across the blood brain barrier such as those directed at transiently increasing the permeability of the blood brain barrier as described in U.S. Pat. No. 7,012,061 "Method for increasing the permeability of the blood brain barrier", herein incorporated by reference.

The above disclosure generally describes the present application. A more complete understanding can be obtained by reference to the following specific examples. These examples are described solely for the purpose of illustration and are not intended to limit the scope of the application. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1

Antibody Generation
Methods and Materials
Immunogen

Cyclo(CGHHQKG) (SEQ ID NO:12) peptide was generated at CPC Scientific, Sunnyvale, Calif., USA (both cyclic and linear), and conjugated to KLH (for immunizing) and BSA (for screening) using a trifluoroacetate counter ion protocol. A linear peptide of the same sequences, CGHHQKG (SEQ ID NO: 12), were also made. Peptides were desalted and checked by MS and HPLC and deemed 95% pure. The cyclopeptide was shipped to IPA for use in production of monoclonal antibodies in mice.

Antibodies

Hybridomas and monoclonal antibodies were generated to cyclo(CGHHQKG) (SEQ ID NO: 12) linked to Keyhole Limpet Hemocyanin (KLH).

Fifty day old female BALB/c mice (Charles River Laboratories, Quebec) were immunized. A series of subcutaneous aqueous injections containing antigen but no adjuvant were given over a period of 19 days. Mice were immunized with 100 µg per mouse per injection of a 0.5 mg/mL cyclic peptide-KLH solution in sterile saline. All 4 mice were euthanized on Day 19 and lymphocytes were harvested for hybridoma cell line generation.

Fusion/Hybridoma Development

Lymphocytes were isolated and fused with murine SP2/0 myeloma cells in the presence of poly-ethylene glycol (PEG 1500). Fused cells were cultured using HAT selection. This method uses a semi-solid methylcellulose-based HAT selective medium to combine the hybridoma selection and cloning into one step. Single cell-derived hybridomas grow to form monoclonal colonies on the semi-solid media. 10 days after the fusion event, resulting hybridoma clones were transferred to 96-well tissue culture plates and grown in HT containing medium until mid-log growth was reached (5 days).

Hybridoma Analysis

Tissue culture supernatants from the hybridomas were tested by indirect ELISA on screening antigen (cyclic peptide-BSA) and probed for both IgG and IgM antibodies using a Goat anti-IgG/IgM(H&L)-HRP secondary and developed with TMB substrate. Clones >0.2 OD in this assay were taken to the next round of testing. Positive cultures were retested on screening antigen to confirm secretion and on an irrelevant antigen (Human Transferrin) to eliminate non-specific mAbs and rule out false positives. Selected clones were isotyped by antibody trapping ELISA to determine if they are IgG or IgM isotype. Selected clones were also tested by indirect ELISA on other cyclic peptide-BSA conjugates as well as linear peptide-BSA conjugates to evaluate cross-reactivity and linker reactivity. Antibodies were also screened by SPR analysis.

ELISA Antibody Screening

ELISA plates were coated with 1) 0.1 ug/well cyclopeptide-conjugated-BSA at 100 uL/well in carbonate coating buffer (pH 9.6) O/N at 4 C; 2) 0.1 ug/well linear-peptide-conjugated-BSA at 100 uL/well in carbonate coating buffer (pH 9.6) O/N at 4 C; or 3) 0.1 ug/well Negative-Peptide at 100 uL/well in carbonate coating buffer (pH 9.6) O/N at 4 C. Primary Antibody: Hybridoma supernatant at 100 uL/well incubated for 1 hour at 37 C with shaking. Secondary Antibody 1:10,000 Goat anti-mouse IgG/IgM(H+L)-HRP at 100 uL/well in PBS-Tween for 1 hour at 37 C with shaking. All washing steps were performed for 30 mins with PBS-Tween. The substrate TMB was added at 50 uL/well, developed in the dark and stopped with equal volume 1M HCl.

SPR Binding Assays
SPR Analysis of Antibody Binding to Cyclic Peptides, A-Beta Monomers and Oligomers A-Beta Monomer and Oligomer Preparation:

Recombinant A-beta40 and 42 peptides (California Peptide, Salt Lake City Utah, USA) were dissolved in ice-cold hexafluoroisopropanol (HFIP). The HFIP was removed by evaporation overnight and dried in a SpeedVac centrifuge. To prepare monomers, the peptide film was reconstituted in DMSO to 5 mM, diluted further to 100 µM in dH2O and used immediately. Oligomers were prepared by diluting the 5 mM DMSO peptide solution in phenol red-free F12 medium (Life Technologies Inc., Burlington ON, Canada) to a final concentration of 100 µM and incubated for 24 hours to 7 days at 4° C.

SPR Analysis of Cyclic Peptide, A-Beta Monomer and Oligomer Binding:

All SPR measurements were performed using a Molecular Affinity Screening System (MASS-1) (Sierra Sensors GmbH, Hamburg, Germany), an analytical biosensor that employs high intensity laser light and high speed optical scanning to monitor binding interactions in real time. The primary screening of tissue culture supernatants was performed using an SPR direct binding assay, whereby BSA-conjugated peptides, A-beta42 Monomer and A-beta42 Oligomer are covalently immobilized on individual flow cells of a High Amine Capacity (HAC) sensorchip (Sierra Sensors GmbH, Hamburg, Germany) and antibodies flowed over the surface. Each sample was diluted and injected in duplicate over the immobilized peptide and BSA reference surfaces, followed by injection of running buffer only for the dissociation phase. After every analytical cycle, the sensor chip surfaces were regenerated. Sensorgrams were double-referenced by subtracting out binding from the BSA reference surfaces and blank running buffer injections, and binding response report points collected in the dissociation phase.

Protein G purified mAbs were analyzed in a secondary screen using an SPR indirect (capture) binding assay, whereby the antibodies were immobilized on a protein A-derivatized sensorchip (XanTec Bioanalytics GmbH, Duesseldorf, Germany) and A-beta40 Monomer, A-beta42 Oligomer, pooled soluble brain extracts flowed over the surface. The specificity of the antibodies was verified in an SPR direct binding assay by covalently immobilizing A-beta42 Monomer and A-beta42 Oligomer on individual flow cells of a HAC sensorchip and flowing purified mAbs over the surface.

Antibody Sequencing

The CDR and variable regions of the heavy and light chains were sequenced. Immunoglobulin gene transcripts expressed by the hybridomas were amplified from cDNA generated from the hybridoma cells using standard RT-PCR and sequenced using a standard dye-terminator capillary sequencing method.

Humanized Antibodies

Humanized Fab antibodies were prepared (Abzena) and sequenced.

Results

ELISA testing found that hybridoma clones bound the cyclopeptide preferentially over the linear peptide. Clones 301-3, 301-11 and 301-17 raised against cyclo(CGHHQKG) (SEQ ID NO: 12) were selected for further analysis.

Isotyping revealed 301-3, 301-11 and 301-17 were IgG3 subtypes.

Antibodies were tested in one or more assays for their ability to bind cyclic peptide, linear peptide, A-beta 1-42 monomer and A-beta 1-42 oligomers prepared as described above.

ELISA and SPR assays confirmed that the clones preferentially bound the cyclopeptide relative to the linear peptide (and were not cross reactive to unrelated cyclic peptides) and/or preferentially bound Aβ oligomers relative to monomers. The results of the binding analysis using SPR with hybridoma culture supernatants are shown in Table 1A.

Antibodies purified from the hybridoma supernatants were immobilized and assayed for their ability to bind Abeta oligomers by SPR. The results are shown in Table 1 B.

TABLE 1A

|  | Cyclic Peptide(RU) | Linear Peptide(RU) | Ab42 Monomer(RU) | Ab42 Oligomer(RU) |
|---|---|---|---|---|
| 301-11 | 488 | 210.5 | 21.6 | 75.3 |
| 301-3 | 468.9 | 60.6 | −1.8 | 56.8 |

TABLE 1B

|  | Ab42 Monomer (RU) | Ab42 Oligomer(RU) |
|---|---|---|
| 301-3 | −23.8 | 15.5 |
| 301-11 | −14.1 | −2.8 |
| 301-17 | −27.1 | 147.8 |

Antibody Sequence

Clones 301-3, 301-11 and 301-17 antibodies were sequenced. The CDR sequences of 301-3 and 301-11 are provided in Table 2. The CDRs for 301-17 are provided in SEQ ID Nos: 74-79. The consensus DNA sequence and polypeptide sequences of the variable portion of the heavy and light chain of the antibodies are provided in Table 3.

As shown in Table 2, the heavy chain CDRs for 301-3 and 301-11 were identical for CDRs 1 and 2 and CDR3 varied at one position.

Two light chains were sequenced. One light chain was near identical to the light chain for 301-11.

Humanized antibodies were prepared for 301-17 and sequenced (Abzena Cambridge UK). Humanized antibody sequences are provided in Table 4A (301-11) and 4B (301-17). The CDR sequences of each antibody sequences are bolded and underlined.

TABLE 2

| Antibody | Chain CDR | Sequence | SEQ ID NO. |
|---|---|---|---|
| 301-11 | Heavy CDR-H1 | GFTFSDYY | 1 |
| 301-11 | CDR-H2 | ISDGGSYT | 2 |
| 301-11 | CDR-H3 | ARDYYGSSSYTSGFAY | 3 |
| 301-11 | Light CDR-L1 | QSLLNSRTRKNY | 4 |
| 301-11 | CDR-L2 | WAS | 5 |
| 301-11 | CDR-L3 | KQSYNLYT | 6 |
| 301-03-1 | Heavy CDR-H1 | GFTFSDYY | 1 |
| 301-03-1 | CDR-H2 | ISDGGSYT | 2 |
| 301-03-1 | CDR-H3 | ARDYYGSNSYTSGFAY | 80 |
| 301-03-1 | Light CDR-L1 | QSLLNSRTRKNY | 4 |
| 301-03-1 | CDR-L2 | WAS | 5 |
| 301-03-1 | CDR-L3 | KQSYNLYT | 6 |
| 301-03-2 | Heavy CDR-H1 | GFTFSDYY | 1 |
| 301-03-2 | CDR-H2 | ISDGGSYT | 2 |
| 301-03-2 | CDR-H3 | ARDYYGSNSYTSGFAY | 80 |
| 301-03-2 | Light CDR-L1 | QSIVHSNGNTY | 81 |
| 301-03-2 | CDR-L2 | KVS | 82 |
| 301-03-2 | CDR-L3 | FQGSHVPLT | 83 |

TABLE 3

Consensus DNA sequence and translated protein sequences of the variable region. The complementarity determining regions (CDRs) are underlined according to IMTG/LIGM-DB.

| Antibody and Isotype | Consensus cDNA Sequence | Polypeptide sequence |
|---|---|---|
| 301-11 IgG3 SEQ ID NO: 8, 9 | ATGAACTTTGGGCTCAGCTTGATTTTCCTTGTCCTTGTTTTAAAA GGTGTCCAGTGTGAAGTGCAGCTGGTGGAGTCTGGGGGAGGCTTA GTGAAGCCTGGAGGGTCCCTGAAACTCTCCTGTGCAGCCTCTGGA TTCACTTTCAGTGACTATTACATGTATTGGGTTCGCCAGACTC CGGAAAAGAGGCTGGAGTGGGTCGCAACCATTAGTGATGGTGG TAGTTACACCTCCTATCCAGACAGTGTGAAGGGACGATTCACCA TCTCCAGAGACAATGCCAAGAACAACCTGTACCTGCAAATGAGCA GTCTGAGGTCTGAGGACACAGCCATGTATTACTGTGCAAGAGAT TACTACGGTAGTAGTAGCTACACCTCGGGCTTTGCTTACTG GGGCCAAGGGACTCTGGTCACTGTCTCTGCA | MNFGLSLIFLVLVLKG VQCEVQLVESGGGLVK PGGSLKLSCAASGFTF SDYYMYWVRQTPEKRL EWVATISDGGSYTSY PDSVKGRFTISRDNAK NNLYLQMSSLRSEDTA MYYCARDYYGSSSYT SGFAYWGQGTLVTVSA |
| 301-11 Kappa SEQ ID NO: 10, 11 | ATGGATTCACAGGCCCAGGTTCTTATATTGCTGCTGCTATGGGTA TCTGGTACCTGTGGGGACATTGTGATGTCACAGTCTCCATCCTCC CTGGCTGTGTCAACAGGAGAAGGTCACTATGAGCTGCAAATCC AGTCAGAGTCTGCTCAACAGTAGAACCCGAAAGAACTACTT GGCTTGGTACCAGCAGAAACCAGGGCAGTCTCCTAAACTGCTGAT CTACTGGGCATCCACTAGGGAATCTGGGGTCCCTGATCGCTTCA CAGGCAGTGGATCTGGGACAGATTTCACTCTCACCATCAGCAGTG TGCAGGCTGAAGACCTGGCAGTTTATTACTGCAAGCAATCTTAT AATCTGTACACGTTCGGAGGGGGGACCAAGCTGGAAATAAAA | MDSQAQVLILLLLWVS GTCGDIVMSQSPSSLA VSTGEKVTMSCKSSQS LLNSRTRKNYLAWYQ QKPGQSPKLLIYWAST RESGVPDRFTGSGSGT DFTLTISSVQAEDLAV YYCKQSYNLYTFGGG TKLEIK |

TABLE 3-continued

Consensus DNA sequence and translated protein sequences of the variable region. The complementarity determining regions (CDRs) are underlined according to IMTG/LIGM-DB.

| Antibody and Isotype | Consensus cDNA Sequence | Polypeptide sequence |
|---|---|---|
| 301-03 IgG3 SEQ ID NO: 84, 85 | ATGAACTTCGGGCTCAGCTTGATTTTCCTTGTCCTTGTTTTAAAA GGTGTCCAGTGTGAAGTGCAGCTGGTGGAGTCTGGGGGAGGCTTA GTGAAGCCTGGAGGGTCCCTGAAACTCTCCTGTGCAGCCTCTGGA TTCACTTTCAGTGACTATTACATGTATTGGGTTCGCCAGACTC CGGAAAAGAGGCTGGAGTGGGTCGCAACCATTAGTGATGGTGG TAGTTACACCTCCTATCCAGACAGTGTGAAGGGGCGATTCACCA TCTCCAGAGACAGTGCCAAGAACAACCTGTACCTGCAAATGAGCA GTCTGAAGTCTGAGGACACAGCCATGTATTACTGTGCAAGAGAT TACTACGGTAGTAATAGTTACACCTCGGGCTTTGCTTACTG GGGCCAAGGGACTCTGGTCACTGTCTCTGCA | MNFGLSLIFLVLVLKG VQCEVQLVESGGGLVK PGGSLKLSCAASGFTF SDYYMYWVRQTPEKRL EWVATISDGGSYTSY PDSVKGRFTISRDSAK NNLYLQMSSLKSEDTA MYYCARDYYGSNSYT SGFAYWGQGTLVTVSA |
| 301-03 Kappa 1 SEQ ID NO: 86, 87 | ATGGATTCACAGGCCCAGGTTCTTATATTGCTGCTGCTATGGGTA TCTGGTACCTGTGGGGACATTGTGATGTCACAGTCTCCATCCTCC CTGGCTGTGTCAGCAGGAGAGAAGGTCACTATGAGCTGCAAATCC AGTCAGAGTCTGCTCAATAGTAGAACCCGAAAGAACTACTT GGCTTGGTACCAGCAGAAACCAGGGCAGTCTCCTAAACTGCTGAT CTACTGGGCATCCACTAGGGAATCTGGGGTCCCTGATCGCTTCA CAGGCAGTGGATCTGGGACAGATTTCACTCTCACCATCAGCAGTG TGCAGGCTGAAGACCTGGCAGTTTATTACTGCAAGCAATCTTAT AATCTGTACACGTTCGGAGGGGGGACCAAGCTGGAAATAAAA | MDSQAQVLILLLLWVS GTCGDIVMSQSPSSLA VSAGEKVTMSCRSSQS LLNSRTRKNYLAWYQ QKPGQSPKLLIYWAST RESGVPDRFTGSGSGT DFTLTISSVQAEDLAV YYCKQSYNLYT**FGGG TKLEIK |
| 301-03 Kappa 2 SEQ ID NO: 88, 89 | ATGAAGTTGCCTGTTAGGCTGTTGGTGCTGATGTTCTGGATTCCT GCTTCCAGCAGTGATGTTTTGATGACCCAAACTCCACTCTCCCTG CCTGTCAGTCTTGGAGATCAAGCCTCCATCTCTTGCAGATCTAGT CAGAGCATTGTACATAGTAATGGAAACACCTATTTAGAATGG TACCTGCAGAAACCAGGCCAGTCTCCAAAGCTCCTGATCTACAAA GTTTCCAACCGATTTTCTGGGGTCCCAGACAGGTTCAGTGGCAG TGGATCAGGGACAGATTTCACACTCAAGATCAGCAGAGTGGAGGC TGAGGATCTGGGAGTTTATTTCTGCTTTCAAGGTTCACATGTT CCTCTCACGTTCGGTGCTGGGACCAAGCTGGAGCTGAAA | MKLPVRLLVLMFWIPA SSSDVLMTQTPLSLPV SLGDQASISCRSSQSI VHSNGNTYLEWYLQK PGQSPKLLIYKVSNRF SGVPDRFSGSGSGTDF TLKISRVEAEDLGVYF CFQGSHVPLTFGAGTK LELK |

TABLE 4A

| Humanized Antibody 301-11 | cDNA Sequence | Polypeptide sequence |
|---|---|---|
| VH0 SEQ ID NO: 13, 14 | CAGGTCCAACTGCAGCAGCCTGGGGCTGAGCTTGTGAAGCCTGGG GCTTCAGTGAAGATGTCCTGCAAGGCTTCTGGATTCACTTTCAGT GACTATTACATAAACTGGGTGAAGCAGAGGCCTGGACAAGGCCTT GAGTGGATTGGAGATATTAGTGATGGTGGTAGTTACACCTACAAT GCTAAGTTCAAGAGCAAGGCCACACTGACTCTGGACACATCCTCC AGCACAGCCTACATGCAGCTCAGCAGCCTGACATCTGAGGACTCT GCGGTCTATTACTGTGCAAGAGATTACTACGGTAGTAGTAGCTAC ACCTCGGGCTTTGCTTACTGGGGCGCAGGCACCACGGTCACCGTC TCCTCA | QVQLQQPGAELVKPGA SVKMSCKASGFTFSDY YINWVKQRPGQGLEWI GDISDGGSYTYNAKFK SKATLTLDTSSSTAYM QLSSLTSEDSAVYYCA RDYYGSSSYTSGFAYW GAGTTVTVSS |
| VH1 SEQ ID NO: 15, 16 | CAGGTCCAACTGGTGCAGTCTGGGGCTGAGCTTAAGAAGCCTGGG GCTTCAGTGAAGATGTCCTGCAAGGCTTCTGGATTCACTTTCAGT GACTATTACATAAACTGGGTGAAGCAGAGGCCTGGACAAGGCCTT GAGTGGATTGGAGATATTAGTGATGGTGGTAGTTACACCTACAAT GCTAAGTTCAAGAGCAGAGCCACACTGACTCTGGACACATCCATA AGCACAGCCTACATGCAGCTCAGCAGCCTGACATCTGAGGACTCT GCGGTCTATTACTGTGCAAGAGATTACTACGGTAGTAGTAGCTAC ACCTCGGGCTTTGCTTACTGGGGCCAAGGCACCACGGTCACCGTC TCCTCA | QVQLVQSGAELKKPGA SVKMSCKASGFTFSDY YINWVKQRPGQGLEWI GDISDGGSYTYNAKFK SRATLTLDTSISTAYM QLSSLTSEDSAVYYCA RDYYGSSSYTSGFAYW GQGTTVTVSS |
| VH2 SEQ ID NO: 17, 18 | CAGGTCCAACTGGTGCAGTCTGGGGCTGAGGTGAAGAAGCCTGGG GCTTCAGTGAAGATGTCCTGCAAGGCTTCTGGATTCACTTTCAGT GACTATTACATAAACTGGGTGAAGCAGAGGCCTGGACAAGGCCTT GAGTGGATTGGAGATATTAGTGATGGTGGTAGTTACACCTACAAT GCTAAGTTCAAGAGCAGAGCCACACTGACTCTGGACACATCCATA AGCACAGCCTACATGGAGCTCAGCAGCCTGAGATCTGAGGACACG GCGGTCTATTACTGTGCAAGAGATTACTACGGTAGTAGTAGCTAC ACCTCGGGCTTTGCTTACTGGGGCCAAGGCACCACGGTCACCGTC TCCTCA | QVQLVQSGAEVKKPGA SVKMSCKASGFTFSDY YINWVKQRPGQGLEWI GDISDGGSYTYNAKFK SRATLTLDTSISTAYM ELSSLRSEDTAVYYCA RDYYGSSSYTSGFAYW GQGTTVTVSS |
| VH3 SEQ ID NO: 19, 20 | CAGGTCCAACTGGTGCAGTCTGGGGCTGAGGTGAAGAAGCCTGGG GCTTCAGTGAAGGTGTCCTGCAAGGCTTCTGGATTCACTTTCAGT GACTATTACATAAACTGGGTGCAGCAGAGGCCTGGACAAGGCCTT | QVQLVQSGAEVKKPGA SVKVSCKASGFTFSDY YINWVRQRPGQGLEWI |

TABLE 4A-continued

| Humanized Antibody 301-11 | cDNA Sequence | Polypeptide sequence |
|---|---|---|
| | GAGTGGATTGGAGATAATTAGTGATGGTGGTAGTTACACCTACAAT GCTAAGTTCAAGAGCAGAGCCACACTGACTCTGGACACATCCATA AGCACAGCCTACATGGAGCTCAGCAGCCTGAGATCTGAGGACACG GCGGTCTATTACTGTGCAAGAGATTACTACGGTAGTAGTAGCTAC ACCTCGGGCTTTGCTTACTGGGGCCAAGGCACCACGGTCACCGTC TCCTCA | GDISDGGSYTYNAKFK SRATLTLDTSISTAYM ELSSLRSEDTAVYYCA RDYYGSSSYTSGFAYW GQGTTVTSS |
| VH4 SEQ ID NO: 21, 22 | CAGGTCCAACTGGTGCAGTCTGGGGCTGAGGTGAAGAAGCCTGGG GCTTCAGTGAAGGTGTCCTGCAAGGCTTCTGGATTCACTTTCAGT GACTATTACATAAACTGGGTGCGACAGAGGCCTGGACAAGGCTT GAGTGGATTGGAGATATTAGTGATGGTGGTAGTTACACCTACAAT GCTAAGTTCAAGAGCAGAGTCACACTGACTCTGGACACATCCATA AGCACAGCCTACATGGAGCTCAGCAGCCTGAGATCTGAGGACACG GCGGTCTATTACTGTGCAAGAGATTACTACGGTAGTAGTAGCTAC ACCTCGGGCTTTGCTTACTGGGGCCAAGGCACCACGGTCACCGTC TCCTCA | QVQLVQSGAEVKKPGA SVKVSCKASGFTFSDY YINWVRQRPGQGLEWI GDISDGGSYTYNAKFK SRVTLTLDTSISTAYM ELSSLRSEDTAVYYCA RDYYGSSSYTSGFAYW GQGTTVTSS |
| VH5 SEQ ID NO: 23, 24 | CAGGTCCAACTGGTGCAGTCTGGGGCTGAGGTGAAGAAGCCTGGG GCTTCAGTGAAGGTGTCCTGCAAGGCTTCTGGATTCACTTTCAGT GACTATTACATAAACTGGGTGCGACAGAGGCCTGGACAAGGCTT GAGTGGATGGGAGATATTAGTGATGGTGGTAGTTACACCTACAAT GCTAAGTTCAAGAGCAGAGTCACACTGACTAGGGACACATCCATA AGCACAGCCTACATGGAGCTCAGCAGCCTGAGATCTGAGGACACG GCGGTCTATTACTGTGCAAGAGATTACTACGGTAGTAGTAGCTAC ACCTCGGGCTTTGCTTACTGGGGCCAAGGCACCACGGTCACCGTC TCCTCA | QVQLVQSGAEVKKPGA SVKVSCKASGFTFSDY YINWVRQRPGQGLEWM GDISDGGSYTYNAKFK SRVTLTRDTSISTAYM ELSSLRSEDTAVYYCA RDYYGSSSYTSGFAYW GQGTTVTSS |
| VH6 SEQ ID NO: 25, 26 | CAGGTCCAACTGGTGCAGTCTGGGGCTGAGGTGAAGAAGCCTGGG GCTTCAGTGAAGGTGTCCTGCAAGGCTTCTGGATTCACTTTCAGT GACTATTACATAAACTGGGTGCGACAGAGGCCTGGACAAGGCTT GAGTGGATGGAGATATTAGTGATGGTGGTAGTTACACCTACAAT GCTAAGTTCCAGGGCAGAGTCACAATGACTAGGGACACATCCATA AGCACAGCCTACATGGAGCTCAGCAGCCTGAGATCTGAGGACACG GCGGTCTATTACTGTGCAAGAGATTACTACGGTAGTAGTAGCTAC ACCTCGGGCTTTGCTTACTGGGGCCAAGGCACCACGGTCACCGTC TCCTCA | QVQLVQSGAEVKKPGA SVKVSCKASGFTFSDY YINWVRQRPGQGLEWM GDISDGGSYTYNAKFQ GRVTMTRDTSISTAYM ELSSLRSEDTAVYYCA RDYYGSSSYTSGFAYW GQGTTVTSS |
| VK0 SEQ ID NO: 27, 28 | GATGTTTTGATGACCCAAACTCCACTCTCCCTGCCTGTCAGTCTT GGAGATCAAGCCTCCATCTCTTGCAGATCTAGTCAGAGTCTGCTC AACAGTAGAACCCGAAAGAACTACTTAGAATGGTACCTGCAGAAA CCAGGCCAGTCTCCAAAGCTCCTGATCTACTGGGCATCCAACCGA TTTTCTGGGGTCCCAGACAGGTTCAGTGGCAGTGGATCAGGGACA GATTTCACACTCAAGATCAGCAGAGTGGAGGCTGAGGATCTGGGA GTTTATTACTGCAAGCAATCTTATAATCTGTACACGTTTGGCAGC GGGACCAAGCTGGAGATCAAA | DVLMTQTPLSLPVSLG DQASISCRSSQSLLNS RTRKNYLEWYLQKPGQ SPKLLIYWASNRFSGV PDRFSGSGSGTDFTLK ISRVEAEDLGVYYCKQ SYNLYTFGSGTKLEIK |
| VK1 SEQ ID NO: 29, 30 | GATGTTTTGATGACCCAATCTCCACTCTCCCTGCCTGTCACCCTT GGACAGCCGGCCTCCATCTCTTGCAGATCTAGTCAGAGTCTGCTC AACAGTAGAACCCGAAAGAACTACTTAGAATGGTTTCAGCAGAAA CCAGGCCAGTCTCCAAGGCTCCTGATCTACTGGGCATCCAACCGA TTTTCTGGGGTCCCAGACAGGTTCAGTGGCAGTGGATCAGGGACA GATTTCACACTCAAGATCAGCAGAGTGGAGGCTGAGGATGTTGGA GTTTATTACTGCAAGCAATCTTATAATCTGTACACGTTTGGCCAA GGGACCAAGCTGGAGATCAAA | DVLMTQSPLSLPVTLG QPASISCRSSQSLLNS RTRKNYLEWFQQKPGQ SPRRLIYWASNRFSGV PDRFSGSGSTDFTLK ISRVEADVGVYYCKQ SYNLYTFGQGTKLEIK |
| VK2 SEQ ID NO: 31, 32 | GATGTTGTGATGACCCAATCTCCACTCTCCCTGCCTGTCACCCTT GGACAGCCGGCCTCCATCTCTTGCAGATCTAGTCAGAGTCTGCTC AACAGTAGAACCCGAAAGAACTACTTAGAATGGTTTCAGCAGAAA CCAGGCCAGTCTCCAAGGCGCCTGATCTACTGGGCATCCAACCGA TTTTCTGGGGTCCCAGACAGGTTCAGTGGCAGTGGATCAGGGACA GATTTCACACTCAAGATCAGCAGAGTGGAGGCTGAGGATGTTGGA GTTTATTACTGCAAGCAATCTTATAATCTGTACACGTTTGGCCAA GGGACCAAGCTGGAGATCAAA | DVVMTQSPLSLPVTLG QPASISCRSSQSLLNS RTRKNYLEWFQQKPGQ SPRRLIYWASNRFSGV PDRFSGSGSGTDFTLK ISRVEADVGVYYCKQ SYNLYTFGQGTKLEIK |
| VK3 SEQ ID NO: 33, 34 | GATGTTGTGATGACCCAATCTCCACTCTCCCTGCCTGTCACCCTT GGACAGCCGGCCTCCATCTCTTGCAGATCTAGTCAGAGTCTGCTC AACAGTAGAACCCGAAAGAACTACTTAGAATGGTTTCAGCAGCCGGG CCAGGCCAGTCTCCAAGGCGCCTGATCTACTGGGCATCCAACCGA TTTTCTGGGGTCCCAGACAGGTTCAGTGGCAGTGGATCAGGGACA GATTTCACACTCAAGATCAGCAGAGTGGAGGCTGAGGATGTTGGA GTTTATTACTGCAAGCAATCTTATAATCTGTACACGTTTGGCCAA GGGACCAAGCTGGAGATCAAA | DVVMTQSPLSLPVTLG QPASISCRSSQSLLNS RTRKNYLEWFQQRPGQ SPRRLIYWASNRFSGV PDRFSGSGSGTDFTLK ISRVEADVGVYYCKQ SYNLYTFGQGTKLEIK |
| VK4 SEQ ID NO: 35, 36 | GATGTTCTGATGACCCAATCTCCACTCTCCCTGCCTGTCACCCTT GGACAGCCGGCCTCCATCTCTTGCAGATCTAGTCAGAGTCTGCTC AACAGTAGAACCCGAAAGAACTACTTAGAATGGTACCTGCAGAGG | DVLMTQSPLSLPVTLG QPASISCRSSQSLLNS RTRKNYLEWYLQRPGQ |

TABLE 4A-continued

| Humanized Antibody 301-11 | cDNA Sequence | Polypeptide sequence |
|---|---|---|
| | CCAGGCCAGTCTCCAAAGCTGCTGATCTACTGGGCATCCAACCGA<br>TTTTCTGGGGTCCCAGACAGGTTCAGTGGCAGTGGATCAGGGACA<br>GATTTCACACTCAAGATCAGCAGAGTGGAGGCTGAGGATGTTGGA<br>GTTTATTACTGCAAGCAATCTTATAATCTGTACACGTTTGGCCAA<br>GGGACCAAGCTGGAGATCAAA | SPKLLIYWASNRFSGV<br>PDRFSGSGSGTDFTLK<br>ISRVEAEDVGVYYCKQ<br>SYNLYTFGQGTKLEIK |
| VK5<br>SEQ ID NO:<br>37, 38 | GATGTTCTGATGACCCAATCTCCACTCTCCCTGCCTGTCACCCTT<br>GGACAGCCGGCCTCCATCTCTTGCAGATCTAGTCAGAGTCTGCTC<br>AACAGTAGAACCCGAAAGAACTACTTAGAATGGTACCAGCAGAGG<br>CCAGGCCAGTCTCCAAGGCTGCTGATCTACTGGGCATCCAACCGA<br>TTTTCTGGGGTCCCAGACAGGTTCAGTGGCAGTGGATCAGGGACA<br>GATTTCACACTCAAGATCAGCAGAGTGGAGGCTGAGGATGTTGGA<br>GTTTATTACTGCAAGCAATCTTATAATCTGTACACGTTTGGCCAA<br>GGGACCAAGCTGGAGATCAAA | DVLMTQSPLSLPVTLG<br>QPASISCRSSQSLLNS<br>RTRKNYLEWYQQRPGQ<br>SPRLLIYWASNRFSGV<br>PDRFSGSGSGTDFTLK<br>ISRVEAEDVGVYYCKQ<br>SYNLYTFGQGTKLEIK |
| VK6<br>SEQ ID NO:<br>39, 40 | GATGTTGTGATGACCCAATCTCCACTCTCCCTGCCTGTCACCCTT<br>GGACAGCCGGCCTCCATCTCTTGCAGATCTAGTCAGAGTCTGCTC<br>AACAGTAGAACCCGAAAGAACTACTTAGAATGGTACCAGCAGAGG<br>CCAGGCCAGTCTCCAAGGCTGCTGATCTACTGGGCATCCAACCGA<br>TTTTCTGGGGTCCCAGACAGGTTCAGTGGCAGTGGATCAGGGACA<br>GATTTCACACTCAAGATCAGCAGAGTGGAGGCTGAGGATGTTGGA<br>GTTTATTACTGCAAGCAATCTTATAATCTGTACACGTTTGGCCAA<br>GGGACCAAGCTGGAGATCAAA | DVVMTQSPLSLPVTLG<br>QPASISCRSSQSLLNS<br>RTRKNYLEWYQQRPGQ<br>SPRLLIYWASNRFSGV<br>PDRFSGSGSGTDFTLK<br>ISRVEAEDVGVYYCKQ<br>SYNLYTFGQGTKLEIK |

TABLE 4B

| Humanized Antibody Sequence | cDNA Sequence | Polypeptide Sequence |
|---|---|---|
| 301-17<br>VH0<br>SEQ ID NO:<br>41, 42<br>(mouse) | CAGGTCCAACTGCAGCAGCCTGGGGCTGAGCTTGTGAAGCCTGGG<br>GCTTCAGTGAAGATGTCCTGCAAGGCTTCTGGCTACAGCTTCACC<br>AGCTACTGGATAAACTGGGTGAAGCAGAGGCCTGGACAAGGCCTT<br>GAGTGGATTGGAGATGTGCATCCTGGTAGAGGCGTGTCCACATAC<br>AATGCTAAGTTCAAGAGCAAGGCCACACTGACTCTGGACACATCC<br>TCCAGCACAGCCTACATGCAGCTCAGCAGCCTGACATCTGAGGAC<br>TCTGCGGTCTATTACTGTAGCAGATCCCATGGTAACACCTACTGG<br>TTTTTTGACGTCTGGGGCGCAGGCACCACGGTCACCGTCTCCTCA | QVQLQQPGAELVKPGA<br>SVKMSCKASGYSFTSY<br>WINWVKQRPGQGLEWI<br>GDVHPGRGVSTYNAKF<br>KSKATLTLDTSSSTAY<br>MQLSSLTSEDSAVYYC<br>SRSHGNTYWFFDVWGA<br>GTTVTVSS |
| VH1<br>SEQ ID NO:<br>43, 44 | CAGGTCCAACTGGTGCAGTCTGGGGCTGAGCTTAAGAAGCCTGGG<br>GCTTCAGTGAAGATGTCCTGCAAGGCTTCTGGCTACAGCTTCACC<br>AGCTACTGGATAAACTGGGTGAAGCAGAGGCCTGGACAAGGCCTT<br>GAGTGGATTGGAGATGTGCATCCTGGTAGAGGCGTGTCCACATAC<br>AATGCTAAGTTCAAGAGCAGAGCCACACTGACTCTGGACACATCC<br>ATAAGCACAGCCTACATGCAGCTCAGCAGCCTGACATCTGAGGAC<br>TCTGCGGTCTATTACTGTAGCAGATCCCATGGTAACACCTACTGG<br>TTTTTTGACGTCTGGGGCCAAGGCACCACGGTCACCGTCTCCTCA | QVQLVQSGAELKKPGA<br>SVKMSCKASGYSFTSY<br>WINWVKQRPGQGLEWI<br>GDVHPGRGVSTYNAKF<br>KSRATLTLDTSISTAY<br>MQLSSLTSEDSAVYYC<br>SRSHGNTYWFFDVWGQ<br>GTTVTVSS |
| VH2<br>SEQ ID NO:<br>45, 46 | CAGGTCCAACTGGTGCAGTCTGGGGCTGAGGTGAAGAAGCCTGGG<br>GCTTCAGTGAAGATGTCCTGCAAGGCTTCTGGCTACAGCTTCACC<br>AGCTACTGGATAAACTGGGTGAAGCAGAGGCCTGGACAAGGCCTT<br>GAGTGGATTGGAGATGTGCATCCTGGTAGAGGCGTGTCCACATAC<br>AATGCTAAGTTCAAGAGCAGAGCCACACTGACTCTGGACACATCC<br>ATAAGCACAGCCTACATGGAGCTCAGCAGCCTGAGATCTGAGGAC<br>ACGGCGGTCTATTACTGTAGCAGATCCCATGGTAACACCTACTGG<br>TTTTTTGACGTCTGGGGCCAAGGCACCACGGTCACCGTCTCCTCA | QVQLVQSGAEVKKPGA<br>SVKMSCKASGYSFTSY<br>WINWVKQRPGQGLEWI<br>GDVHPGRGVSTYNAKF<br>KSRATLTLDTSISTAY<br>MELSSLRSEDTAVYYC<br>SRSHGNTYWFFDVWGQ<br>GTTVTVSS |
| VH3<br>SEQ ID NO:<br>47, 48 | CAGGTCCAACTGGTGCAGTCTGGGGCTGAGGTGAAGAAGCCTGGG<br>GCTTCAGTGAAGGTGTCCTGCAAGGCTTCTGGCTACAGCTTCACC<br>AGCTACTGGATAAACTGGGTGCGACAGAGGCCTGGACAAGGCCTT<br>GAGTGGATTGGAGATGTGCATCCTGGTAGAGGCGTGTCCACATAC<br>AATGCTAAGTTCAAGAGCAGAGCCACACTGACTCTGGACACATCC<br>ATAAGCACAGCCTACATGGAGCTCAGCAGCCTGAGATCTGAGGAC<br>ACGGCGGTCTATTACTGTAGCAGATCCCATGGTAACACCTACTGG<br>TTTTTTGACGTCTGGGGCCAAGGCACCACGGTCACCGTCTCCTCA | QVQLVQSGAEVKKPGA<br>SVKVSCKASGYSFTSY<br>WINWVRQRPGQGLEWI<br>GDVHPGRGVSTYNAKF<br>KSRATLTLDTSISTAY<br>MELSSLRSEDTAVYYC<br>SRSHGNTYWFFDVWGQ<br>GTTVTVSS |
| VH4<br>SEQ ID NO:<br>49, 50 | CAGGTCCAACTGGTGCAGTCTGGGGCTGAGGTGAAGAAGCCTGGG<br>GCTTCAGTGAAGGTGTCCTGCAAGGCTTCTGGCTACAGCTTCACC<br>AGCTACTGGATAAACTGGGTGCGACAGAGGCCTGGACAAGGCCTT<br>GAGTGGATTGGAGATGTGCATCCTGGTAGAGGCGTGTCCACATAC<br>AATGCTAAGTTCAAGAGCAGAGTCACACTGACTCTGGACACATCC<br>ATAAGCACAGCCTACATGGAGCTCAGCAGCCTGAGATCTGAGGAC | QVQLVQSGAEVKKPGA<br>SVKVSCKASGYSFTSY<br>WINWVRQRPGQGLEWI<br>GDVHPGRGVSTYNAKF<br>KSRVTLTLDTSISTAY<br>MELSSLRSEDTAVYYC |

TABLE 4B-continued

| Humanized Sequence Antibody | cDNA Sequence | Polypeptide Sequence |
|---|---|---|
| | ACGGCGGTCTATTACTGTAGCAGATCCCATGGTAACACCTACTGG TTTTTTGACGTCTGGGGCCAAGGCACCACGGTCACCGTCTCCTCA | SRSHGNTYWFFDVWGQ GTTVTVSS |
| VH5 SEQ ID NO: 51, 52 | CAGGTCCAACTGGTGCAGTCTGGGGCTGAGGTGAAGAAGCCTGGG GCTTCAGTGAAGGTGTCCTGCAAGGCTTCTGGCTACAGCTTCACC AGCTACTGGATAAACTGGGTGCGACAGAGGCCTGGACAAGGCCTT GAGTGGATGGGAGATGTGCATCCTGGTAGAGGCGTGTCCACATAC AATGCTAAGTTCAAGAGCAGAGTCACACTGACTAGGGACACATCC ATAAGCACAGCCTACATGGAGCTCAGCAGCCTGAGATCTGAGGAC ACGGCGGTCTATTACTGTAGCAGATCCCATGGTAACACCTACTGG TTTTTTGACGTCTGGGGCCAAGGCACCACGGTCACCGTCTCCTCA | QVQLVQSGAEVKKPGA SVKVSCKASGYSFTSY WINWVRQRPGQGLEWM GDVHPGRGVSTYNAKF KSRVTLTRDTSISTAY MELSSLRSEDTAVYYC SRSHGNTYWFFDVWGQ GTTVTVSS |
| VH6 SEQ ID NO: 53, 54 | CAGGTCCAACTGGTGCAGTCTGGGGCTGAGGTGAAGAAGCCTGGG GCTTCAGTGAAGGTGTCCTGCAAGGCTTCTGGCTACAGCTTCACC AGCTACTGGATAAACTGGGTGCGACAGAGGCCTGGACAAGGCCTT GAGTGGATGGGAGATGTGCATCCTGGTAGAGGCGTGTCCACATAC AATGCTAAGTTCCAGGGCAGAGTCACAATGACTAGGGACACATCC ATAAGCACAGCCTACATGGAGCTCAGCAGCCTGAGATCTGAGGAC ACGGCGGTCTATTACTGTAGCAGATCCCATGGTAACACCTACTGG TTTTTTGACGTCTGGGGCCAAGGCACCACGGTCACCGTCTCCTCA | QVQLVQSGAEVKKPGA SVKVSCKASGYSFTSY WINWVRQRPGQGLEWM GDVHPGRGVSTYNAKF QGRVTMTRDTSISTAY MELSSLRSEDTAVYYC SRSHGNTYWFFDVWGQ GTTVTVSS |
| VK0 SEQ ID NO: 55, 56 (mouse) | GATGTTTTGATGACCCAAACTCCACTCTCCCTGCCTGTCAGTCTT GGAGATCAAGCCTCCATCTCTTGCAGATCTAGTCAGAGCATTGTA CATAGTAATGGAAACACCTATTTAGAATGGTACCTGCAGAAACCA GGCCAGTCTCCAAAGCTCCTGATCTACAAAGTTTCCAACCGATTT TCTGGGGTCCCAGACAGGTTCAGTGGCAGTGGATCAGGGACAGAT TTCACACTCAAGATCAGCAGAGTGGAGGCTGAGGATCTGGGAGTT TATTACTGCTTTCAAGGTTCACATGTTCCTTTCACTTTTGGCAGC GGGACCAAGCTGGAGATCAAA | DVLMTQTPLSLPVSLG DQASISCRSSQSIVHS NGNTYLEWYLQKPGQS PKLLIYKVSNRFSGVP DRFSGSGSGTDFTLKI SRVEAEDLGVYYCFQG SHVPFTFGSGTKLEIK |
| VK1 SEQ ID NO: 57, 58 | GATGTTTTGATGACCCAATCTCCACTCTCCCTGCCTGTCACCCTT GGACAGCCGGCCTCCATCTCTTGCAGATCTAGTCAGAGCATTGTA CATAGTAATGGAAACACCTATTTAGAATGGTTTCAGCAGAAACCA GGCCAGTCTCCAAGGCGCCTGATCTACAAAGTTTCCAACCGATTT TCTGGGGTCCCAGACAGGTTCAGTGGCAGTGGATCAGGGACAGAT TTCACACTCAAGATCAGCAGAGTGGAGGCTGAGGATGTTGGAGTT TATTACTGCTTTCAAGGTTCACATGTTCCTTTCACTTTTGGCCAA GGGACCAAGCTGGAGATCAAA | DVLMTQSPLSLPVTLG QPASISCRSSQSIVHS NGNTYLEWFQQKPGQS PRRLIYKVSNRFSGVP DRFSGSGSGTDFTLKI SRVEAEDVGVYYCFQG SHVPFTFGQGTKLEIK |
| VK2 SEQ ID NO: 59, 60 | GATGTTGTGATGACCCAATCTCCACTCTCCCTGCCTGTCACCCTT GGACAGCCGGCCTCCATCTCTTGCAGATCTAGTCAGAGCATTGTA CATAGTAATGGAAACACCTATTTAGAATGGTTTCAGCAGAAACCA GGCCAGTCTCCAAGGCGCCTGATCTACAAAGTTTCCAACCGATTT TCTGGGGTCCCAGACAGGTTCAGTGGCAGTGGATCAGGGACAGAT TTCACACTCAAGATCAGCAGAGTGGAGGCTGAGGATGTTGGAGTT TATTACTGCTTTCAAGGTTCACATGTTCCTTTCACTTTTGGCCAA GGGACCAAGCTGGAGATCAAA | DVVMTQSPLSLPVTLG QPASISCRSSQSIVHS NGNTYLEWFQQKPGQS PRRLIYKVSNRFSGVP DRFSGSGSGTDFTLKI SRVEAEDVGVYYCFQG SHVPFTFGQGTKLEIK |
| VK3 SEQ ID NO: 61, 62 | GATGTTGTGATGACCCAATCTCCACTCTCCCTGCCTGTCACCCTT GGACAGCCGGCCTCCATCTCTTGCAGATCTAGTCAGAGCATTGTA CATAGTAATGGAAACACCTATTTAGAATGGTTTCAGCAGAGGCCA GGCCAGTCTCCAAGGCGCCTGATCTACAAAGTTTCCAACCGATTT TCTGGGGTCCCAGACAGGTTCAGTGGCAGTGGATCAGGGACAGAT TTCACACTCAAGATCAGCAGAGTGGAGGCTGAGGATGTTGGAGTT TATTACTGCTTTCAAGGTTCACATGTTCCTTTCACTTTTGGCCAA GGGACCAAGCTGGAGATCAAA | DVVMTQSPLSLPVTLG QPASISCRSSQSIVHS NGNTYLEWFQQRPGQS PRRLIYKVSNRFSGVP DRFSGSGSGTDFTLKI SRVEAEDVGVYYCFQG SHVPFTFGQGTKLEIK |
| VK4 SEQ ID NO: 63, 64 | GATGTTCTGATGACCCAATCTCCACTCTCCCTGCCTGTCACCCTT GGACAGCCGGCCTCCATCTCTTGCAGATCTAGTCAGAGCATTGTA CATAGTAATGGAAACACCTATTTAGAATGGTACCTGCAGAGGCCA GGCCAGTCTCCAAAGCTGCTGATCTACAAAGTTTCCAACCGATTT TCTGGGGTCCCAGACAGGTTCAGTGGCAGTGGATCAGGGACAGAT TTCACACTCAAGATCAGCAGAGTGGAGGCTGAGGATGTTGGAGTT TATTACTGCTTTCAAGGTTCACATGTTCCTTTCACTTTTGGCCAA GGGACCAAGCTGGAGATCAAA | DVLMTQSPLSLPVTLG QPASISCRSSQSIVHS NGNTYLEWYLQRPGQS PKLLIYKVSNRFSGVP DRFSGSGSGTDFTLKI SRVEAEDVGVYYCFQG SHVPFTFGQGTKLEIK |
| VK5 SEQ ID NO: 65, 66 | GATGTTCTGATGACCCAATCTCCACTCTCCCTGCCTGTCACCCTT GGACAGCCGGCCTCCATCTCTTGCAGATCTAGTCAGAGCATTGTA CATAGTAATGGAAACACCTATTTAGAATGGTACCAGCAGAGGCCA GGCCAGTCTCCAAGGCTGCTGATCTACAAAGTTTCCAACCGATTT TCTGGGGTCCCAGACAGGTTCAGTGGCAGTGGATCAGGGACAGAT TTCACACTCAAGATCAGCAGAGTGGAGGCTGAGGATGTTGGAGTT TATTACTGCTTTCAAGGTTCACATGTTCCTTTCACTTTTGGCCAA GGGACCAAGCTGGAGATCAAA | DVLMTQSPLSLPVTLG QPASISCRSSQSIVHS NGNTYLEWYQQRPGQS PRLLIYKVSNRFSGVP DRFSGSGSGTDFTLKI SRVEAEDVGVYYCFQG SHVPFTFGQGTKLEIK |

TABLE 4B-continued

| Humanized Sequence Antibody | cDNA Sequence | Polypeptide Sequence |
|---|---|---|
| VK6 SEQ ID NO: 67, 68 | GATGTTGTGATGACCCAATCTCCACTCTCCCTGCCTGTCACCCTT GGACAGCCGGCCTCCATCTCTTGCAGATCTAGTCAGAGCATTGTA CATAGTAATGGAAACACCTATTTAGAATGGTACCAGCAGAGGCCA GGCCAGTCTCCAAGGCTGCTGATCTACAAAGTTTCCAACCGATTT TCTGGGGTCCCAGACAGGTTCAGTGGCAGTGGATCAGGGACAGAT TTCACACTCAAGATCAGCAGAGTGGAGGCTGAGGATGTTGGAGTT TATTACTGCTTTCAAGGTTCACATGTTCCTTTCACTTTTGGCCAA GGGACCAAGCTGGAGATCAAA | DVVMTQSPLSLPVTLG QPASISCRSSQSIVHS NGNTYLEWYQQRPGQS PRLLIYKVSNRFSGVP DRFSGSGSGTDFTLKI SRVEAEDVGVYYCFQG SHVPFTFGQGTKLEIK |

*VH0 and VK0 are mouse sequence provided for comparison

TABLE 5

| Constant regions | cDNA Sequence | Polypeptide sequence |
|---|---|---|
| IgG4 heavy chain SEQ ID NO: 69, 70 | GCTTCCACCAAGGGCCCATCCGTCTTCCCCCTGGCGCCCTGCTCC AGGAGCACCTCCGAGAGCACAGCCGCCCTGGGCTGCCTGGTCAAG GACTACTTCCCCGAACCGGTGACGGTGTCGTGGAACTCAGGCGCC CTGACCAGCGGCGTGCACACCTTCCCGGCTGTCCTACAGTCCTCA GGACTCTACTCCCTCAGCAGCGTGGTGACCGTGCCCTCCAGCAGC TTGGGCACGAAGACCTACACCTGCAATGTAGATCACAAGCCCAGC AACACCAAGGTGGACAAGAGAGTTGAGTCCAAATATGGTCCCCCA TGCCCACCATGCCCAGCCTGAGTTCCTGGGGGGACCATCAGTC TTCCTGTTCCCCCCAAAACCCAAGGACACTCTCATGATCTCCCGG ACCCCTGAGGTCACGTGCGTGGTGGTGGACGTGAGCCAGGAAGAC CCCGAGGTCCAGTTCAACTGGTACGTGGATGGCGTGGAGGTGCAT AATGCCAAGACAAAGCCGCGGGAGGAGCAGTTCAACAGCACGTAC CGTGTGGTCAGCGTCCTCACCGTCCTGCACCAGGACTGGCTGAAC GGCAAGGAGTACAAGTGCAAGGTCTCCAACAAAGGCCTCCCGTCC TCCATCGAGAAAACCATCTCCAAAGCCAAAGGGCAGCCCCGAGAG CCACAGGTGTACACCCTGCCCCCATCCCAGGAGGAGATGACCAAG AACCAGGTCAGCCTGACCTGCCTGGTCAAAGGCTTCTACCCCAGC GACATCGCCGTGGAGTGGGAGAGCAATGGGCAGCCGGAGAACAAC TACAAGACCACGCCTCCCGTGCTGGACTCCGACGGCTCCTTCTTC CTCTACAGCAGGCTAACCGTGGACAAGAGCAGGTGGCAGGAGGGG AATGTCTTCTCATGCTCCGTGATGCATGAGGCTCTGCACAACCAC TACACACAGAAGAGCCTCTCCCTGTCTCTGGGTAAATGA | ASTKGPSVFPLAPCSR STSESTAALGCLVKDY FPEPVTVSWNSGALTS GVHTFPAVLQSSGLYS LSSVVTVPSSSLGTKT YTCNVDHKPSNTKVDK RVESKYGPPCPPCPAP EFLGGPSVFLFPPKPK DTLMISRTPEVTCVVV DVSQEDPEVQFNWYVD GVEVHNAKTKPREEQF NSTYRVVSVLTVLHQD WLNGKEYKCKVSNKGL PSSIEKTISKAKGQPR EPQVYTLPPSQEEMTK NQVSLTCLVKGFYPSD IAVEWESNGQPENNYK TTPPVLDSDGSFFLYS RLTVDKSRWQEGNVFS CSVMHEALHNHYTQKS LSLSLGK |
| Kappa SEQ ID NO: 71, 72 | CGAACTGTGGCTGCACCATCTGTCTTCATCTTCCCGCCATCTGAT GAGCAGTTGAAATCTGGAACTGCCTCTGTTGTGTGCCTGCTGAAT AACTTCTATCCCAGAGAGGCCAAAGTACAGTGGAAGGTGGATAAC GCCCTCCAATCGGGTAACTCCCAGGAGAGTGTCACAGAGCAGGAC AGCAAGGACAGCACCTACAGCCTCAGCAGCACCCTGACGCTGAGC AAAGCAGACTACGAGAAACACAAAGTCTACGCCTGCGAAGTCACC CATCAGGGCCTGAGCTCGCCCGTCACAAAGAGCTTCAACAGGGGA GAGTGTTAG | RTVAAPSVFIFPPSDE QLKSGTASVVCLLNNF YPREAKVQWKVDNALQ SGNSQESVTEQDSKDS TYSLSSTLTLSKADYE KHKVYACEVTHQGLSS PVTKSFNRGEC |

Example 2

Immunohistochemistry

Immunohistochemistry was performed on frozen human brain sections, with no fixation or antigen retrieval. In a humidified chamber, non-specific staining was blocked by incubation with serum-free protein blocking reagent (Dako Canada Inc., Mississauga, ON, Canada) for 1 h. The following primary antibodies were used for immunostaining: mouse monoclonal isotype controls IgG1, IgG2a, and IgG2b, and anti-amyloidβ 6E10, all purchased from Biolegend, and purified antibodies 301-11 and 301-17. All antibodies were used at 1 µg/mL. Sections were incubated at room temperature for 1 h, and washed 3×5 min in TBS-T. Anti-Mouse IgG conjugated to Horseradish Peroxidase (1:1000) was applied to sections and incubated 45 min, then washed 3×5 min in TBS-T. DAB chromogen reagent (Vector Laboratories, Burlington ON, Canada) was applied and sections rinsed with distilled water when the desired level of target to background staining was achieved. Sections were counterstained with Mayer's haematoxylin, dehydrated and cover slips were applied. Slides were examined under a light microscope (Zeiss Axiovert 200M, Carl Zeiss Canada, Toronto ON, Canada) and representative images captured at 20 and 40× magnification using a Leica DC300 digital camera and software (Leica Microsystems Canada Inc., Richmond Hill, ON). Images were optimized in Adobe Photoshop using Levels Auto Correction.

Brain Extracts

Human brain tissues were obtained from the University of Maryland Brain and Tissue Bank upon approval from the UBC Clinical Research Ethics Board (C04-0595). Clinical diagnosis of probable AD was based on NINCDS-ADRDA criteria [5].

Homogenization: Human brain tissue samples were weighed and subsequently submersed in a volume of fresh, ice cold TBS and EDTA-free protease inhibitor cocktail from Roche Diagnostics (Laval QC, Canada) such that the final concentration of brain tissue was 20% (w/v). Tissue was homogenized in this buffer using a mechanical probe homogenizer (3×30 sec pulses with 30 sec pauses in between, all performed on ice). TBS homogenized samples were then subjected to ultracentrifugation (70,000×g for 90 min). Supernatants were collected, aliquoted and stored at −80° C. The protein concentration of TBS homogenates was determined using a BCA protein assay (Pierce Biotechnology Inc, Rockford Ill., USA).

Positive binding in brain extracts was confirmed using antibody 6E10.

SPR Analysis: 4 brain extracts from AD patients and 4 brain extracts from age-matched controls were pooled and analyzed. Brain samples, homogenized in TBS, included frontal cortex Brodmann area 9. All experiments were performed using a Molecular Affinity Screening System (MASS-1) (Sierra Sensors GmbH, Hamburg, Germany), an analytical biosensor that employs high intensity laser light and high speed optical scanning to monitor binding interactions in real time as described in Example 6. Purified antibodies generated for cyclopeptides described herein were captured on separate flow cells of a protein A-derivatized sensor chip and diluted samples injected over the surfaces for 180 seconds, followed by 120 seconds of dissociation in buffer and surface regeneration. Binding responses were double-referenced by subtraction of mouse control IgG reference surface binding and assay buffer, and the different groups of samples compared.

Results

Brain Extracts, CSF and Immunohistochemistry

The antibodies were tested for their ability to bind A-beta in soluble brain extracts, CSF and tissue samples of cavaderic healthy control and AD brains, results are shown in Table 6. Strength of positivity in Table 6 is shown by the number plus signs.

Each of antibodies 301-11 and 301-17 showed positive binding with brain homogenates and CSF from AD patients compared to control patients.

As shown in Table 6, the purified antibodies showed preferential binding to AD vs non-AD in soluble brain extracts and CSF, and did not appreciably bind to plaque fibrils by IHC.

TABLE 6

Summary of binding characteristics

| Antibody | Oligomers/ Monomers | Brain Extract AD/Non-AD | IHC - Plaque Staining (Frozen Section Brain 1630) | CSF |
|---|---|---|---|---|
| 301-3 | ++ | ++ | − | + |
| 301-11 | ++ | +++ | − | ++ |
| 301-17 | ++ | ++ | − | + |

* Scoring is relative to other clones not shown herein in the same sample category.

Example 3

Binding to A-Beta Synthetic Oligomers

To further verify and validate A-beta42 Oligomer binding, purified antibodies were covalently immobilized to a sensorchip, followed by the injection over the surface of commercially-prepared stable A-beta42 Oligomers (1 microM) (SynAging SAS, Vandceuvre-lès-Nancy, France).

Antibodies 301-3, 301-11 and 307-17, bound the stable A-beta 42 oligomers (1 microM) with binding response units (BRUs) of an average of 14.5 (301-3), 19.3 (301-11) and 30 (301-17), respectively. By comparison, the negative control IgG1 did not meaningfully bind to the oligomers (mean binding of BRU 2.5) while the pan-Aβ positive control antibody 6E10 bound with an average BRU of 90.

Example 4

Immunohistochemistry on Formalin Fixed Tissues

Human AD brain tissue sections were assessed using antibodies 301-11, 301-17. The patient had been previously characterized and diagnosed with Alzheimer's disease with a tripartite approach: (i) Bielschowsky silver method to demonstrate senile plaques and neurofibrillary tangles, (ii) Congo red to demonstrate amyloid and (iii) tau immunohistochemistry to demonstrate tangles and to confirm the senile plaques are "neuritic". This tissue was used to test plaque reactivity of selected monoclonal antibody clones. The brain tissues were fixed in 10% buffered formalin for several days and paraffin processed in the Sakura VIP tissue processors. Tissue sections were probed with 1 µg/ml of antibody with and without microwave antigen retrieval (AR). The pan-amyloid beta reactive antibody 6E10 was included along with selected antibody clones as a positive control. Antibodies were diluted in Antibody Diluent (Ventana), color was developed with OptiView DAB (Ventana). The staining was performed on the Ventana Benchmark XT IHC stainer. Images were obtained with an Olympus BX45 microscope. Images were analyzed blind by a professional pathologist with expertise in neuropathology.

As shown in Table 7 below, using fixed tissue, the tested antibodies were negative for specific staining of senile plaque amyloid. The 6E10 antibody, used as the positive control, showed strong plaque staining.

TABLE 7

| | Antibodies | Staining of senile plaque amyloid |
|---|---|---|
| | 301-11 | Neg |
| | 301-17 | Neg |
| Positive Control | 6E10 | strongly positive |

Example 5

Recombinant IgG1 and IgG2a Antibodies

Recombinant IgG1 and IgG2a 301-17 construct were made by grafting the CDRs of hybridoma-derived 301-17 onto a murine IgG1 or IgG2a backbone (WuXi, Biologics). The sequences are provided in Table 8.

TABLE 8

Heavy chain and light chain Sequences for 301-17 Isotypes

| Antibody and Isotype | cDNA Sequence | Polypeptide sequence |
|---|---|---|
| 301-17 IgG1 SEQ ID NO: 90, 91 | CAGGTGCAGCTGCAGCAGCCTGGCGCTGAGCTGGTGAAGCCTGGA GCCTCCGTGAAGATGTCCTGCAAGGCCTCCGGCTACTCCTTCACC AGCTACTGGATCAACTGGGTGAAGCAGAGGCCCGGACAGGGCCTG GAGTGGATTGGAGACGTGCACCCTGGCCGGGGAGTGTCCACCTAC AACGCCAAGTTCAAGTCCAAGGCCACCCTGACCCTGGACACCTCC AGCTCCACCGCCTACATGCAGCTGTCCTCCCTGACCTCCGAGGAC TCCGCCGTGTACTACTGCAGCAGGTCCCACGGCAACACCTACTGG TTTTTCGACGTGTGGGGCGCCGGAACCACAGTGACCGTGTCCTCC GCCAAAACGACACCCCCATCTGTCTATCCACTGGCCCCTGGATCT GCTGCCCAAACTAACTCCATGGTGACCCTGGGATGCCTGGTCAAG GGCTATTTCCCTGAGCCAGTGACAGTGACCTGGAACTCTGGATCC CTGTCCAGCGGTGTGCACACCTTCCCAGCTGTCCTGGAGTCTGAC CTCTACACTCTGAGCAGCTCAGTGACTGTCCCCTCCAGCCCTCGG CCCAGCGAGACCGTCACCTGCAACGTTGCCCACCCGGCCAGCAGC ACCAAGGTGGACAAGAAAATTGTGCCCAGGGATTGTGGTTGTAAG CCTTGCATATGTACAGTCCCAGAAGTATCATCTGTCTTCATCTTC CCCCCAAAGCCCAAGGATGTGCTCACCATTACTCTGACTCCTAAG GTCACGTGTGTTGTGGTAGACATCAGCAAGGATGATCCCGAGGTC CAGTTCAGCTGGTTTGTAGATGATGTGGAGGTGCACACAGCTCAG ACGCAACCCCGGGAGGAGCAGTTCAACAGCACTTTCCGCTCAGTC AGTGAACTTCCCATCATGCACCAGGACTGGCTCAATGGCAAGGAG TTCAAATGCAGGGTCAACAGTGCAGCTTTCCCTGCCCCCATCGAG AAAACCATCTCCAAAACCAAAGGCAGACCGAAGGCTCCACAGGTG TACAACATTCCACCTCCCAAGGAGCAGATGGCCAAGGATAAAGTC AGTCTGACCTGCATGATAACAGACTTCTTCCCTGAAGACATTACT GTGGAGTGGCAGTGGAATGGGCAGCCAGCGGAGAACTACAAGAAC ACTCAGCCCATCATGAACACGAATGGCTCTTACTTCGTCTACAGC AAGCTCAATGTGCAGAAGAGCAACTGGGAGGCAGGAAATACTTTC ACCTGCTCTGTGTTACATGAGGGCCTGCACAACCACCATACTGAG AAGAGCCTCTCCCACTCTCCTGGTAAATGATGA | QVQLQQPGAELVKPGA SVKMSCKASGYSFTSY WINWVKQRPGQGLEWI GDVHPGRGVSTYNAKF KSKATLTLDTSSSTAY MQLSSLTSEDSAVYYC SRSHGNTYWFFDVWGA GTTVTVSSAKTTPPSV YPLAPGSAAQTNSMVT LGCLVKGYFPEPVTVT WNSGSLSSGVHTFPAV LESDLYTLSSSVTVPS SPRPSETVTCNVAHPA SSTKVDKKIVPRDCGC KPCICTVPEVSSVFIF PPKPKDVLTITLTPKV TCVVVDISKDDPEVQF SWFVDDVEVHTAQTQP REEQFNSTFRSVSELP IMHQDWLNGKEFKCRV NSAAFPAPIEKTISKT KGRPKAPQVYTIPPPK EQMAKDKVSLTCMITD FFPEDITVEWQWNGQP AENYKNTQPIMNTNGS YFVYSKLNVQKSNWEA GNTFTCSVLHEGLHNH HTEKSLSHSPGK |
| 301-17 IgG2a SEQ ID NO: 92, 93 | CAGGTGCAGCTGCAGCAGCCTGGCGCTGAGCTGGTGAAGCCTGGA GCCTCCGTGAAGATGTCCTGCAAGGCCTCCGGCTACTCCTTCACC AGCTACTGGATCAACTGGGTGAAGCAGAGGCCCGGACAGGGCCTG GAGTGGATTGGAGACGTGCACCCTGGCCGGGGAGTGTCCACCTAC AACGCCAAGTTCAAGTCCAAGGCCACCCTGACCCTGGACACCTCC AGCTCCACCGCCTACATGCAGCTGTCCTCCCTGACCTCCGAGGAC TCCGCCGTGTACTACTGCAGCAGGTCCCACGGCAACACCTACTGG TTTTTCGACGTGTGGGGCGCCGGAACCACAGTGACCGTGTCCTCC GCCAAAACAACAGCCCCATCGGTCTATCCACTGGCCCCTGTGTGT GGAGATACAACTGGCTCCTCGGTGACTCTAGGATGCCTGGTCAAG GGTTATTTCCCTGAGCCAGTGACCTTGACCTGGAACTCTGGATCC CTGTCCAGTGGTGTGCACACCTTCCCAGCTGTCCTGCAGTCTGAC CTCTACACCCTCAGCAGCTCAGTGACTGTAACCTCGAGCACCTGG CCCAGCCAGTCCATCACCTGCAATGTGGCCCACCCGGCAAGCAGC ACCAAGGTGGACAAGAAAATTGAGCCCAGAGGGCCCACAATCAAG CCCTGTCCTCCATGCAAATGCCCAGCACCTAACCTCTTGGGTGGA CCATCCGTCTTCATCTTCCCTCCAAAGATCAAGGATGTACTCATG ATCTCCCTGAGCCCCATAGTCACATGTGTGGTGGTGGATGTGAGC GAGGATGACCCAGATGTCCAGATCAGCTGGTTTGTGAACAACGTG GAAGTACACACAGCTCAGACACAAACCCATAGAGAGGATTACAAC AGTACTCTCCGGGTGGTCAGTGCCCTCCCCATCCAGCACCAGGAC TGGATGAGTGGCAAGGAGTTCAAATGCAAGGTCAACAACAAAGAC CTCCCAGCGCCCATCGAGAGAACCATCTCAAAACCCAAAGGGTCA GTAAGAGCTCCACAGGTATATGTCTTGCCTCCACCAGAAGAAGAG ATGACTAAGAAACAGGTCACTCTGACCTGCATGGTCACAGACTTC ATGCCTGAAGACATTTACGTGGAGTGGACCAACAACGGGAAAACA GAGCTAAACTACAAGAACACTGAACCAGTCCTTGACTCTGATGGT TCTTACTTCATGTACAGCAAGCTGAGAGTGGAAAAGAAGAACTGG GTGGAAAGAAATAGCTACTCCTGTTCAGTGGTCCACGAGGGTCTG CACAATCACCACACGACTAAGAGCTTCTCCCGGACTCCGGGTAAA TGATGA | QVQLQQPGAELVKPGA SVKMSCKASGYSFTSY WINWVKQRPGQGLEWI GDVHPGRGVSTYNAKF KSKATLTLDTSSSTAY MQLSSLTSEDSAVYYC SRSHGNTYWFFDVWGA GTTVTVSSAKTTAPSV YPLAPVCGDTTGSSVT LGCLVKGYFPEPVTLT WNSGSLSSGVHTFPAV LQSDLYTLSSSVTVTS STWPSQSITCNVAHPA SSTKVDKKIEPRGPTI KPCPPCKCPAPNLLGG PSVFIFPPKIKDVLMI SLSPIVTCVVVDVSED DPDVQISWFVNNVEH TAQTQTHREDYNSTLR VVSALPIQHQDWMSGK EFKCKVNNKDLPAPIE RTISKPKGSVRAPQVY VLPPPEEEMTKKQVTL TCMVTDFMPEDIYVEW TNNGKTELNYKNTEPV LDSDGSYFMYSKLRVE KKNWVERNSYSCSVVH EGLHNHHTTKSFSRTP GK |
| 301-17 Kappa SEQ ID NO: 94, 95 | GATGTGCTGATGACCCAGACCCCTCTGTCCCTGCCTGTGTCCCTG GGCGATCAGGCCAGCATCTCCTGCAGGTCCTCCCAGTCCATCGTG CACTCCAACGGCAACACCTACCTGGAGTGGTACCTGCAGAAGCCC GGCCAGTCCCCCAAGCTGCTGATCTACAAGGTGTCCAACCGGTTC TCCGGCGTGCCCGATAGGTTCTCCGGATCCGGCTCCGGCACCGAC TTTACCCTGAAGATCTCCAGGGTGGAGGCCGAGGACCTGGGCGTG TACTACTGCTTTCAGGGCTCCCACGTGCCCTTCACCTTCGGCTCG GGCACCAAGCTGGAGATCAAGCGGGCTGATGCTGCACCAACTGTA TCCATCTTCCCACCATCCAGTGAGCAGTTAACATCTGGAGGTGCC TCAGTCGTGTGCTTCTTGAACAACTTCTACCCCAAAGACATCAAT GTCAAGTGGAAGATTGATGGCAGTGAACGACAAAATGCGTCCTG AACAGTTGGACTGATCAGGACAGCAAAGACAGCACCTACAGCATG | DVLMTQTPLSLPVSLG DQASISCRSSQSIVHS NGNTYLEWYLQKPGQS PKLLIYKVSNRFSVP DRFSGSGSGTDFTLKI SRVEAEDLGVYYCFQG SHVPFTFGSGTKLEIK RADAAPTVSIFPPSSE QLTSGGASVVCFLNNF YPKDINVKWKIDGSER QNGVLNSWTDQDSKDS TYSMSSTLTLTKDEYE |

TABLE 8-continued

```
AGCAGCACCCTCACGTTGACCAAGGACGAGTATGAACGACATAAC    RHNSYTCEATHKTSTS
AGCTATACCTGTGAGGCCACTCACAAGACATCAACTTCACCCATT    PIVKSFNRNEC
GTCAAGAGCTTCAACAGGAATGAGTGTTGATGA
```

The 301-17 IgG1 and IgG2a antibodies were tested and compared to the parent hybridoma-purified IgG3 antibody for binding characteristics as described below.

301-17 IgG2a ProteOn Biosensor (BioRad) Binding to AbO:

Recombinant 301-17 IgG2a and hybridoma-purified 301-17 IgG3 were captured with anti-mouse IgG or amine coupling on Proteon GLM Sensor chips and tested for AbO binding (SynAging AbO). AbO 3 fold-dilutions were used: 1 uM, 0.33 uM, 0.11 uM, 37 nM, 12.3 nM. Assay buffer was PBS-E+Tween 20+2 mg/ml BSA.

Results:
Approximate kinetic values were:
Hybridoma: KD=26.9 nM
IgG2a-301-17 antibody: KD=16.2-19.5 nM
No binding was detected with control mouse IgG.

301-17 IgG2a ProteOn Biosensor (BioRad) Binding to Cyclic Peptide Epitope:

Recombinant 301-17 IgG2a was amine-coupled to Proteon GLH biosensor chip and tested for binding to cyclopeptide of SEQ ID NO: 2 coupled to BSA. Cyclo-BSA 3-fold dilutions were used from 9 nM to 111 pM. Assay buffer was PBS-E+0.05% Tween+10 mg/ml BSA. Antibody 301-17 IgG2a was found to bind cyclic peptide (SEQ ID NO: 12) conjugated to BSA with an approximate KD of 17 pM (average of 3 tests). No or negligible binding was detected for other commercial Abeta antibodies tested (pan-Abeta 6E10, Biolegend) and rabbit anti-Abeta antibodies (D54D2, Cell Signaling; ab201060, (abcam; NBP1-78007, Novus).

301-17 IgG1 MAAS-2 Binding to AbO:

Recombinant 301-17 IgG1 and hybridoma-purified 301-17 IgG3 were immobilized on MAAS-2 sensor chips and tested for binding to AbO (SynAging) at 1 uM. Under the conditions tested, the recombinant IgG1 301-17 antibody gave a greater signal than the hybridoma-purified antibody in 2 tests (40-55 BRU vs 15-25 BRU, respectively). Little or no binding was detected with control mouse IgG.

301-17 IgG1 MAAS-2 Binding to Cyclic Peptide Epitope:

Recombinant 301-17 IgG1 was immobilized on MAAS-2 sensor chip and tested for binding to cyclopeptide of SEQ ID NO: 2 coupled to BSA at pH 6.5, 7.5 or 8.0. Equivalently high levels of binding were observed for 301-17 IgG1 under all 3 pH conditions (~400 BRUs). Little or no binding was detected under any of the pH conditions for control mouse IgG or the pan-Abeta 6E10 antibody (Biolegend)

Example 6

Inhibition of Oligomer Propagation

The biological functionality of antibodies was tested in vitro by examining their effects on Amyloid Beta (Aβ) aggregation using the Thioflavin T (ThT) binding assay. Aβ aggregation is induced by and propagated through nuclei of preformed small AB oligomers, and the complete process from monomeric Aβ to soluble oligomers to insoluble fibrils is accompanied by concomitantly increasing beta sheet formation. This can be monitored by ThT, a benzothiazole salt, whose excitation and emission maxima shifts from 385 to 450 nm and from 445 to 482 nm respectively when bound to beta sheet-rich structures and resulting in increased fluorescence. Briefly, Aβ 1-42 (Bachem Americas Inc., Torrance, Calif.) was solubilized, sonicated, diluted in Tris-EDTA buffer (pH7.4) and added to wells of a black 96-well microtitre plate (Greiner Bio-One, Monroe, N.C.) to which equal volumes of cyclopeptide raised antibody or irrelevant mouse IgG antibody isotype controls were added, resulting in a 1:5 molar ratio of Aβ1-42 peptide to antibody. ThT was added and plates incubated at room temperature for 24 hours, with ThT fluorescence measurements (excitation at 440 nm, emission at 486 nm) recorded every hour using a Wallac Victor3v 1420 Multilabel Counter (PerkinElmer, Waltham, Mass.). Fluorescent readings from background buffer were subtracted from all wells, and readings from antibody only wells were further subtracted from the corresponding wells.

Aβ42 aggregation, as monitored by ThT fluorescence, demonstrated a sigmoidal shape characterized by an initial lag phase with minimal fluorescence, an exponential phase with a rapid increase in fluorescence and finally a plateau phase during which the Aβ molecular species are at equilibrium and during which there is no increase in fluorescence. Co-incubation of Aβ42 with an irrelevant mouse antibody did not have any significant effect on the aggregation process. In contrast, co-incubation of Aβ42 with the test antibodies completely inhibited all phases of the aggregation process. Results obtained with antibody 301-11 are shown in FIG. 1.

Near identical results were obtained with 301-17 as well as 301-3.

As the ThT aggregation assay mimics the in vivo biophysical/biochemical stages of A13 propagation and aggregation from monomers, oligomers, protofibrils and fibrils that is pivotal in AD pathogenesis, the antibodies demonstrate the potential to completely abrogate this process. Isotype control performed using mouse IgG control antibody showed no inhibition.

Example 7

Toxicity Inhibition Assay

The inhibition of toxicity of A-beta42 oligomers by antibodies can be tested in a rat primary cortical neuron assay.

Antibody and control IgG are each adjusted to a concentration such as 2 mg/mL. Various molar ratios of A-beta oligomer and antibody are tested along with a vehicle control, A-beta oligomer alone and a positive control such as the neuroprotective peptide humanin HNG.

An exemplary set up is shown in Table 9.

Following preincubation for 10 minutes at room temperature, the volume is adjusted to 840 microlitres with culture medium. The solution is incubated for 5 min at 37 C. The solution is then added directly to the primary cortical neurons and cells are incubated for 24 h. Cell viability can be determined using the MTT assay.

TABLE 9

| AβO/MAB molar ratio | AβO (μL) | AβO (μM) | AB (μM) | AB (μL) | Medium (μL) | Final volume (μL) |
|---|---|---|---|---|---|---|
| 5/1 | 1.68 | 4.2 | 0.84 | 12.73 | 185.6 | 200 |
| 1/1 | 1.68 | 4.2 | 4.20 | 63.64 | 134.7 | 200 |
| 1/2 | 1.68 | 4.2 | 8.4 | 127.27 | 71.1 | 200 |

AβO working solution: 2.2 mg/mL-500 μM
CTRL vehicle: 1.68 μL of oligomer buffer + 127.3 μL PBS + 711 μL culture medium
CTRL AβO: 1.68 μL of AβO + 127.3 μL PBS + 711 μL culture medium
CTRL HNG: 1.68 μL of AβO + 8.4 μL HNG (100 nM final) + 127.3 μL PBS + 702.6 μL culture medium In the absence of A-beta oligomers, the 301-17 antibody alone had no effect on neuronal cell viability. When incubated in the presence of A-beta oligomers, the antibody inhibited A-beta oligomer-induced neuronal death at all molar ratios tested

Example 8

In Vivo Toxicity Inhibition Assay

The inhibition of toxicity of A-beta42 oligomers by the antibodies can be tested in vivo in mouse behavioral assays.
Novel Object Recognition (NOR)
The Novel Object Recognition (NOR) model utilizes the normal behavior of rodents to investigate novel objects for a significantly longer time than known objects. This test assesses recognition memory for items and its human equivalent is the visual pairwise-comparison (VPC). Recognition of objects is mediated by the perirhinal cortex in rodents, primates and humans. AD pathology develops first in the perirhinal and enthorinal cortex before the hippocampus. The VPC task detects memory deficit in mild cognitive impairment (MCI) and conversion from MCI to AD is predicted by this task (16).
Results:
The assay was performed by (SynAging SAS, Vandœuvre-lès-Nancy, France). Twelve C57BL6J mice per group (11-12 weeks old) were ICV-injected with vehicle (buffer used for Aβ oligomerization) or AβO (50 pmoles) in the presence of vehicle (PBS) or antibody 301-17 on day 0. The cognitive performance of all mice was determined by a Novel Object Recognition (NOR) test performed at days +7 and +8.
The study, done in blind to the operators, involved a total of 48 mice divided in four experimental groups with 12 mice per experimental group. All animals received a single (and unilateral) ICV injection of vehicle OR AβO in the absence or presence of antibody in a total volume of 5 μL. The experimental groups were defined as follow:
  GROUP A (vehicle CTRL): ICV injection of vehicle (n=12)
  GROUP B (AβO CTRL): ICV injection of AβO (n=12)
  GROUP C (Antibody CTRL): ICV injection of AβO+ antibody (n=12)
  GROUP D (Treatment): ICV injection of AβO+antibody (n=12)
Before ICV injection, 4 μL of antibody 1 (i.e. 112 pmoles) were incubated for 30 minutes at room temperature with 1 μL vehicle (i.e. buffer for Aβ oligomerization) or 1 μL AβO (50 pmoles) corresponding to an antibody/AβO molar ratio of 2.24.
At day 0, mice received a single 5 μL ICV injection of vehicle or AβO in the presence of vehicle or antibody.

The NOR test was conducted in one trial with all 48 mice at days +7 and +8. One day before the cognitive test (i.e. at Day +7), mice are habituated during a 10 min trial during which they are placed in an empty open field. The day of the cognitive test (i.e. Day +8), animals are placed in the same open field and are allowed to explore freely two identical objects for a trial of five minutes (acquisition trial). Then the animals are returned to their home cage for an inter-trial time of five minutes. During the retention trial, animals are allowed to explore two different objects: the same familiar object and one novel object. During this time, the experimenter, blind to the treatment, records the time the mouse is actively exploring each object. All trials are video recorded (Smart v3.0 software, Bioseb). A discrimination index (DI) is then generated: (DI)=(time exploring novel object−time exploring familiar object)/total exploration time. If the total exploration time is ≤5 s, animals are excluded from the calculation of the discrimination index and statistical analysis.
Mice from the vehicle control group (Group A) exhibited normal behavior with a mean discrimination index of 0.443±0.053. These results are in agreement with previous observations of similar control groups at SynAging. As expected, a single ICV injection of AβO (Group B) resulted in a significant impairment (p<0.0001) of the cognitive performance when compared to vehicle control mice; with a mean discrimination index of −0.062±0.048. AβO-injected mice were not able to discriminate between novel and familiar objects.
Mice dosed with antibody in the presence of vehicle (Group C) were found to exhibit normal cognitive performances with a mean discrimination index of 0.439±0.049. These mice were not significantly different from vehicle control mice (p=0.9163) and significantly different from AβO injected mice (p<0.0001).
When co-injected with Apo, the antibody fully prevented AβO-induced cognitive deficits in the NOR test. Indeed, mice from Group D exhibited a mean discrimination index of 0.481±0.055, not different from control mice (p=0.6126) but different from AβO-injected mice (p=0.0002). Taken together, the data suggest that antibody 301-17 offered protection against AβO-induced cognitive deficits.
Synaptic Markers
In addition to behavioral assays, brain tissue can be collected and analyzed for levels of synaptic markers (PSD95, SNAP25, synaptophysin) and inflammation markers (IL-1-beta and TNF-alpha). Mice are sacrificed at ~14 days post-ICV injection of oligomers and perfused with saline. Hippocampi are collected, snap frozen and stored at −80° C. until analyzed. Protein concentrations of homogenized samples are determined by BCA. Concentration of synaptic markers are determined using ELISA kits (Cloud-Clone Corp, USA). Typically, synaptic markers are reduced by 25-30% in mice injected with A-beta oligomers and restored to 90-100% by the humanin positive control. Concentrations of the IL-1-beta inflammatory markers are increased approximately 3-fold in mice injected with A-beta oligomers and this increase is largely prevented by humanin.

Brains are collected from mice that underwent the behavioral testing.

The hippocampus (relevant structure for memory formation) is dissected and homogenized in RIPA buffer containing an anti-protease cocktail. The tissue is lysed by 3 freeze thaw cycles carried out in liquid nitrogen and a water bath at 37 C. and the supernatants are recovered after centrifuging.

The lysate can be analyzed for levels of TNF-alpha (increases with inflammation) and levels of the synaptic markers PSD-95 and SNAP-25 (which go down when there is synaptic damage).

The antibody showed complete protection in the behavioral assay. It is expected that brains will also show an improvement in both SNAP25 and PSD-95 levels and a decrease in TNF-alpha levels in the brain.

Example 9

In Vivo Propagation Inhibition Assay

In vivo propagation of A-beta toxic oligomers and associated pathology can be studied in various rodent models of Alzheimer's disease (AD). For example, mice transgenic for human APP (e.g. APP23 mice) or human APP and PSEN1 (APPPS1 mice) express elevated levels of A-beta and exhibit gradual amyloid deposition with age accompanied by inflammation and neuronal damage. Intracerebral inoculation of oligomer-containing brain extracts can significantly accelerate this process (13, 14). These models provide a system to study inhibition of A-beta oligomer propagation by test antibodies administered intracerebrally or systemically.

TABLE 10

A-beta Sequences and compounds

1) HHQK (SEQ ID NO: 7)
   CGHHQKG, cyclo(CGHHQKG) (SEQ ID NO: 12)

TABLE 11

Human A-beta 1-42
DAEFRHDSGYEVHHQKLVFFAEDVGSNKGAIIGLMVGGVVIA
(SEQ ID NO: 73)

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Specifically, the sequences associated with each accession numbers provided herein including for example accession numbers and/or biomarker sequences (e.g. protein and/or nucleic acid) provided in the Tables or elsewhere, are incorporated by reference in its entirely.

The scope of the claims should not be limited by the preferred embodiments and examples, but should be given the broadest interpretation consistent with the description as a whole.

CITATIONS FOR REFERENCES REFERRED TO IN THE SPECIFICATION

[1] Gabriela A. N. Crespi, Stefan J. Hermans, Michael W. Parker, and Luke A. Miles. Molecular basis for mid-region amyloid-b capture by leading Alzheimer's disease immunotherapies SCIENTIFIC REPORTS|5: 9649, 20151 DOI: 10.1038/srep09649

[2] Vincent J. Hilser and Ernesto Freire. Structure-based calculation of the equilibrium folding pathway of proteins. correlation with hydrogen exchange protection factors. J. Mol. Biol., 262:756-772, 1996. The COREX approach.

[3] Samuel I. A. Cohen, et. al. Proliferation of amyloid-β42 aggregates occurs through a secondary nucleation mechanism. Proc. Natl. Acad. Sci. USA, 110(24):9758-9763, 2013.

[4] Pietro Sormanni, Francesco A. Aprile, and Michele Vendruscolo. The camsol method of rational design of protein mutants with enhanced solubility. J of Mol Biol, 427(2):478-490, 2015.

[5] Deborah Blacker, MD, ScD; Marilyn S. Albert, PhD; Susan S. Bassett, PhD; Rodney C. P. Go, PhD; Lindy E. Harrell, MD, PhD; Marshai F. Folstein, MD Reliability and Validity of NINCDS-ADRDA Criteria for Alzheimer's Disease The National Institute of Mental Health Genetics Initiative. Arch Neurol. 1994; 51(12):1198-1204. doi:10.1001/archneur.1994.00540240042014.

[6] Hannley, I. W. PEG-Peptide Conjugates 2014; 15, 1543-1559; dx.doi.org/10.1021/bm500246w

[7] Roberts, M J et al Chemistry for peptide and protein PEGylation 64: 116-127.

[8] J. X. Lu, W. Qiang, W. M. Yau, C. D. Schwieters, S. C. Meredith, R. Tycko, MOLECULAR STRUCTURE OF BETA-AMYLOID FIBRILS IN AD BRAIN TISSUE. CELL Vol. 154 p. 1257 (2013)

[9] Y. Xiao, B. M A, D. McElheny, S. Parthasarathy, F. Long, M. Hoshi, R. Nussinov, Y. Ishii, A BETA (1-42) FIBRIL STRUCTURE ILLUMINATES SELF-RECOGNITION AND REPLICATION OF AMYLOID IN ALZHEIMER'S DISEASE. NAT. STRUCT. MOL. BIOL. Vol. 22 p. 499 (2015).

[10] A. Petkova, W. Yau, R. Tycko EXPERIMENTAL CONSTRAINTS ON QUATERNARY STRUCTURE IN ALZHEIMER'S BETA-AMYLOID FIBRILS BIOCHEMISTRY V. 45 498 2006.

[11] Giulian D, Haverkamp L J, Yu J, Karshin W, Tom D, Li J, Kazanskaia A, Kirkpatrick J, Roher A E. The HHQK domain of β-amyloid provides a structural basis for the immunopathology of Alzheimer's disease, J. Biol Chem. 1998, 273(45), 29719-26.

[12] Winkler K, Scharnagl H, Tisljar U, Hoschützky H, Friedrich I, Hoffmann M M, Hüttinger M, Wieland H, Marz W. Competition of Aβ amyloid peptide and apolipoprotein E for receptor-mediated endocytosis. J. Lipid Res. 1999, 40(3), 447-55.

[13] SCIENTIFIC REPORTS|5: 9649|DOI: 10.1038/srep09649].

[14] Yu Y Z, Wang W B, Chao A, Chang Q, Liu S, Zhao M, et al. Strikingly reduced amyloid burden and improved behavioral performance in Alzheimer's disease mice immunized with recombinant chimeric vaccines by hexavalent foldable Ab 1-15 fused to toxin-derived carrier proteins. J Alzheimer's Dis 2014; 41:243-60.

[15] Wang, H C; Yu, Y Z; Liu, S; Zhao, M and Q Xu, Peripherally administered sera antibodies recognizing amyloid-oligomers mitigate Alzheimer's disease-like pathology and cognitive decline in aged 3×Tg-AD mice, Vaccine 2016.

[16] Zola S M, Manzanares C M, Clopton P, Lah J J, Levey A I. A behavioral task predicts conversion to mild cognitive impairment and Alzheimer's disease. *Am J Alzheimer's Dis & other dementia.* 2013, 28(2), 1790184

The invention claimed is:

1. A method of reducing amyloid beta (A-beta) oligomer propagation, the method comprising contacting a cell or tissue expressing A-beta oligomers with or administering to a subject in need thereof an effective amount of:

an A-beta oligomer specific or selective antibody comprising a light chain variable region and a heavy chain variable region, the heavy chain variable region comprising complementarity determining regions CDR-H1, CDR-H2, and CDR-H3, the light chain variable region comprising complementarity determining regions CDR-L1, CDR-L2, and CDR-L3 and with the amino acid sequences of the CDRs comprising SEQ ID NOs: 74-79 respectively;

to reduce A-beta aggregation, oligomer propagation, or A-beta aggregation and oligomer propagation.

2. The method of claim 1, wherein the heavy chain variable region and the light chain variable region of the antibody comprise the amino acid sequences of SEQ ID NOs: 42 and 56, respectively.

3. A method of alleviating or ameliorating one or more symptoms or conditions of Alzheimer's disease (AD), the method comprising administering to a subject in need thereof an effective amount of
  an antibody comprising a light chain variable region and a heavy chain variable region, the heavy chain variable region comprising complementarity determining regions CDR-H1, CDR-H2, and CDR-H3, the light chain variable region comprising complementarity determining regions CDR-L1, CDR-L2, and CDR-L3 and with the amino acid sequences of the CDRs comprising SEQ ID NOs: 74-79 respectively;
an immunoconjugate comprising the antibody, or a pharmaceutical composition comprising the antibody.

4. The method of claim 3, wherein the heavy chain variable region and the light chain variable region of the antibody comprise the amino acid sequences of SEQ ID NOs: 42 and 56, respectively.

5. The method of claim 3, wherein a biological sample from the subject is assessed for presence or levels of A-beta.

6. The method of claim 5, wherein the presence of oligomeric A-beta has been detected in the subject via in vitro measurement or imaging.

7. The method of claim 3, wherein the antibody, immunoconjugate or composition is administered directly to brain or other portion of CNS.

8. The method of claim 3, wherein the at least one antibody, immunoconjugate or composition is administered by parenteral, intravenous, subcutaneous, intramuscular, intracranial, intraventricular, intrathecal, intraorbital, ophthalmic, intraspinal, intracisternal, intraperitoneal, intranasal, aerosol or oral administration.

9. The method of claim 3, wherein the composition is administered systemically.

10. The method of claim 3, wherein the at least one antibody, immunoconjugate or composition is administered with one or more Alzheimer's disease treatments, and wherein the one or more Alzheimer's disease treatments is a beta-secretase inhibitor or a cholinesterase inhibitor.

11. A method of reducing toxicity induced by amyloid beta (A-beta) oligomers in Alzheimer's disease (AD) caused by A-beta oligomers, the method comprising administering to a subject in need thereof an effective amount of an antibody comprising a light chain variable region comprising complementarity determining regions CDR-L1, CDR-L2, and CDRL3 and a heavy chain variable region comprising complementarity determining regions CDR-H1, CDR-H2, and CDR-H3 wherein the CDR-L1, CDR-L2, CDR-L3, CDR-H1, CDR-H2, and CDR-H3 comprise the amino acid sequences of SEQ ID NOs: 74-79 respectively; an immunoconjugate comprising the antibody; or a pharmaceutical composition comprising the antibody.

12. The method of claim 11, wherein the heavy chain variable region and the light chain variable region of the antibody comprise the amino acid sequences of SEQ ID NOs: 42 and 56 respectively.

13. The method of claim 11, wherein the antibody, immunoconjugate or composition is administered directly to brain or other portion of CNS.

14. The method of claim 11, wherein the antibody, immunoconjugate or composition is administered by parenteral, intravenous, subcutaneous, intramuscular, intracranial, intraventricular, intrathecal, intraorbital, ophthalmic, intraspinal, intracisternal, intraperitoneal, intranasal, aerosol or oral administration.

15. The method of claim 14, wherein the antibody, immunoconjugate or composition is administered directly to the brain or other portion of the CNS using an implantable catheter and a pump.

16. The method of claim 11, wherein the composition is administered systemically.

17. The method of claim 11, wherein a biological sample from the subject is assessed for presence or levels of oligomeric A-beta.

18. The method of claim 17, wherein the presence of oligomeric A-beta has been detected in the subject via in vitro measurement or imaging.

19. The method of claim 11, wherein the antibody, immunoconjugate or composition is administered with a beta-secretase inhibitor or a cholinesterase inhibitor.

* * * * *